US010744305B2

(12) United States Patent
Burkholz et al.

(10) Patent No.: US 10,744,305 B2
(45) Date of Patent: Aug. 18, 2020

(54) ERGONOMIC IV SYSTEMS AND METHODS

(71) Applicant: Becton, Dickinson and Company, Franklin Lakes, NJ (US)

(72) Inventors: Jonathan Karl Burkholz, Salt Lake City, UT (US); Bart D. Peterson, Farmington, UT (US); Huibin Liu, West Jordan, UT (US); Stephen T. Bornhoft, Sandy, UT (US); Weston F. Harding, Lehi, UT (US); Young Zhang, Shanghai (CN); Ralph L. Sonderegger, Farmington, UT (US); Bin Wang, Sandy, UT (US)

(73) Assignee: Becton, Dickinson and Company, Franklin, NJ (US)

( * ) Notice: Subject to any disclaimer, the term of this patent is extended or adjusted under 35 U.S.C. 154(b) by 725 days.

(21) Appl. No.: 15/286,168

(22) Filed: Oct. 5, 2016

(65) Prior Publication Data
US 2017/0120011 A1  May 4, 2017

Related U.S. Application Data

(60) Provisional application No. 62/296,385, filed on Feb. 17, 2016, provisional application No. 62/296,383, (Continued)

(51) Int. Cl.
*A61M 25/06* (2006.01)
*A61M 25/00* (2006.01)
(Continued)

(52) U.S. Cl.
CPC ........ *A61M 25/0606* (2013.01); *A61M 5/158* (2013.01); *A61M 25/0097* (2013.01);
(Continued)

(58) Field of Classification Search
CPC .............. A61M 25/0606; A61M 5/158; A61M 25/0097; A61M 25/0102; A61M 25/0637
(Continued)

(56) References Cited

U.S. PATENT DOCUMENTS 3,046,984 A   7/1962  Eby
3,547,119 A   12/1970 Hall et al.
(Continued)

FOREIGN PATENT DOCUMENTS

CA   2 133 053 A1    3/1995
CN   101879341 A    11/2010
(Continued)

OTHER PUBLICATIONS

Silva, Elson, Email Regarding "Respecting Hydrology Science and IP Rights—US Pat. Application 20110130728," pp. 1-6 (Jun. 2, 2011).

*Primary Examiner* — Phillip A Gray
(74) *Attorney, Agent, or Firm* — Kirton & McConkie; Craig Metcalf; Kevin Stinger

(57) ABSTRACT

An IV catheter system may have a catheter component with a catheter hub, a cannula extending distally from the catheter hub, and a push feature protruding outwardly from the catheter hub. The IV catheter system may also have a needle component with a needle hub, a needle extending distally from the needle hub along an axis, and a grip extending from the needle hub, generally parallel to the axis, with a pull feature. In the insertion configuration, the needle may be positioned within the cannula and the distal end of the needle hub may be seated in a needle port of the catheter hub. In the fluid delivery configuration, the needle may be positioned outside the catheter hub. The push and pull features may be positioned to facilitate manipulation with a single hand to
(Continued)

move the IV catheter system from an insertion configuration to a fluid delivery configuration.

18 Claims, 29 Drawing Sheets

Related U.S. Application Data filed on Feb. 17, 2016, provisional application No. 62/247,607, filed on Oct. 28, 2015, provisional application No. 62/247,617, filed on Oct. 28, 2015, provisional application No. 62/247,626, filed on Oct. 28, 2015, provisional application No. 62/247,621, filed on Oct. 28, 2015, provisional application No. 62/247,596, filed on Oct. 28, 2015, provisional application No. 62/247,599, filed on Oct. 28, 2015, provisional application No. 62/247,624, filed on Oct. 28, 2015.

(51) Int. Cl.
*A61M 5/158* (2006.01)
*A61M 25/01* (2006.01)

(52) U.S. Cl.
CPC .... *A61M 25/0102* (2013.01); *A61M 25/0637* (2013.01); *A61M 25/0693* (2013.01); *A61M 2005/1586* (2013.01); *A61M 2025/0008* (2013.01); *A61M 2025/0098* (2013.01); *A61M 2205/586* (2013.01); *A61M 2205/6063* (2013.01)

(58) Field of Classification Search
USPC .................................................. 604/164.07
See application file for complete search history.

(56) References Cited

U.S. PATENT DOCUMENTS

| | | | |
|---|---|---|---|
| 3,589,361 A | 6/1971 | Loper et al. | |
| 3,827,434 A | 8/1974 | Thompson et al. | |
| 3,853,127 A | 12/1974 | Spademan | |
| 3,859,998 A | 1/1975 | Thomas et al. | |
| 4,003,403 A | 1/1977 | Nehring | |
| 4,043,346 A | 8/1977 | Mobley et al. | |
| 4,099,528 A | 7/1978 | Sorenson et al. | |
| 4,149,539 A | 4/1979 | Cianci | |
| 4,172,448 A | 10/1979 | Brush | |
| 4,177,809 A | 12/1979 | Moorehead | |
| 4,193,399 A | 3/1980 | Robinson | |
| 4,200,096 A | 4/1980 | Charvin | |
| 4,269,186 A | 5/1981 | Loveless et al. | |
| 4,311,137 A | 1/1982 | Gerard | |
| 4,317,445 A | 3/1982 | Robinson | |
| 4,326,519 A * | 4/1982 | D'Alo | A61M 25/0637 604/165.04 |
| 4,353,369 A | 10/1982 | Muetterties et al. | |
| 4,362,156 A | 12/1982 | Feller, Jr. et al. | |
| 4,365,630 A | 12/1982 | McFarlane | |
| 4,387,879 A | 6/1983 | Tauschinski | |
| 4,419,094 A | 12/1983 | Patel | |
| 4,445,893 A | 5/1984 | Bodicky | |
| 4,449,693 A | 5/1984 | Gereg | |
| 4,496,348 A | 1/1985 | Genese et al. | |
| 4,525,157 A | 6/1985 | Vaillancourt | |
| 4,531,935 A | 7/1985 | Berryessa | |
| 4,682,980 A | 7/1987 | Suzuki | |
| 4,701,162 A | 10/1987 | Rosenberg | |
| 4,703,761 A | 11/1987 | Rathbone et al. | |
| 4,758,225 A | 7/1988 | Cox et al. | |
| 4,765,588 A | 8/1988 | Atkinson | |
| 4,772,264 A | 9/1988 | Cragg | |
| 4,813,939 A | 3/1989 | Marcus | |
| 4,834,708 A * | 5/1989 | Pillari | A61M 25/0637 604/165.04 |
| 4,842,591 A | 6/1989 | Luther | |
| 4,874,377 A | 10/1989 | Newgard et al. | |
| 4,894,052 A | 1/1990 | Crawford | |
| 4,917,668 A | 4/1990 | Haindl | |
| 4,917,671 A | 4/1990 | Chang | |
| 4,925,444 A | 5/1990 | Orkin et al. | |
| 4,935,010 A | 6/1990 | Cox et al. | |
| 4,950,257 A | 8/1990 | Hibbs et al. | |
| 4,966,586 A | 10/1990 | Vaillancourt | |
| D315,822 S | 3/1991 | Ryan | |
| 5,032,116 A | 7/1991 | Peterson et al. | |
| 5,041,097 A | 8/1991 | Johnson | |
| 5,053,014 A | 10/1991 | Van Heugten | |
| 5,057,087 A | 10/1991 | Harmon | |
| 5,059,186 A | 10/1991 | Yamamoto et al. | |
| 5,062,836 A | 11/1991 | Wendell | |
| 5,064,416 A | 11/1991 | Newgard et al. | |
| 5,084,023 A | 1/1992 | Lemieux | |
| 5,085,645 A | 2/1992 | Purdy et al. | |
| 5,108,374 A | 4/1992 | Lemieux | |
| 5,127,905 A | 7/1992 | Lemieux | |
| 5,135,504 A | 8/1992 | McLees | |
| 5,154,703 A | 10/1992 | Bonaldo | |
| 5,156,596 A | 10/1992 | Balbierz et al. | |
| 5,176,653 A | 1/1993 | Metais | |
| 5,176,662 A | 1/1993 | Bartholomew et al. | |
| 5,201,717 A | 4/1993 | Wyatt et al. | |
| 5,211,634 A | 5/1993 | Vaillancourt | |
| 5,215,525 A | 6/1993 | Sturman | |
| 5,215,528 A | 6/1993 | Purdy et al. | |
| 5,215,529 A | 6/1993 | Fields et al. | |
| 5,226,883 A | 7/1993 | Katsaros et al. | |
| 5,234,410 A | 8/1993 | Graham et al. | |
| 5,242,411 A | 9/1993 | Yamamoto et al. | |
| 5,254,097 A | 10/1993 | Schock et al. | |
| 5,267,971 A | 12/1993 | Brimhall | |
| 5,269,764 A | 12/1993 | Vetter et al. | |
| 5,273,546 A | 12/1993 | McLaughlin et al. | |
| 5,290,222 A | 3/1994 | Feng et al. | |
| 5,290,246 A | 3/1994 | Yamamoto et al. | |
| 5,295,969 A | 3/1994 | Fischell et al. | |
| 5,306,243 A | 4/1994 | Bonaldo | |
| 5,312,359 A | 5/1994 | Wallace | |
| 5,328,482 A | 7/1994 | Sircom et al. | |
| 5,330,435 A | 7/1994 | Vaillancourt | |
| 5,342,315 A | 8/1994 | Rowe et al. | |
| 5,350,363 A | 9/1994 | Goode et al. | |
| 5,352,205 A | 10/1994 | Dales et al. | |
| 5,354,281 A * | 10/1994 | Chen | A61M 25/0637 604/165.03 |
| 5,356,381 A | 10/1994 | Ensminger et al. | |
| 5,368,029 A | 11/1994 | Holcombe et al. | |
| 5,405,323 A | 4/1995 | Rogers et al. | |
| 5,447,501 A | 9/1995 | Karlsson et al. | |
| 5,456,675 A | 10/1995 | Wolbring et al. | |
| 5,458,658 A | 10/1995 | Sircom | |
| 5,487,728 A | 1/1996 | Vaillancourt | |
| 5,498,241 A | 3/1996 | Fabozzi | |
| 5,509,912 A | 4/1996 | Vaillancourt et al. | |
| 5,520,666 A | 5/1996 | Choudhury et al. | |
| 5,542,932 A | 8/1996 | Daugherty | |
| 5,549,566 A | 8/1996 | Elias et al. | |
| 5,549,576 A | 8/1996 | Patterson et al. | |
| 5,549,577 A | 8/1996 | Siegel et al. | |
| 5,562,631 A | 10/1996 | Bogert | |
| 5,562,633 A | 10/1996 | Wozencroft | |
| 5,573,510 A | 11/1996 | Isaacson | |
| 5,575,769 A | 11/1996 | Vaillancourt | |
| 5,575,777 A | 11/1996 | Cover et al. | |
| 5,584,809 A | 12/1996 | Gaba | |
| 5,599,310 A | 2/1997 | Bogert | |
| 5,601,536 A | 2/1997 | Crawford et al. | |
| 5,613,663 A | 3/1997 | Schmidt et al. | |
| 5,651,772 A | 7/1997 | Arnett | |
| 5,657,963 A | 8/1997 | Hinchliffe et al. | |
| 5,676,656 A | 10/1997 | Brimhall | |
| 5,690,612 A | 11/1997 | Lopez et al. | |

(56) References Cited

U.S. PATENT DOCUMENTS

| | | |
|---|---|---|
| 5,690,619 A | 11/1997 | Erskine |
| 5,697,907 A | 12/1997 | Gaba |
| 5,697,914 A | 12/1997 | Brimhall |
| 5,697,915 A | 12/1997 | Lynn |
| 5,699,821 A | 12/1997 | Paradis |
| 5,700,244 A | 12/1997 | Kriesel |
| 5,700,250 A | 12/1997 | Erskine |
| 5,704,919 A | 1/1998 | Kraus et al. |
| 5,718,688 A | 2/1998 | Wozencroft |
| 5,730,123 A | 3/1998 | Lorenzen et al. |
| 5,738,144 A | 4/1998 | Rogers |
| 5,749,856 A | 5/1998 | Zadini et al. |
| 5,749,861 A | 5/1998 | Guala et al. |
| 5,772,636 A | 6/1998 | Brimhall et al. |
| 5,800,399 A | 9/1998 | Bogert et al. |
| 5,806,831 A | 9/1998 | Paradis |
| 5,810,780 A | 9/1998 | Brimhall et al. |
| 5,817,069 A | 10/1998 | Arnett |
| 5,843,046 A | 12/1998 | Motisi et al. |
| 5,853,393 A | 12/1998 | Bogert |
| 5,882,345 A | 3/1999 | Yoon |
| 5,911,710 A | 6/1999 | Barry et al. |
| 5,935,109 A | 8/1999 | Donnan |
| 5,935,110 A | 8/1999 | Brimhall |
| 5,947,932 A | 9/1999 | Desecki et al. |
| 5,954,698 A | 9/1999 | Pike |
| 5,961,497 A | 10/1999 | Larkin |
| 5,967,490 A | 10/1999 | Pike |
| 6,039,302 A | 3/2000 | Cote, Sr. et al. |
| 6,056,726 A | 5/2000 | Isaacson |
| 6,077,244 A | 6/2000 | Botich et al. |
| 6,117,108 A | 9/2000 | Woehr et al. |
| 6,142,981 A | 11/2000 | Heck et al. |
| 6,156,010 A * | 12/2000 | Kuracina ......... A61M 25/0693 600/577 |
| 6,171,287 B1 | 1/2001 | Lynn et al. |
| 6,206,851 B1 | 3/2001 | Prosl |
| 6,221,047 B1 | 4/2001 | Greene et al. |
| 6,224,569 B1 | 5/2001 | Brimhall |
| 6,273,869 B1 | 8/2001 | Vaillancourt |
| 6,287,278 B1 | 9/2001 | Woehr et al. |
| D451,599 S | 12/2001 | Crawford et al. |
| D451,600 S | 12/2001 | Crawford et al. |
| 6,379,332 B1 | 4/2002 | Van Landuyt |
| D458,678 S | 6/2002 | Cindrich |
| D458,994 S | 6/2002 | Cindrich |
| 6,440,119 B1 | 8/2002 | Nakada et al. |
| 6,461,362 B1 | 10/2002 | Halseth et al. |
| 6,485,473 B1 | 11/2002 | Lynn |
| 6,497,994 B1 | 12/2002 | Kafrawy |
| 6,506,181 B2 | 1/2003 | Meng et al. |
| D469,870 S | 2/2003 | Niermann et al. |
| 6,565,542 B2 | 5/2003 | Kumar et al. |
| 6,575,960 B2 | 6/2003 | Becker et al. |
| 6,595,954 B1 | 7/2003 | Luther et al. |
| 6,595,981 B2 | 7/2003 | Huet |
| 6,616,630 B1 | 9/2003 | Woehr |
| 6,652,486 B2 | 11/2003 | Bialecki et al. |
| 6,663,592 B2 | 12/2003 | Rhad et al. |
| 6,689,102 B2 | 2/2004 | Greene |
| 6,695,814 B2 | 2/2004 | Greene et al. |
| 6,699,221 B2 | 3/2004 | Vaillancourt |
| 6,709,419 B2 | 3/2004 | Woehr |
| 6,719,726 B2 | 4/2004 | Meng et al. |
| 6,740,063 B2 | 5/2004 | Lynn |
| D491,266 S | 6/2004 | Cindrich et al. |
| D492,031 S | 6/2004 | Cindrich et al. |
| 6,749,588 B1 | 6/2004 | Howell et al. |
| D492,774 S | 7/2004 | Cindrich et al. |
| 6,837,884 B2 | 1/2005 | Woloszko |
| 6,883,778 B1 | 4/2005 | Newton et al. |
| 7,008,404 B2 | 3/2006 | Nakajima |
| 7,347,839 B2 | 3/2008 | Hiejima |
| 7,396,346 B2 | 7/2008 | Nakajima |
| 7,470,254 B2 | 12/2008 | Basta et al. |
| D592,302 S | 5/2009 | Stokes et al. |
| 7,670,317 B2 | 3/2010 | Cindrich et al. |
| 7,694,403 B2 | 4/2010 | Moulton |
| 7,736,339 B2 | 6/2010 | Woehr et al. |
| 7,905,856 B2 | 3/2011 | McGuckin, Jr. et al. |
| 7,914,494 B2 | 3/2011 | Hiejima |
| 8,066,670 B2 | 11/2011 | Cluff et al. |
| 8,066,675 B2 | 11/2011 | Cindrich et al. |
| 8,070,725 B2 | 12/2011 | Christensen |
| 8,357,119 B2 | 1/2013 | Stout et al. |
| 8,361,020 B2 | 1/2013 | Stout et al. |
| 8,388,583 B2 | 3/2013 | Stout et al. |
| 8,574,203 B2 | 11/2013 | Stout et al. |
| 8,597,252 B2 | 12/2013 | Burkholz et al. |
| 8,641,675 B2 | 2/2014 | Stout et al. |
| 8,679,063 B2 | 3/2014 | Stout et al. |
| D713,522 S | 9/2014 | Woehr et al. |
| D819,802 S | 6/2018 | Burkholz et al. |
| D835,262 S | 12/2018 | Burkholz et al. |
| D837,368 S | 1/2019 | Burkholz et al. |
| 2001/0053895 A1 | 12/2001 | Vaillancourt |
| 2002/0072712 A1 | 6/2002 | Nool et al. |
| 2002/0082546 A1 | 6/2002 | Crank et al. |
| 2002/0177814 A1 | 11/2002 | Meng et al. |
| 2003/0083620 A1 | 5/2003 | Luther et al. |
| 2004/0078003 A1 | 4/2004 | Smith et al. |
| 2004/0092889 A1 | 5/2004 | Ferguson et al. |
| 2004/0102735 A1 | 5/2004 | Moulton et al. |
| 2004/0181192 A1 | 9/2004 | Cuppy |
| 2004/0193112 A1 | 9/2004 | Glazier et al. |
| 2004/0204681 A1 | 10/2004 | Thoresen et al. |
| 2004/0225260 A1 | 11/2004 | Villa et al. |
| 2004/0243060 A1 | 12/2004 | Rossi et al. |
| 2004/0243061 A1 | 12/2004 | McGurk |
| 2005/0273019 A1 | 12/2005 | Conway et al. |
| 2005/0277879 A1 | 12/2005 | Daga |
| 2006/0163515 A1 | 7/2006 | Ruschke |
| 2007/0043334 A1 | 2/2007 | Guala |
| 2007/0083157 A1 | 4/2007 | Belley et al. |
| 2007/0083162 A1 | 4/2007 | O'Reagan et al. |
| 2007/0093778 A1 | 4/2007 | Cindrich et al. |
| 2007/0191777 A1 | 8/2007 | King |
| 2007/0225648 A1 | 9/2007 | Winsor et al. |
| 2007/0233007 A1 | 10/2007 | Adams |
| 2008/0039796 A1 | 2/2008 | Nakajima |
| 2008/0108944 A1 | 5/2008 | Woehr et al. |
| 2008/0132832 A1 | 6/2008 | McKinnon et al. |
| 2008/0167577 A1 | 7/2008 | Weilbacher et al. |
| 2008/0255473 A1 | 10/2008 | Dalebout et al. |
| 2008/0287906 A1 | 11/2008 | Burkholz et al. |
| 2009/0054845 A1 | 2/2009 | Puhasmagi et al. |
| 2009/0099431 A1 | 4/2009 | Dalebout et al. |
| 2009/0287189 A1 | 11/2009 | Suwito |
| 2010/0204648 A1 | 8/2010 | Stout et al. |
| 2010/0204675 A1 | 8/2010 | Woehr et al. |
| 2010/0222746 A1 | 9/2010 | Burkholz |
| 2010/0280455 A1 | 11/2010 | Ogawa et al. |
| 2011/0046570 A1 | 2/2011 | Stout et al. |
| 2011/0054403 A1 | 3/2011 | Tanabe et al. |
| 2011/0130728 A1 | 6/2011 | McKinnon |
| 2012/0016265 A1 | 1/2012 | Peterson et al. |
| 2012/0016307 A1 | 1/2012 | Burkholz et al. |
| 2012/0053523 A1 | 3/2012 | Harding |
| 2013/0090608 A1 | 4/2013 | Stout et al. |
| 2013/0218082 A1 | 8/2013 | Hyer et al. |
| 2013/0237925 A1 | 9/2013 | Trainer et al. |
| 2014/0046258 A1 | 2/2014 | Stout et al. |
| 2014/0107584 A1 | 4/2014 | Rosenberg et al. |
| 2014/0364809 A1 | 12/2014 | Isaacson et al. |
| 2015/0224296 A1 | 8/2015 | Winsor |
| 2017/0120008 A1 | 5/2017 | Burkholz et al. |
| 2017/0120014 A1 | 5/2017 | Harding et al. |
| 2017/0216535 A1 | 8/2017 | Mao |
| 2017/0347913 A1 | 12/2017 | Isaacson et al. |

FOREIGN PATENT DOCUMENTS

| | | |
|---|---|---|
| CN | 102440822 A | 5/2012 |
| CN | 102716541 A | 10/2012 |

(56) References Cited

FOREIGN PATENT DOCUMENTS

| | | |
|---|---|---|
| CN | 203852671 | 10/2014 |
| DE | 20 2009 009 602 U1 | 12/2009 |
| EP | 0 268 480 A1 | 5/1988 |
| EP | 0 732 120 A1 | 9/1996 |
| EP | 0 812 601 A2 | 12/1997 |
| EP | 0 993 839 A1 | 4/2000 |
| EP | 1 306 097 | 5/2003 |
| EP | 1 679 043 A1 | 7/2006 |
| EP | 1 884 257 A1 | 2/2008 |
| EP | 1 944 049 A1 | 7/2008 |
| EP | 2022421 | 2/2009 |
| EP | 2 044 970 A1 | 4/2009 |
| EP | 2 327 434 A1 | 6/2011 |
| GB | 2508466 A | 6/2014 |
| JP | S56102253 | 8/1981 |
| JP | S5832774 | 2/1983 |
| JP | H06-086821 | 3/1994 |
| JP | H09-509075 | 9/1997 |
| JP | 2000279527 | 10/2000 |
| JP | 2004528127 | 9/2004 |
| JP | 2011045544 | 3/2011 |
| JP | 2012521796 | 9/2012 |
| JP | 2012200425 | 10/2012 |
| JP | 3188771 | 1/2014 |
| JP | 2014108112 | 6/2014 |
| WO | 88/07388 A1 | 10/1988 |
| WO | 97/45151 | 12/1997 |
| WO | 98/42393 A1 | 10/1998 |
| WO | 99/34849 A1 | 7/1999 |
| WO | 01/12254 A1 | 2/2001 |
| WO | 02/096495 | 12/2002 |
| WO | 2004/032995 A2 | 4/2004 |
| WO | 2004/082727 | 9/2004 |
| WO | 2004/087247 | 10/2004 |
| WO | 2004/098685 A1 | 11/2004 |
| WO | 2006/037638 A1 | 4/2006 |
| WO | 2007/052655 | 5/2007 |
| WO | 2008/022258 A2 | 2/2008 |
| WO | 2008/045761 A2 | 4/2008 |
| WO | 2008/052790 A2 | 5/2008 |
| WO | 2008/058132 A2 | 5/2008 |
| WO | 2008/058133 A2 | 5/2008 |
| WO | 2009/114833 A1 | 9/2009 |
| WO | 2010/093791 A1 | 8/2010 |
| WO | 2010/111283 | 9/2010 |
| WO | 2010/111285 A1 | 9/2010 |
| WO | 2011/055287 | 5/2011 |
| WO | 2011/109542 A1 | 9/2011 |
| WO | 2016/007442 | 1/2016 |
| WO | 2017/062579 | 4/2017 |

\* cited by examiner

ERGONOMIC IV SYSTEMS AND METHODS

RELATED APPLICATIONS

This application claims the benefit of U.S. Provisional Patent Application No. 62/247,596, which was filed on Oct. 28, 2015, U.S. Provisional Patent Application No. 62/296,383, which was filed on Feb. 17, 2016, U.S. Provisional Patent Application No. 62/247,599, which was filed Oct. 28, 2015, U.S. Provisional Patent Application No. 62/247,617, which was filed on Oct. 28, 2015, U.S. Provisional Patent Application Ser. No. 62/247,607, which was filed Oct. 28, 2015, U.S. Provisional Patent Application Ser. No. 62/247,621, which was filed Oct. 28, 2015, U.S. Provisional Patent Application Ser. No. 62/247,624, which was filed Oct. 28, 2015, U.S. Provisional Application No. 62/247,626, which was filed on Oct. 28, 2015, and U.S. Provisional Application No. 62/296,385, which was filed on Feb. 17, 2016, each of which is incorporated herein by reference in their entirety.

BACKGROUND

The present invention is generally directed to systems and methods for intravenous ("IV") delivery, by which fluids can be administered directly to the vascular system of a patient. More particularly, the present invention is directed to IV catheter systems and methods that facilitate insertion into the patient and/or motion from an insertion configuration to a fluid delivery configuration in which fluid can be delivered to the patient through the IV catheter system. An IV catheter system according to the invention is used broadly herein to describe components used to deliver the fluid to the patient, for use in arterial, intravenous, intravascular, peritoneal, and/or non-vascular administration of fluid. Of course, one of skill in the art may use an IV catheter system to administer fluids to other locations within a patient's body.

Known IV catheter systems and methods have a number of deficiencies. Many such systems require the clinician to use two hands to position the IV catheter system and/or insert the needle into the fluid delivery location on the patient (for example, the vein into which fluid is to be delivered). Further, many such systems require the clinician to use two hands to move the IV catheter system from the insertion configuration to a fluid delivery configuration, in which the needle is removed from the cannula to permit fluid to be delivered to the vein through the cannula. Thus, the clinician is required to stabilize the patient's arm or other body part having the fluid delivery location prior to insertion of the IV catheter system. As a result, extra time is required for the clinician to initiate transfusion. Further, the clinician is unable to perform any other task, such as stabilizing or reassuring the patient, during insertion and/or motion to the fluid delivery configuration.

Accordingly, there is a need for IV catheter systems and methods that facilitate IV catheter system placement, insertion, and/or preparation for fluid delivery. There is a further need for such IV catheter systems that are inexpensive, easy to manufacture, and versatile.

BRIEF SUMMARY OF THE INVENTION

Embodiments of the present invention are generally directed to an IV catheter system with enhanced ergonomics. In some embodiments, the IV catheter system may be inserted and moved to the fluid delivery configuration with only one hand. The IV catheter system may have a catheter component with a catheter component and a needle component. The catheter component may have a catheter hub with a catheter hub distal end and a catheter hub proximal end. The catheter hub may be shaped to define a chamber extending between the catheter hub distal end and the catheter hub proximal end, and a needle port at the catheter hub proximal end that provides access to the chamber. The catheter component may also have a cannula extending distally from the catheter hub distal end, and a push feature protruding outwardly from the catheter hub. The needle component may have a needle hub with a needle hub distal end and a needle hub proximal end, a needle extending distally from the needle hub distal end along an axis, and a grip extending from the needle hub, generally parallel to the axis. The grip may have a pull feature. In the insertion configuration, the needle may be positioned within the cannula and the needle hub distal end may be seated in the needle port. In the fluid delivery configuration, the needle may be positioned outside the catheter hub. The push feature may be positioned to receive first contact from a first digit of a hand of a user to urge the catheter hub distally. Further, the pull feature may be positioned to receive second contact from a second digit of the hand simultaneously with receipt of the first contact such that the first and second contacts cooperate to urge the IV catheter system to move from the insertion configuration to the fluid delivery configuration.

The catheter hub may have a catheter hub intermediate portion between the catheter hub proximal end and the catheter hub distal end. The catheter component may further have an extension tubing junction extending outwardly from the catheter hub intermediate portion to connect the catheter hub to extension tubing. The push feature may have a push surface extending between the catheter hub intermediate portion and the extension tubing junction. The push surface may be oriented substantially perpendicular to the axis.

The grip may have a recess shaped to receive the extension tubing junction in the insertion configuration. Moving the IV catheter system from the insertion configuration to the fluid delivery configuration may include rotating the needle component relative to the catheter component about the axis to withdraw the extension tubing junction from the recess.

The catheter component may further have a septum within the chamber, through which the needle passes in the insertion configuration. The septum may be configured to provide a sufficiently low resistance to withdrawal of the needle through the septum to enable the hand, alone, to move the IV catheter system from the insertion configuration to the fluid delivery configuration.

The catheter component may further have a securement platform with a first wing extending from the catheter hub, generally parallel to the axis. In the fluid delivery configuration, the first wing may rest on skin of a patient receiving fluid through the IV catheter system.

The securement platform may further have a second wing extending from the catheter hub, generally coplanar with the first wing. In the fluid delivery configuration, the second wing may also rest on the skin.

In the insertion configuration, the first wing and the grip may be generally parallel to each other and may be positioned in abutting relation to each other. During motion of the IV catheter system from the insertion configuration to the fluid delivery configuration, the grip may slide along the first wing.

At least one of the first wing and the grip may have one or more alignment features. The alignment features may cause the first wing and the grip to remain positioned in abutting relation to each other during motion of the IV catheter system from the insertion configuration toward the fluid delivery configuration.

At least one of the first wing and the grip may have one or more locking features. The locking features may cause the IV catheter system to remain in the insertion configuration until the first contact and the second contact cooperate to provide a disengagement force sufficient to unlock the one or more locking features.

The pull feature may be a leading edge of the grip. The leading edge may be shaped and sized to comfortably receive the second contact.

According to one exemplary method for preparing an IV catheter system to deliver fluid to a patient, the IV catheter system may again have an insertion configuration and a fluid delivery configuration. The method may include positioning the IV catheter system proximate a fluid delivery location of a patient. The IV catheter system may have a catheter component and a needle component. The catheter component may have a catheter hub that has a catheter hub distal end and a catheter hub proximal end. The catheter hub may be shaped to define a chamber extending between the catheter hub distal end and the catheter hub proximal end, and a needle port at the catheter hub proximal end that provides access to the chamber. The catheter component may also have a cannula extending distally from the catheter hub distal end, and a push feature protruding outwardly from the catheter hub. The needle component may have a needle hub that has a needle hub distal end and a needle hub proximal end. The needle component may also have a needle extending distally from the needle hub distal end along an axis, and a grip extending generally parallel to the axis, the grip comprising a pull feature. The method may also include, with the IV catheter system in the insertion configuration, in which the needle is positioned within the cannula and the needle hub distal end is seated in the needle port, using a single hand to insert the needle and the cannula into the fluid delivery location. Further, the method may include, with the needle and cannula in the fluid delivery location, using the single hand to push the push feature while pulling the pull feature to urge the IV catheter system to move from the insertion configuration to the fluid delivery configuration, in which the needle is positioned outside the catheter hub.

The catheter hub may have a catheter hub intermediate portion between the catheter hub proximal end and the catheter hub distal end. The catheter component may further have an extension tubing junction extending outwardly from the catheter hub intermediate portion to connect the catheter hub to extension tubing. The push feature may be a push surface extending between the catheter hub intermediate portion and the extension tubing junction. The push surface may be oriented substantially perpendicular to the axis. Pushing the push feature may include pressing on the push surface.

The catheter component may further have a securement platform with a first wing extending from the catheter hub, generally parallel to the axis. Urging the IV catheter system to move from the insertion configuration to the fluid delivery configuration may include positioning the first wing to rest on skin of the patient.

In the insertion configuration, the first wing and the grip may be generally parallel to each other and may be positioned in abutting relation to each other. Urging the IV catheter system to move from the insertion configuration to the fluid delivery configuration may include causing the grip to slide along the first wing.

At least one of the first wing and the grip may have one or more alignment features. Urging the IV catheter system to move from the insertion configuration to the fluid delivery configuration may include, with the one or more alignment features, causing the first wing and the grip to remain positioned in abutting relation to each other during motion of the IV catheter system from the insertion configuration toward the fluid delivery configuration.

At least one of the first wing and the grip may have one or more locking features. Urging the IV catheter system to move from the insertion configuration to the fluid delivery configuration may include providing a disengagement force sufficient to unlock the one or more locking features.

The pull feature may be a leading edge of the grip. Pulling the pull feature may include pulling on the leading edge with the single hand.

In some embodiments, an IV catheter system may have an insertion configuration and a fluid delivery configuration. The IV catheter system may have a catheter component and a needle component. The catheter component may have a catheter hub with a catheter hub distal end, a catheter hub proximal end, and a catheter hub intermediate portion between the catheter hub proximal end and the catheter hub distal end. The catheter hub may be shaped to define a chamber extending between the catheter hub distal end and the catheter hub proximal end, and a needle port at the catheter hub proximal end that provides access to the chamber. The catheter component may also have a cannula extending distally from the catheter hub distal end, an extension tubing junction extending outwardly from the catheter hub intermediate portion to connect the catheter hub to extension tubing, a septum within the chamber, and a push feature protruding outwardly from the catheter hub. The needle component may have a needle hub with a needle hub distal end and a needle hub proximal end, a needle extending distally from the needle hub distal end along an axis, and a grip extending generally parallel to the axis. The grip may have a pull feature defined by a leading edge of the grip. In the insertion configuration, the needle may be positioned within the cannula, the needle may pass through the septum, and the needle hub distal end may be seated in the needle port. In the fluid delivery configuration, the needle may be positioned outside the catheter hub. The push feature may be positioned to receive first contact from a first digit of a hand of a user to urge the catheter hub distally. Further, the pull feature may be positioned to receive second contact from a second digit of the hand simultaneously with receipt of the first contact such that the first and second contacts cooperate to urge the IV catheter system to move from the insertion configuration to the fluid delivery configuration. The leading edge may be shaped and sized to comfortably receive the second contact. The septum may be configured to provide a sufficiently low resistance to withdrawal of the needle through the septum to enable the hand, alone, to move the IV catheter system from the insertion configuration to the fluid delivery configuration.

The push feature may have a push surface extending between the catheter hub intermediate portion and the extension tubing junction. The push surface may be oriented substantially perpendicular to the axis.

The catheter component may further have a securement platform with a first wing extending from the catheter hub, generally parallel to the axis such that, in the fluid delivery configuration, the first wing rests on skin of a patient receiving fluid through the IV catheter system. Further, the catheter component may have a second wing extending from the catheter hub, generally coplanar with the first wing such that, in the fluid delivery configuration, the second wing also rests on the skin. In the insertion configuration, the first wing and the grip may be generally parallel to each other and may be positioned in abutting relation to each other. During motion of the IV catheter system from the insertion configuration to the fluid delivery configuration, the grip may slide along the first wing.

In a first implementation of the invention, an IV catheter system is provided comprising an insertion configuration and a fluid delivery configuration, the IV catheter system comprising a catheter component comprising: a catheter hub comprising a catheter hub distal end and a catheter hub proximal end, wherein the catheter hub is shaped to define a chamber extending between the catheter hub distal end and the catheter hub proximal end, and a needle port at the catheter hub proximal end that provides access to the chamber; a cannula extending distally from the catheter hub distal end; and a push feature protruding outwardly from the catheter hub. The IV catheter system further comprises a needle component comprising: a needle hub comprising a needle hub distal end and a needle hub proximal end; a needle extending distally from the needle hub distal end along an axis; and a grip extending from the needle hub, generally parallel to the axis, the grip comprising a pull feature, wherein, in the insertion configuration, the needle is positioned within the cannula and the needle hub distal end is seated in the needle port, and wherein, in the fluid delivery configuration, the needle is positioned outside the catheter hub, and wherein the push feature is positioned to receive first contact from a first digit of a hand of a user to urge the catheter hub distally and the pull feature is positioned to receive second contact from a second digit of the hand simultaneously with receipt of the first contact such that the first and second contacts cooperate to urge the IV catheter system to move from the insertion configuration to the fluid delivery configuration.

In some instances, the catheter hub of the IV catheter system further comprises a catheter hub intermediate portion between the catheter hub proximal end and the catheter hub distal end, wherein the catheter component further comprises an extension tubing junction extending outwardly from the catheter hub intermediate portion to connect the catheter hub to extension tubing, wherein the push feature comprises a push surface extending between the catheter hub intermediate portion and the extension tubing junction, wherein the push surface is oriented substantially perpendicular to the axis.

In some instances, the grip of the IV catheter system further comprises a recess shaped to receive the extension tubing junction in the insertion configuration, wherein moving the IV catheter system from the insertion configuration to the fluid delivery configuration comprises rotating the needle component relative to the catheter component about the axis to withdraw the extension tubing junction from the recess.

In some instances, the catheter component of the IV catheter system further comprises a septum within the chamber, through which the needle passes in the insertion configuration, wherein the septum is configured to provide a sufficiently low resistance to withdrawal of the needle through the septum to enable the hand, alone, to move the IV catheter system from the insertion configuration to the fluid delivery configuration. In some instances, the catheter component further comprises a securement platform comprising a first wing extending from the catheter hub, generally parallel to the axis such that, in the fluid delivery configuration, the first wing rests on skin of a patient receiving fluid through the IV catheter system.

In some instances, the securement platform of the IV catheter system further comprises a second wing extending from the catheter hub, generally coplanar with the first wing such that, in the fluid delivery configuration, the second wing also rests on the skin.

In some instances, the first wing and the grip are generally parallel to each other and are positioned in abutting relation to each other in the insertion configuration of the IV catheter system, wherein, during motion of the IV catheter system from the insertion configuration to the fluid delivery configuration, the grip slides along the first wing.

In some instances, at least one of the first wing and the grip of the IV catheter system comprises one or more alignment features that cause the first wing and the grip to remain positioned in abutting relation to each other during motion of the IV catheter system from the insertion configuration toward the fluid delivery configuration. In some instances, at least one of the first wing and the grip comprises one or more locking features that cause the IV catheter system to remain in the insertion configuration until the first contact and the second contact cooperate to provide a disengagement force sufficient to unlock the one or more locking features.

In some instances, the pull feature of the IV catheter system comprises a leading edge of the grip, wherein the leading edge is shaped and sized to comfortably receive the second contact.

In a second implementation of the invention, a method is provided for preparing an IV catheter system to deliver fluid to a patient, the IV catheter system comprising an insertion configuration and a fluid delivery configuration, and the method comprising: 1) positioning the IV catheter system proximate a fluid delivery location of a patient, wherein the IV catheter system comprises a catheter component comprising: a catheter hub comprising a catheter hub distal end and a catheter hub proximal end, wherein the catheter hub is shaped to define a chamber extending between the catheter hub distal end and the catheter hub proximal end, and a needle port at the catheter hub proximal end that provides access to the chamber; a cannula extending distally from the catheter hub distal end; and a push feature protruding outwardly from the catheter hub; and a needle component comprising: a needle hub comprising a needle hub distal end and a needle hub proximal end; a needle extending distally from the needle hub distal end along an axis; and a grip extending from the needle hub, generally parallel to the axis, the grip comprising a pull feature; 2) with the IV catheter system in the insertion configuration, in which the needle is positioned within the cannula and the needle hub distal end is seated in the needle port, using a single hand to insert the needle and the cannula into the fluid delivery location; and 3) with the needle and cannula in the fluid delivery location, using the single hand to push the push feature while pulling the pull feature to urge the IV catheter system to move from the insertion configuration to the fluid delivery configuration, in which the needle is positioned outside the catheter hub.

In some instances, the catheter hub of the IV catheter system of the method comprises a catheter hub intermediate portion between the catheter hub proximal end and the catheter hub distal end, wherein the catheter component further comprises an extension tubing junction extending outwardly from the catheter hub intermediate portion to connect the catheter hub to extension tubing, wherein the push feature comprises a push surface extending between the catheter hub intermediate portion and the extension tubing junction, wherein the push surface is oriented substantially perpendicular to the axis, wherein pushing the push feature comprises pressing on the push surface.

In some instances, the catheter component of the IV catheter system of the method further comprises a securement platform comprising a first wing extending from the catheter hub, generally parallel to the axis, wherein urging the IV catheter system to move from the insertion configuration to the fluid delivery configuration comprises positioning the first wing to rest on skin of the patient.

In some instances, in the insertion configuration of the IV catheter system of the method, the first wing and the grip are generally parallel to each other and are positioned in abutting relation to each other, wherein urging the IV catheter system to move from the insertion configuration to the fluid delivery configuration comprises causing the grip to slide along the first wing. In some instances, at least one of the first wing and the grip comprises one or more alignment features, wherein urging the IV catheter system to move from the insertion configuration to the fluid delivery configuration comprises, with the one or more alignment features, causing the first wing and the grip to remain positioned in abutting relation to each other during motion of the IV catheter system from the insertion configuration toward the fluid delivery configuration.

In some instances, at least one of the first wing and the grip of the IV catheter system of the method comprises one or more locking features, wherein urging the IV catheter system to move from the insertion configuration to the fluid delivery configuration comprises providing a disengagement force sufficient to unlock the one or more locking features.

In some instances, the pull feature of the IV catheter system of the method further comprises a leading edge of the grip, wherein pulling the pull feature comprises pulling on the leading edge with the single hand.

In a third implementations of the invention, an IV catheter system is provided comprising an insertion configuration and a fluid delivery configuration, the IV catheter system comprising: a catheter component comprising: a catheter hub comprising a catheter hub distal end, a catheter hub proximal end, and a catheter hub intermediate portion between the catheter hub proximal end and the catheter hub distal end, wherein the catheter hub is shaped to define a chamber extending between the catheter hub distal end and the catheter hub proximal end, and a needle port at the catheter hub proximal end that provides access to the chamber; a cannula extending distally from the catheter hub distal end; an extension tubing junction extending outwardly from the catheter hub intermediate portion to connect the catheter hub to extension tubing; a septum within the chamber; and a push feature protruding outwardly from the catheter hub; and a needle component comprising: a needle hub comprising a needle hub distal end and a needle hub proximal end; a needle extending distally from the needle hub distal end along an axis; and a grip extending from the needle hub, generally parallel to the axis, the grip comprising a pull feature defined by a leading edge of the grip, wherein, in the insertion configuration, the needle is positioned within the cannula, the needle passes through the septum, and the needle hub distal end is seated in the needle port, wherein, in the fluid delivery configuration, the needle is positioned outside the catheter hub, wherein the push feature is positioned to receive first contact from a first digit of a hand of a user to urge the catheter hub distally and the pull feature is positioned to receive second contact from a second digit of the hand simultaneously with receipt of the first contact such that the first and second contacts cooperate to urge the IV catheter system to move from the insertion configuration to the fluid delivery configuration, wherein the leading edge is shaped and sized to comfortably receive the second contact, wherein the septum is configured to provide a sufficiently low resistance to withdrawal of the needle through the septum to enable the hand, alone, to move the IV catheter system from the insertion configuration to the fluid delivery configuration.

In some instances, the push feature of the IV catheter system further comprises a push surface extending between the catheter hub intermediate portion and the extension tubing junction, wherein the push surface is oriented substantially perpendicular to the axis. In some instances, the catheter component further comprises a securement platform comprising: a first wing extending from the catheter hub, generally parallel to the axis such that, in the fluid delivery configuration, the first wing rests on skin of a patient receiving fluid through the IV catheter system; and a second wing extending from the catheter hub, generally coplanar with the first wing such that, in the fluid delivery configuration, the second wing also rests on the skin, wherein, in the insertion configuration, the first wing and the grip are generally parallel to each other and are positioned in abutting relation to each other, wherein, during motion of the IV catheter system from the insertion configuration to the fluid delivery configuration, the grip slides along the first wing.

In some instances, the catheter hub of the IV catheter system further comprises a catheter hub intermediate portion between the catheter hub proximal end and the catheter hub distal end, wherein the catheter component further comprises an extension tubing junction extending outwardly from the catheter hub intermediate portion to connect the catheter hub to extension tubing, and wherein the first wing extends between the catheter hub intermediate portion and the extension tubing junction but does not extend outwardly beyond the extension tubing junction.

In some instances, the needle component of the IV catheter system further includes a flash component having a proximal vent and at least one side vent. In some instances, the catheter component includes a visual indicator. In some instances, the visual indicator is covered by the needle hub distal end when a tip of the needle extends distally beyond the cannula and that is exposed when the tip of the needle is withdrawn into the cannula.

In some instances, the needle component of the IV catheter system includes side grips and the catheter component includes a push tab. In some instances, the needle component includes a flash chamber, the side grips being formed on the flash chamber. In some instances, the catheter component further comprises: a securement platform comprising a first wing extending from the catheter hub, generally parallel to the axis such that, in the fluid delivery configuration, the first wing rests on skin of a patient receiving fluid through the IV catheter system; and an extension tubing junction extending outwardly from the catheter hub intermediate portion to connect the catheter hub to extension tubing, wherein the extension tubing junction extends in an opposite direction of the first wing.

In some instances, the catheter component of the IV catheter system further comprises a second wing that extends in the opposite direction of the first wing, the second wing incorporating but not extending beyond the extension tubing junction. In some instances, the second wing is formed of a rigid material and the first wing is formed of a flexible material. In some instances, the first wing is configured to pivot with respect to the catheter hub about the axis. In some instances, the first wing includes a hinge that enables the pivoting. In some instances, the first wing is formed of a flexible material that enables the pivoting.

In a fourth implementation of the invention, an IV catheter system is provided comprising: a catheter component comprising: a catheter hub comprising a catheter hub distal end and a catheter hub proximal end, wherein the catheter hub is shaped to define a chamber extending between the catheter hub distal end and the catheter hub proximal end, and a needle port at the catheter hub proximal end that provides access to the chamber; a cannula extending distally from the catheter hub distal end; and a push tab positioned at the catheter hub proximal end; and a needle component comprising: a needle hub comprising a needle hub distal end and a needle hub proximal end, the needle hub distal end including a cut-out that aligns with the push tab formed at the catheter hub proximal end; and a needle extending distally from the needle hub distal end along an axis.

In some instances, the catheter component of the IV catheter system includes a securement platform. In some instances, the push tab and the securement platform are connected via one or more connecting channels. In some instances, the catheter component includes a strain relief positioned at the catheter hub distal end around the cannula, the strain relief being coupled to the securement platform by a connecting channel. In some instances, the catheter component and the needle component each include a protrusion which interface to limit rotation of the needle component relative to the catheter component. In some instances, the needle component includes a wing and wherein the protrusions prevent the wing from rotating downward below the securement platform. In some instances, the IV catheter system further comprises a flash component that includes a path-defining structure for controlling flow of blood within the flash component.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1:
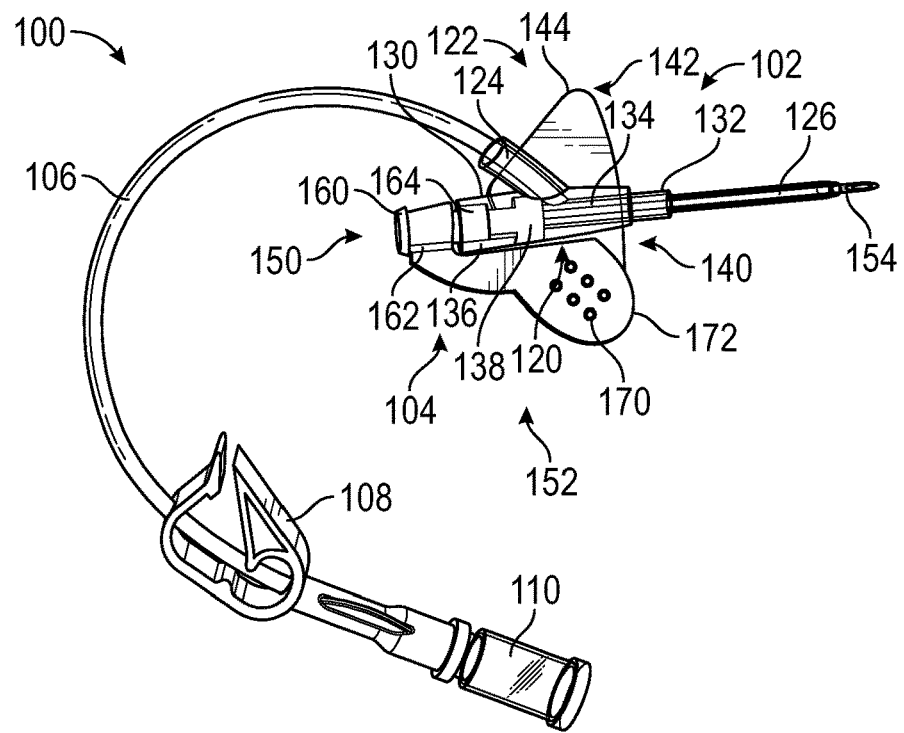
FIG. 1 is a perspective view of an IV catheter system according to one embodiment.

FIG. 1 is a perspective view of an IV catheter system 100 according to one embodiment. The IV catheter system 100 may be connected to a supply of fluid to be infused. The fluid supply (not shown) may include a bag of blood or medication to be delivered to the patient, a drip chamber that regulates flow of the fluid to the IV catheter system 100, and/or other components involved with the supply of fluid to the IV catheter system 100. The IV catheter system 100 may have a number of components, as shown in the exemplary embodiment of FIG. 1. These components may include a catheter component 102, a needle component 104, an extension tube 106, a clamp 108, and/or a luer lock adapter 110.

The catheter component 102 may be inserted into the fluid delivery location in the patient in order to convey the fluid to the patient. The needle component 104 may facilitate insertion of the catheter component 102 to the fluid delivery location. The extension tube 106 may convey the fluid to the catheter component 102. The clamp 108 may be used to manually block fluid flow to the catheter component 102 when it is desired to stop or pause fluid delivery. The luer lock adapter 110 may be readily connected to the fluid supply, for example, via connection to a complementary luer lock (not shown) of the fluid supply.

As embodied in FIG. 1, the IV catheter system 100 may be an integrated IV catheter system, as the extension tube 106 is pre-attached to the catheter component 102. In other embodiments, IV catheter systems of various open, integrated, and/or safety integrated configurations may be used.

The catheter component 102 may have various components, which may include a catheter hub 120, a securement platform 122, an extension tubing junction 124, and a cannula 126. The catheter hub 120 may have a generally tubular and/or hollow conical configuration, and may have a proximal end 130 and a distal end 132. The catheter hub 120 may be shaped to define a chamber 134 through which the fluid flows to reach the fluid delivery location. The catheter hub 120 may have a needle port 136 at the proximal end 130. The chamber 134 may contain a septum 138 that is designed to block flow of blood and/or the fluid to be delivered from the chamber 134 through the needle port 136. The cannula 126 may be secured to the distal end 132 of the catheter hub 120.

The securement platform 122 may have a generally planar configuration designed to permit the securement platform 122 to be secured to the skin of the patient, proximate the fluid delivery location, to keep the catheter component 102 securely in place as fluid delivery takes place. As embodied in FIG. 1, the securement platform 122 may have a first wing 140 with a generally planar shape, and a second wing 142 that also has a generally planar shape generally coplanar with the first wing 140. The second wing 142 may be positioned on the opposite side of the catheter hub 120 from the first wing 140. Thus, relative to the catheter hub 120, the first wing 140 and the second wing 142 may extend outward in opposite directions from the catheter hub 120. The first wing 140 and the second wing 142 may both be fixedly secured to the catheter hub 120, and may each have a generally triangular shape when viewed from along a direction perpendicular to the securement platform 122. In the alternative, the first wing 140 and/or the second wing 142 may have any shape, including but not limited to polygonal shapes such as triangular and rectangular shapes, and non-polygonal shapes such as circular, semicircular, oval, oblong, and irregular shapes. Some examples of these alternative shapes will be shown in subsequent embodiments. The first wing 140 and the second wing 142 may each have a trailing edge 144 oriented toward the proximal end 130 of the catheter hub 120.

The needle component 104 may have a needle hub 150, a grip 152, and a needle 154. The needle hub 150 may be detachably coupled to the catheter hub 120 of the catheter component 102. The grip 152 may extend outward from the needle hub 150. The needle 154 may be removably positioned within the cannula 126 such that the needle 154 facilitates the process of accessing the fluid delivery location (for example, a vein) and proper positioning of the cannula 126 to deliver the fluid to the fluid delivery location.

The needle hub 150 may have a generally tubular shape with a proximal end 160 and a distal end 162. The needle hub 150 may have a boss 164 positioned at the distal end 162; the boss 164 may be insertable into the needle port 136 of the catheter hub 120 of the catheter component 102.

The grip 152 may have a generally planar shape that extends outward from the needle hub 150. When viewed from a direction perpendicular to the grip 152, the grip 152 may have an oblong and/or partially elliptical shape. The grip 152, the first wing 140, and/or the second wing 142 may have one or more grip features 170, as shown on the grip 252, which may help provide a secure interface that facilitates gripping and/or moving the grip 152 by hand. The grip 152 may have a leading edge 172.

The IV catheter system 100 may have an insertion configuration, in which the IV catheter system 100 is readily insertable to position the cannula 126 in the fluid delivery location, and a fluid delivery configuration, in which the fluid flow through the cannula 126 is relatively unimpeded. In FIG. 1, the IV catheter system 100 is in the insertion configuration. The needle 154 is positioned within the cannula 126 to provide a sharpened tip for penetrating tissue and a relatively stiff body that supports the cannula 126 during insertion. The boss 164 of the needle hub 150 is positioned within the needle port 136 of the catheter hub 120. The needle 154 passes through the septum 138 of the catheter component 102.

The IV catheter system 100 may be inserted into position by positioning the tip of the cannula 126 proximate the fluid delivery location (for example, the patient's vein). The securement platform 122 may be placed on the patient's skin, proximate the fluid delivery location and/or held in the clinician's hand. The catheter component 102 and the needle component 104 may be advanced to push the cannula 126 until the tip of the cannula 126 penetrates the surrounding tissue and reaches the fluid delivery location. If desired, the catheter component 102 may be advanced by pushing a push surface of the catheter component 102. The "push surface" is a surface that is generally proximally-oriented, and thus can receive contact from the clinician's hand to urge the catheter component 102 and the needle component 104, together, distally.

Once the tip of the cannula 126 has reached the fluid delivery location, the IV catheter system 100 may be moved to the fluid delivery configuration. This may be done by withdrawing the needle component 104 proximally from the catheter component 102. This may initially cause the boss 164 to be withdrawn proximally from within the needle port 136. The needle 154 may also be withdrawn proximally from the cannula 126, and then through the chamber 134, including the septum 138. The needle 154 may pass out of the chamber 134 through the needle port 136, thus completing motion of the IV catheter system 100 to the fluid delivery configuration. Fluid flow to the fluid delivery location may now be accomplished by urging the fluid to flow through the extension tube 106, into the chamber 134, and through the cannula 126 to the fluid delivery location.

The IV catheter system 100 may advantageously be designed to facilitate insertion to the fluid delivery location to be readily performed with a single hand. For example, during insertion, the clinician may, with one hand, hold the catheter component 102 and the needle component 104, for example, by grasping the securement platform 122 and the grip 152. The clinician may then, with the same hand, apply gentle pressure to one or more push surfaces of the catheter component 102 (for example, the trailing edges 144 of the first wing 140 and/or the second wing 142) to urge the tip of the cannula 126 to penetrate the patient's skin and ultimately reach the fluid delivery location. If desired, one or more locking features (not shown) may be used to hold the catheter component 102 and the needle component 104 together until the clinician applies a threshold force to move the IV catheter system 100 from the insertion configuration to the fluid delivery configuration. Such locking features may take the form of interlocking features (not shown) between the boss 164 and the needle port 136, and/or the like.

The IV catheter system 100 may be designed to provide visual confirmation of proper placement in a blood vessel. For example, at least a portion of the catheter hub 120 may be translucent to provide visibility into the chamber 134. Thus, when the tip of the cannula 126 enters a vein, the resulting blood flow, or "flash," may be visible through the exterior wall of the catheter hub 120 as the blood enters the chamber 134. The extension tubing junction 124 and the extension tube 106 may also, optionally, be translucent. In some embodiments, the flash may extend through the extension tube 106 to the luer lock adapter 110. The luer lock adapter 110 may be coupled to the fluid supply in a manner that substantially prevents blood leakage.

Further, the IV catheter system 100 may advantageously be designed to facilitate motion from the insertion configuration to the fluid delivery configuration with a single hand. For example, the clinician may, with a single hand, which may be the same hand used to insert the IV catheter system 100 into the fluid delivery location, grasp the catheter component 102 and the needle component 104 and withdraw the needle component 104 proximally from the catheter component 102. The catheter component 102 may be left substantially in place so that only the needle component 104 moves significantly to move the IV catheter system 100 from the insertion configuration to the fluid delivery configuration.

This may be done by placing digits of the hand to contact the pull surface(s) of the needle component 104 and the push surface(s) of the catheter component 102, and then with those digits, pulling the needle component 104 proximally while pushing the catheter component 102 distally to keep it from moving proximally with the needle component 104. For example, the trailing edges 144 of the securement platform 122 may act as push surfaces, while the edge 172 of the grip 152 may act as a pull surface. The clinician may place one or more fingers on the leading edge 172 of the grip 152 and pulling proximally, while pushing with a thumb and/or one or more other fingers on the trailing edges 144 of the securement platform 122. Thus, the catheter component 102 may be kept in place with the tip of the cannula 126 at the fluid delivery location while the needle component 104 is withdrawn proximally from the catheter component 102 to unblock the fluid delivery path to the fluid delivery location.

The relative positions of the pull and push surfaces may facilitate single-handed operation in the manner described above. If desired, the coupling of the needle hub 150 with the catheter hub 120 may be such that the needle hub 150 is rotatable relative to the catheter hub 120 while the IV catheter system 100 is in the insertion configuration. Thus, the clinician may, with the hand, rotate the grip 152 to an orientation that is most comfortable for pulling on the leading edge 172, prior to pulling on the leading edge 172 and pushing on the trailing edges 144.

The septum 138 may have a "low friction" or "low drag" design configured to provide relatively low resistance to withdrawal of the needle 154 proximally through the septum 138, which occurs as the IV catheter system 100 transitions from the insertion configuration to the fluid delivery configuration. The resistance to withdrawal of the needle 154 through the septum 138 may be sufficiently low that the clinician can relatively easily move the IV catheter system 100 from the insertion configuration to the fluid delivery configuration with only a single hand. In some embodiments, the resistance to withdrawal may be, on average, less than about 50 gf.

Figure 2:
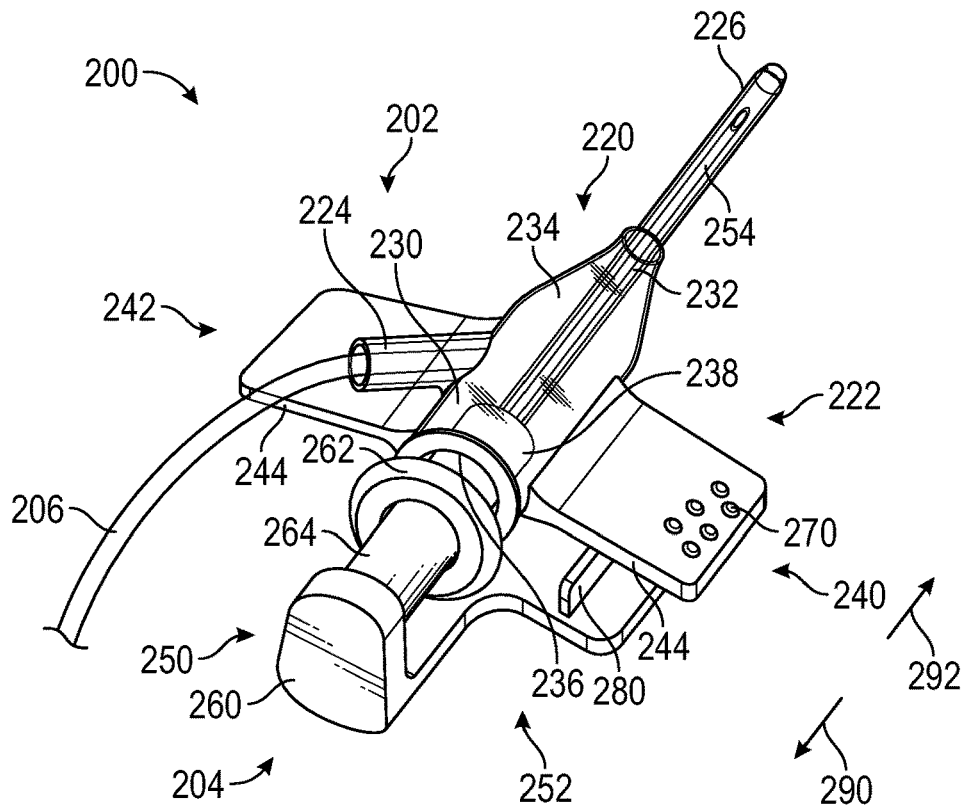
FIG. 2 is a perspective view of a portion of an IV catheter system according to one alternative embodiment.

FIG. 2 is a perspective view of a portion of an IV catheter system 200 according to one alternative embodiment. The IV catheter system 200 may have components that generally correspond to those of the IV catheter system 100 of FIG. 1. FIG. 2 illustrates only a catheter component 202, a needle component 204, and the distal end of an extension tube 206 connected to the catheter component 202. The IV catheter system 200 may have a configuration similar to that of the IV catheter system 100 of FIG. 1; however, some components may be shaped differently to provide alternative ergonomics.

The catheter component 202 may have a catheter hub 220, a securement platform 222, an extension tubing junction 224, and a cannula 226. The catheter hub 220 may have a generally tubular and/or hollow conical shape, with a proximal end 230 and a distal end 232. The catheter hub 220 may have a generally translucent exterior wall shaped to define a chamber 234 through which fluid flows to reach the fluid delivery location through the cannula 226. The catheter hub 220 may have a needle port 236 that connects to the needle component 204, proximate the proximal end 230 of the catheter hub 220. The catheter hub 220 may also have a septum 238 positioned within the chamber 234. The septum 238 may be a "low drag" septum as described previously.

The securement platform 222 may be attached to the skin of the patient during fluid delivery to keep the cannula 226 in place at the fluid delivery location. The securement platform 222 may have a first wing 240 and a second wing 242, which may both be generally planar in shape, and may extend in opposite directions relative to the catheter hub 220. Each of the first wing 240 and the second wing 242 may have a generally rectangular shape when viewed from perpendicular to the securement platform 222, with a trailing edge 244 that can act as a push surface.

The needle component 204 may have a needle hub 250, a grip 252, and a needle 254. The needle hub 250 may have a generally cylindrical shape with a proximal end 260 and a distal end 262. The needle hub 250 may also have a boss 264 that protrudes from the distal end 262 to interface with the needle port 236 of the catheter hub 220.

The grip 252 may have a generally planar shape, with a generally rectangular shape when viewed from perpendicular to the grip 252. However, the grip 252 may have any other suitable shape. The grip 252 may have a leading edge (not visible), which may serve as a pull surface. The grip 252, the first wing 240, and/or the second wing 242 may have one or more grip features 270, which may help provide a secure interface that facilitates gripping and/or moving the grip 152 by hand.

To move the IV catheter system 200 from the insertion configuration to the fluid delivery configuration, the clinician may position a digit (for example, a finger) on the leading edge of the grip 252, and a digit (for example, a finger or thumb) on the trailing edge 244 of the first wing 240 and/or the second wing 242. The clinician may then pull the leading edge proximally, as indicated by the arrow 290, and may push the trailing edge 244 of the first wing 240 and/or the second wing 242 distally, as indicated by the arrow 292. This may cause the catheter component 202 to remain in place while the needle component 204 is withdrawn proximally from the catheter component 202.

The grip 252 and the first wing 240 may be positioned parallel to each other, and may be positioned in close proximity to each other such that they are in abutting relation to each other in the insertion configuration, and during the initial stages of motion from the insertion configuration to the fluid delivery configuration. In order to maintain the desired relative positioning between the grip 252 and the first wing 240, the grip 252 and/or the first wing 240 may have one or more alignment features that maintain relative positioning and/or orientation between the first wing 240 and the grip 252.

Specifically, the grip 252 may have an alignment feature in the form of an alignment ridge 280, which may protrude toward the first wing 240, and may be received in a complementary alignment feature (not shown) such as a trough or other feature on the surface of the first wing 240 that faces toward the grip 252. The alignment ridge 280 and the complementary alignment feature may help keep the needle 254 parallel to the cannula 226 during motion of the IV catheter system 200 to the fluid delivery configuration. This may help ensure that the needle component 204 can be smoothly withdrawn from the catheter component 202. More specifically, application of imbalanced force on the catheter component 202 and/or the needle component 204 may urge the needle component 204 to rotate relative to the catheter component 202. For example, if the clinician is pulling on the leading edge of the grip 252 while pushing on the trailing edge 244 of the first wing 240, this may urge the needle component 204 to rotate clockwise, relative to the view of FIG. 2, with respect to the catheter component 202.

The alignment ridge 280 and the complementary alignment feature of the first wing 240 may help ensure that such relative rotation does not occur until the needle component 204 has been withdrawn from the catheter component 202 sufficiently to detach the alignment ridge 280 from the complementary alignment feature of the first wing 240. Thus, binding and/or other undesired interactions between the catheter component 202 and the needle component 204 may be avoided during motion from the insertion configuration to the fluid delivery configuration.

Figure 3A:
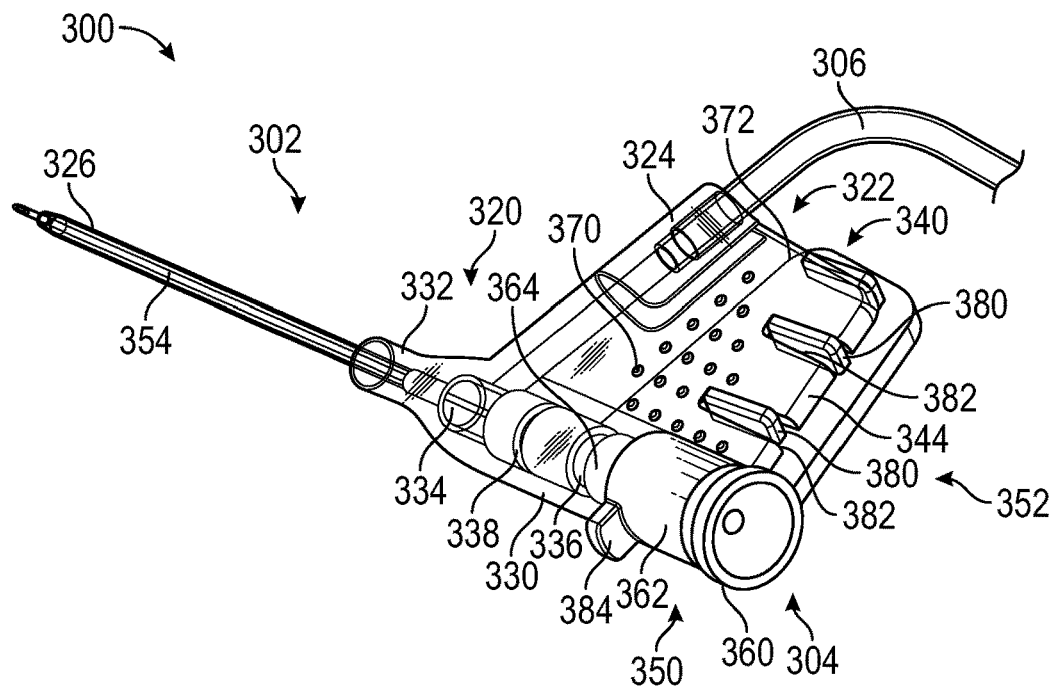
FIGS. 3A and 3B are perspective and plan views, respectively, of a portion of an IV catheter system according to another alternative embodiment.
Figure 3B:
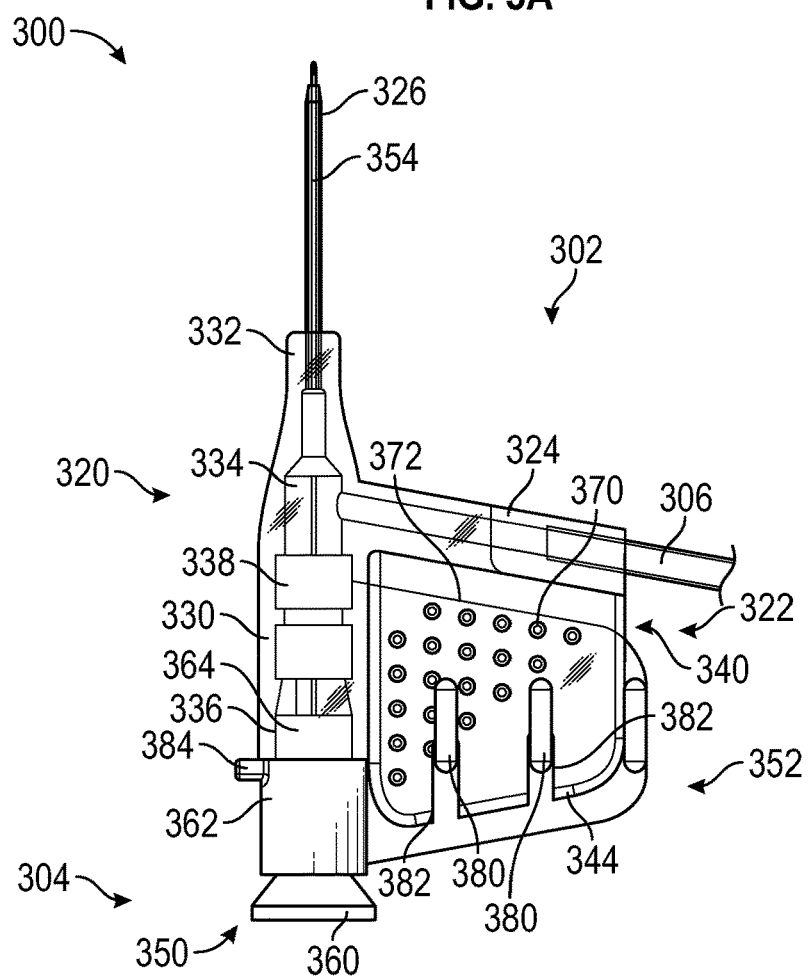

FIGS. 3A and 3B are perspective and plan views, respectively, of a portion of an IV catheter system 300 according to another alternative embodiment. The IV catheter system 300 may have components that generally correspond to those of FIGS. 1 and 2. FIGS. 3A and 3B illustrate only a catheter component 302, a needle component 304, and the distal end of an extension tube 306 connected to the catheter component 302. The IV catheter system 300 may have a configuration similar to those of previous embodiments; however, some components may be shaped differently to provide alternative ergonomics.

As in previous embodiments, the catheter component 302 may have a catheter hub 320, a securement platform 322, an extension tubing junction 324, and a cannula 326. The catheter hub 320 may have a generally tubular and/or hollow conical shape, with a proximal end 330 and a distal end 332. The catheter hub 320 may have a generally translucent exterior wall shaped to define a chamber 334 through which fluid flows to reach the fluid delivery location through the cannula 326. The catheter hub 320 may have a needle port 336 that connects to the needle component 304, proximate the proximal end 330 of the catheter hub 320. The catheter hub 320 may also have a septum 338 positioned within the chamber 334. The septum 338 may be a "low drag" septum as described previously.

The securement platform 322 may be attached to the skin of the patient during fluid delivery to keep the cannula 326 in place at the fluid delivery location. The securement platform 322 may have only a single wing in the form of a first wing 340, which may be generally planar in shape, and may have a generally trapezoidal shape when viewed from perpendicular to the securement platform 322, with a trailing edge 344 that can act as a push surface.

The first wing 340 may be integrated with the extension tubing junction 324 such that the extension tubing junction 324 defines a leading edge of the first wing 340. The extension tubing junction 324 may provide an enlargement to the width of the first wing 340 at the leading edge; this enlargement may enable the extension tubing junction 324 to serve as a push surface. More specifically, the clinician may push on the trailing portion of the extension tubing junction 324, where the extension tubing junction 324 merges with the first wing 340, to urge the catheter component 302 forward.

The needle component 304 may have a needle hub 350, a grip 352, and a needle 354. The needle hub 350 may have a generally cylindrical shape with a proximal end 360 and a distal end 362. The needle hub 350 may also have a boss 364 that protrudes from the distal end 362 to interface with the needle port 336 of the catheter hub 320.

The grip 352 may have a generally planar shape, with a generally trapezoidal shape when viewed from perpendicular to the grip 352. The grip 352 may have a leading edge 372, which may serve as a pull surface. The grip 352 and/or the first wing 340 may have one or more grip features 370, which may help provide a secure interface that facilitates gripping and/or moving the grip 152 by hand.

To move the IV catheter system 300 from the insertion configuration to the fluid delivery configuration, the clinician may position a digit (for example, a finger) on the leading edge 372 of the grip 352 and/or on the leading edge of the tab 384, and a digit (for example, a finger or thumb) on the trailing edge 344 of the first wing 340. The clinician may then pull the leading edge 372 and/or the leading edge of the tab 384 proximally, and may push the trailing edge 344 of the first wing 340 distally. This may cause the catheter component 302 to remain in place while the needle component 304 is withdrawn proximally from the catheter component 302.

The grip 352 and the first wing 340 may be positioned parallel to each other, and may be positioned in close proximity to each other such that they are in abutting relation to each other in the insertion configuration, and during the initial stages of motion from the insertion configuration to the fluid delivery configuration. In order to maintain the desired relative positioning between the grip 352 and the first wing 340, the grip 352 and/or the first wing 340 may have one or more alignment features that maintain relative positioning and/or orientation between the first wing 340 and the grip 352.

Specifically, the grip 352 may have an alignment feature in the form of a pair of alignment ridges 380, which may protrude toward the first wing 340, and may be received in complementary alignment features in the form of slots 382 formed in the first wing 340. The alignment ridges 380 and the slots 382 may help keep the needle component 304 parallel to the catheter component 302 during motion of the IV catheter system 300 to the fluid delivery configuration, which may facilitate motion to the fluid delivery configuration as described in the previous embodiment.

If desired, the first wing 340 may be translucent so as to facilitate user visualization of the grip 352, and more specifically, of the edge 372. In addition to the leading edge 372, the needle component 304 may have a tab 384 that protrudes outward from the needle hub 350 in a direction generally opposite to that in which the grip 352 protrudes. The tab 384 may provide a pull surface that can be used by a clinician, in addition to and/or in the alternative to the leading edge 372 of the grip 352. This may provide additional options for the clinician to insert the IV catheter system 300 with a single hand and/or to move the IV catheter system 300 from the insertion configuration to the fluid delivery configuration with a single hand.

Figures 4, 5:
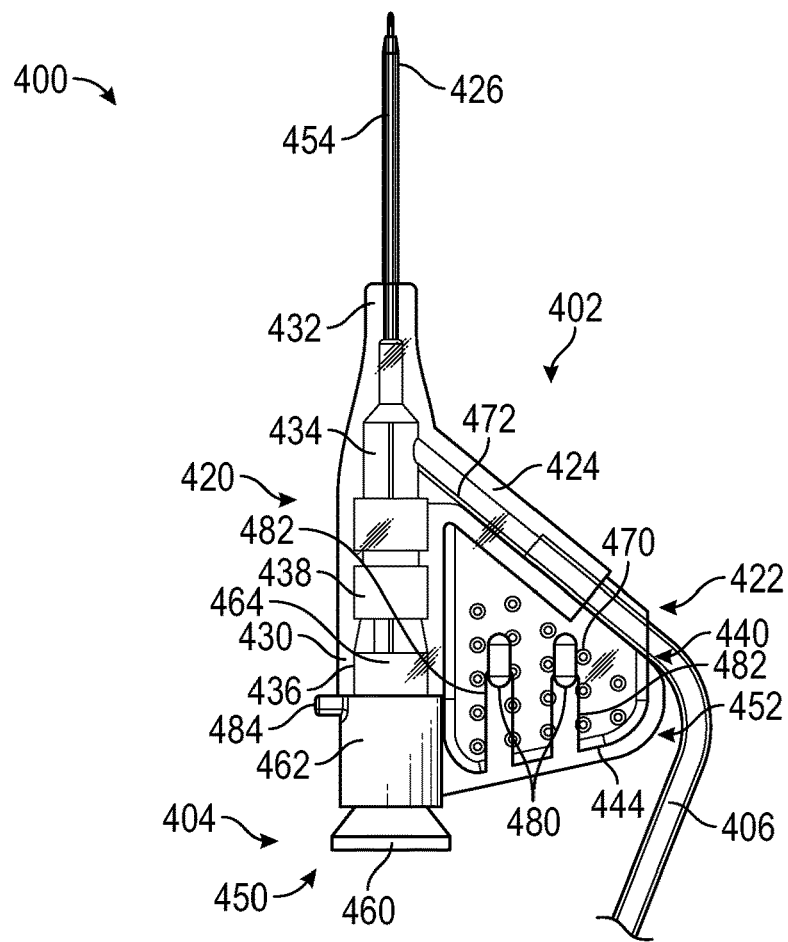
FIG. 4 is a plan view of an IV catheter system according to another alternative embodiment.
FIG. 5 is a perspective view of an IV catheter system according to another alternative embodiment.

FIG. 4 is a plan view of an IV catheter system 400 according to another alternative embodiment. The IV catheter system 400 may have components similar to those of the IV catheter system 300 of FIGS. 3A and 3B. FIG. 4 illustrates only a catheter component 402, a needle component 404, and the distal end of an extension tube 406 connected to the catheter component 402. The IV catheter system 400 may have a configuration similar to that of the IV catheter system 300; however, some components may be shaped differently to provide alternative ergonomics.

As in previous embodiments, the catheter component 402 may have a catheter hub 420, a securement platform 422, an extension tubing junction 424, and a cannula 426. The catheter hub 420 may have a generally tubular and/or hollow conical shape, with a proximal end 430 and a distal end 432. The catheter hub 420 may have a generally translucent exterior wall shaped to define a chamber 434 through which fluid flows to reach the fluid delivery location through the cannula 426. The catheter hub 420 may have a needle port 436 that connects to the needle component 404, proximate the proximal end 430 of the catheter hub 420. The catheter hub 420 may also have a septum 438 positioned within the chamber 434. The septum 438 may be a "low drag" septum as described previously.

The securement platform 422 may be attached to the skin of the patient during fluid delivery to keep the cannula 426 in place at the fluid delivery location. The securement platform 422 may have only a single wing in the form of a first wing 440, which may be generally planar in shape, and may have a generally triangular shape when viewed from perpendicular to the securement platform 422, with a trailing edge 444 that can act as a push surface.

The first wing 440 may be integrated with the extension tubing junction 424 such that the extension tubing junction 424 defines a leading edge of the first wing 440. The extension tubing junction 424 may provide an enlargement to the width of the first wing 440 at the leading edge; this enlargement may enable the extension tubing junction 424 to serve as a push surface. More specifically, the clinician may push on the trailing portion of the extension tubing junction 424, where the extension tubing junction 424 merges with the first wing 440, to urge the catheter component 402 forward.

The needle component 404 may have a needle hub 450, a grip 452, and a needle 454. The needle hub 450 may have a generally cylindrical shape with a proximal end 460 and a distal end 462. The needle hub 450 may also have a boss 464 that protrudes from the distal end 462 to interface with the needle port 436 of the catheter hub 420.

The grip 452 may have a generally planar shape, with a generally triangular shape when viewed from perpendicular to the grip 452. The grip 452 may have a leading edge 472, which may serve as a pull surface. The grip 452 and/or the first wing 440 may have one or more grip features 470, which may help provide a secure interface that facilitates gripping and/or moving the grip 452 by hand.

To move the IV catheter system 400 from the insertion configuration to the fluid delivery configuration, the clinician may position a digit (for example, a finger) on the leading edge 472 of the grip 452 and/or the leading edge of the tab 484, and a digit (for example, a finger or thumb) on the trailing edge 444 of the first wing 440. The clinician may then pull the leading edge 472 and/or the leading edge of the tab 484 proximally, and may push the trailing edge 444 of the first wing 440 distally. This may cause the catheter component 402 to remain in place while the needle component 404 is withdrawn proximally from the catheter component 402.

The grip 452 and the first wing 440 may be positioned parallel to each other, and may be positioned in close proximity to each other such that they are in abutting relation to each other in the insertion configuration, and during the initial stages of motion from the insertion configuration to the fluid delivery configuration. In order to maintain the desired relative positioning between the grip 452 and the first wing 440, the grip 452 and/or the first wing 440 may have one or more alignment features that maintain relative positioning and/or orientation between the first wing 440 and the grip 452.

Specifically, the grip 452 may have an alignment feature in the form of a pair of alignment ridges 480, which may protrude toward the first wing 440, and may be received in complementary alignment features in the form of slots 482 formed in the first wing 440. The alignment ridges 480 and the slots 482 may help keep the needle component 404 parallel to the catheter component 402 during motion of the IV catheter system 400 to the fluid delivery configuration, which may facilitate motion to the fluid delivery configuration as described in the previous embodiment.

If desired, the first wing 440 may be translucent so as to facilitate user visualization of the grip 452, and more specifically, of the edge 472. In addition to the leading edge 472, the needle component 404 may have a tab 484 that protrudes outward from the needle hub 450 in a direction generally opposite to that in which the grip 452 protrudes. The tab 484 may provide a pull surface that can be used by a clinician, in addition to and/or in the alternative to the leading edge 472 of the grip 452. This may provide additional options for the clinician to insert the IV catheter system 400 with a single hand and/or to move the IV catheter system 400 from the insertion configuration to the fluid delivery configuration with a single hand.

By comparison with the IV catheter system 300 of FIGS. 3A and 3B, the first wing 440 and the grip 452 may have a more triangular, swept shape, as shown. This different shape may cause the leading edge 472 of the grip 452 to be positioned at a different angle and/or position, which may facilitate single-handed operation for some users. Further, in the IV catheter system 400 of FIG. 4, the alignment ridges 480 may be relatively short, thereby providing low frictional resistance to motion of the IV catheter system 400 from the insertion configuration to the fluid delivery configuration.

FIG. 5 is a perspective view of an IV catheter system 500 according to another alternative embodiment. The IV catheter system 500 may have components similar to those of the IV catheter systems of previous embodiments. FIG. 5 illustrates only a catheter component 502, a needle component 504, and the distal end of an extension tube 506 connected to the catheter component 502.

As in previous embodiments, the catheter component 502 may have a catheter hub 520, a securement platform 522, an extension tubing junction 524, and a cannula 526. The catheter hub 520 may have a generally tubular and/or hollow conical shape, with a proximal end 530 and a distal end 532. The catheter hub 520 may have a generally translucent exterior wall shaped to define a chamber 534 through which fluid flows to reach the fluid delivery location through the cannula 526. The catheter hub 520 may have a needle port 536 that connects to the needle component 504, proximate the proximal end 530 of the catheter hub 520. The catheter hub 520 may also have a septum 538 positioned within the chamber 534. The septum 538 may be a "low drag" septum as described previously.

The securement platform 522 may be attached to the skin of the patient during fluid delivery to keep the cannula 526 in place at the fluid delivery location. The securement platform 522 may have a first wing 540 and a second wing 542, each of which may be generally planar in shape. The first wing 540 and the second wing 542 may each have a generally trapezoidal shape when viewed from perpendicular to the securement platform 522, with a trailing edge 544 that can act as a push surface.

The first wing 540 may be integrated with the extension tubing junction 524 such that the extension tubing junction 524 defines a leading edge of the first wing 540. The extension tubing junction 524 may provide an enlargement to the width of the first wing 540 at the leading edge; this enlargement may enable the extension tubing junction 524 to serve as a push surface. More specifically, the clinician may push on the trailing portion of the extension tubing junction 524, where the extension tubing junction 524 merges with the first wing 540, to urge the catheter component 502 forward.

The second wing 542 may be rotatably coupled to the catheter hub 520. Thus, the clinician may position the second wing 542 at substantially any orientation about the axis defined by the cannula 526 and/or the needle 554. The second wing 542 may rotate relatively freely about the catheter hub 520 such that the clinician can rotate the second wing 542, relative to the first wing 540, with a single hand to obtain the desired grip prior to and/or during insertion of the IV catheter system 500 into the fluid delivery location and/or motion of the IV catheter system 500 from the insertion configuration to the fluid delivery configuration.

The needle component 504 may have a needle hub 550, a grip 552, and a needle 554. The needle hub 550 may have a generally cylindrical shape with a proximal end 560 and a distal end 562. The needle hub 550 may also have a boss 564 that protrudes from the distal end 562 to interface with the needle port 536 of the catheter hub 520.

The grip 552 may have a generally planar shape, with a generally trapezoidal shape when viewed from perpendicular to the grip 552. The grip 552 may have a leading edge 572, which may serve as a pull surface. The grip 552 and/or the first wing 540 may have one or more grip features 570, which may help provide a secure interface that facilitates gripping and/or moving the grip 552 by hand.

The grip 552 and the first wing 540 may be positioned parallel to each other, and may be positioned in close proximity to each other such that they are in abutting relation to each other in the insertion configuration, and during the initial stages of motion from the insertion configuration to the fluid delivery configuration. In order to maintain the desired relative positioning between the grip 552 and the first wing 540, the grip 552 and/or the first wing 540 may have one or more alignment features that maintain relative positioning and/or orientation between the first wing 540 and the grip 552.

Specifically, the grip 552 may have an alignment feature in the form of a pair of alignment ridges 580, which may protrude toward the first wing 540, and may be received in complementary alignment features in the form of slots 582 formed in the first wing 540. The alignment ridges 580 and the slots 582 may help keep the needle component 504 parallel to the catheter component 502 during motion of the IV catheter system 500 to the fluid delivery configuration, which may facilitate motion to the fluid delivery configuration as described in the previous embodiment.

If desired, the first wing 540 and/or the second wing 542 may be translucent so as to facilitate user visualization of the grip 552, and more specifically, of the edge 572. In addition to the leading edge 572, the needle component 504 may have a tab 584 that protrudes outward from the needle hub 550 in a direction generally opposite to that in which the grip 552 protrudes. The tab 584 may provide a pull surface that can be used by a clinician, in addition to and/or in the alternative to the leading edge 572 of the grip 552. This may provide additional options for the clinician to insert the IV catheter system 500 with a single hand and/or to move the IV catheter system 500 from the insertion configuration to the fluid delivery configuration with a single hand.

To move the IV catheter system 500 from the insertion configuration to the fluid delivery configuration, the clinician may position a digit (for example, a finger) on the leading edge 572 of the grip 552 and/or the leading edge of the tab 584, and a digit (for example, a finger or thumb) on the trailing edge 544 of the first wing 540. The clinician may then pull the leading edge 572 and/or the leading edge of the tab 484 proximally, and may push the trailing edge 544 of the first wing 540 distally. This may cause the catheter component 502 to remain in place while the needle component 504 is withdrawn proximally from the catheter component 502.

Figure 6:
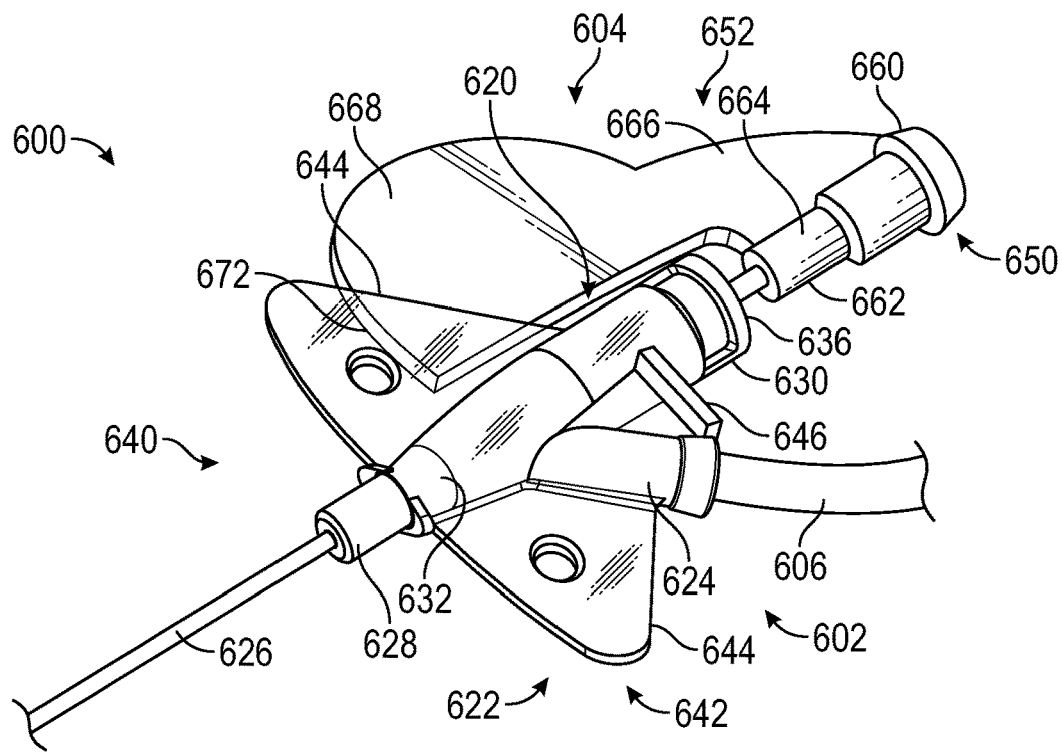
FIG. 6 is a perspective view of an IV catheter system according to another alternative embodiment.

FIG. 6 is a perspective view of an IV catheter system 600 according to another alternative embodiment. The IV catheter system 600 may have components similar to those of the IV catheter systems of previous embodiments. FIG. 6 illustrates only a catheter component 602, a needle component 604, and the distal end of an extension tube 606 connected to the catheter component 602.

As in previous embodiments, the catheter component 602 may have a catheter hub 620, a securement platform 622, an extension tubing junction 624, and a cannula 626. The catheter hub 620 may have a generally tubular and/or hollow conical shape, with a proximal end 630 and a distal end 632. The catheter hub 620 may have a generally translucent exterior wall shaped to define a chamber (not visible) through which fluid flows to reach the fluid delivery location through the cannula 626. The catheter hub 620 may have a needle port 636 that connects to the needle component 604, proximate the proximal end 630 of the catheter hub 620. The catheter hub 620 may also have a septum (not visible) positioned within the chamber. The septum may be a "low drag" septum as described previously. Further, the catheter hub 620 may have a kink resistance feature that helps to avoid kinking of the cannula 626 during insertion and/or infusion. The kink resistance feature may take the form of a proximal extension 628 on the distal end 632 of the catheter hub 620. The proximal extension 628 may receive the cannula 626, and may provide some resistance to bending of the cannula 626 at the juncture of the cannula 626 to the proximal end 630 to relieve the bending strain at that location, thereby helping avoid kinking or other undesired bending of the cannula 626.

The securement platform 622 may be attached to the skin of the patient during fluid delivery to keep the cannula 626 in place at the fluid delivery location. The securement platform 622 may have a first wing 640 and a second wing 642, each of which may be generally planar in shape. The first wing 640 and the second wing 642 may each have a generally triangular shape when viewed from perpendicular to the securement platform 622, with a trailing edge 644 that can act as a push surface. The first wing 640 and the second wing 642 may extend in opposite directions, outward from the axis of the catheter hub 620.

The second wing 642 may be integrated with the extension tubing junction 624 such that the extension tubing junction 624 passes through the trailing edge 644 of the second wing 642. The extension tubing junction 624 may provide an enlargement to the width of the second wing 642 proximate the trailing edge 644; this enlargement may enable the extension tubing junction 624 to serve as a push surface. Further, the catheter component 602 may have a push feature in the form of a push surface 646 that extends between the extension tubing junction 624 and the intermediate portion of the catheter hub 620, between the proximal end 630 and the distal end 632. The push surface 646 may have a size selected to enable the clinician to relatively easily push on the push surface 646 with a digit to urge the catheter component 602 forward. The push surface 646 may be oriented substantially perpendicular to the axis of the catheter component 602 and the needle component 604.

The needle component 604 may have a needle hub 650, a grip 652, and a needle (not visible). The needle hub 650 may have a generally cylindrical shape with a proximal end 660 and a distal end 662. The needle hub 650 may also have a boss 664 that protrudes from the distal end 662 to interface with the needle port 636 of the catheter hub 620.

The grip 652 may have a generally planar shape, with a generally irregular shape when viewed from perpendicular to the grip 652. The grip 652 may have a narrow portion 666 that extends from the needle hub 650 to connect to a larger portion 668 that lies in abutting relation to the first wing 640 of the securement platform 622 when the IV catheter system 600 is in the insertion configuration. The grip 652 may have a leading edge 672, which may serve as a pull surface. The grip 652 and/or the first wing 640 may have one or more grip features (not shown), which may help provide a secure interface that facilitates gripping and/or moving the grip 652 by hand.

To move the IV catheter system 600 from the insertion configuration to the fluid delivery configuration, the clinician may position a digit (for example, a finger) on the leading edge 672 of the grip 652, and a digit (for example, a finger or thumb) on the trailing edge 644 of the first wing 640 and/or the push surface 646. The clinician may then pull the leading edge 672 proximally, and may push the trailing edge 644 and/or the push surface 646 distally. This may cause the catheter component 602 to remain in place while the needle component 604 is withdrawn proximally from the catheter component 602.

Figure 7:
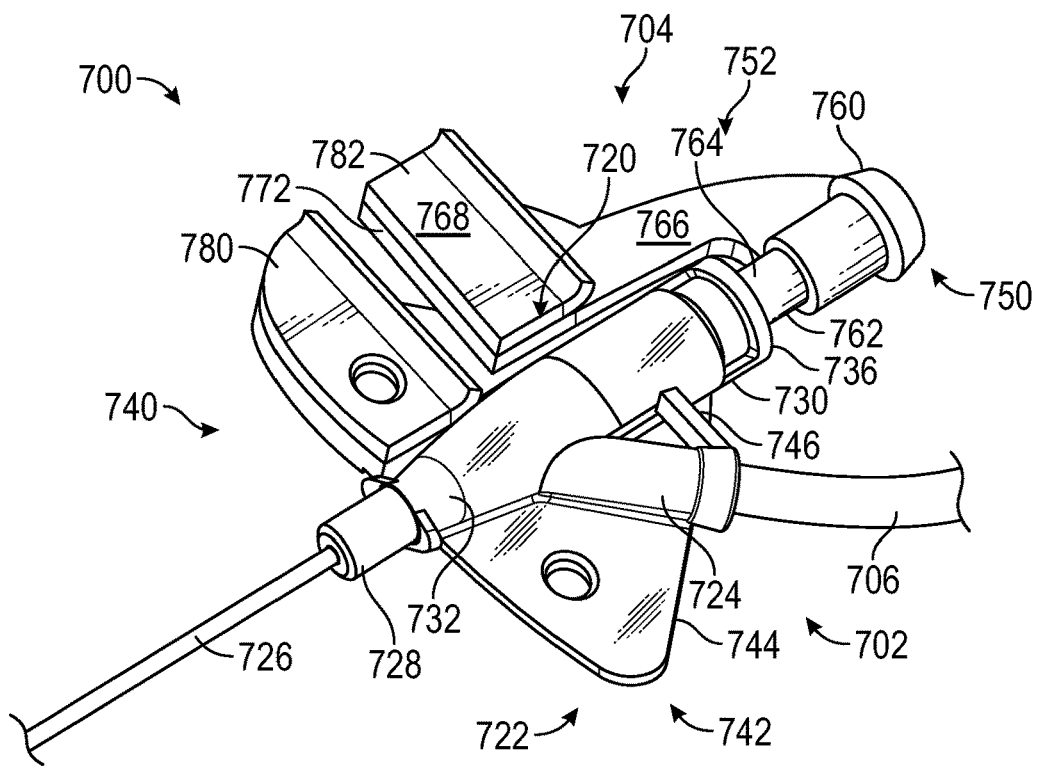
FIG. 7 is a perspective view of an IV catheter system according to another alternative embodiment.

FIG. 7 is a perspective view of an IV catheter system 700 according to another alternative embodiment. The IV catheter system 700 may have components similar to those of the IV catheter systems of previous embodiments. FIG. 7 illustrates only a catheter component 702, a needle component 704, and the distal end of an extension tube 706 connected to the catheter component 702.

As in previous embodiments, the catheter component 702 may have a catheter hub 720, a securement platform 722, an extension tubing junction 724, and a cannula 726. The catheter hub 720 may have a generally tubular and/or hollow conical shape, with a proximal end 730 and a distal end 732. The catheter hub 720 may have a generally translucent exterior wall shaped to define a chamber (not visible) through which fluid flows to reach the fluid delivery location through the cannula 726. The catheter hub 720 may have a needle port 736 that connects to the needle component 704, proximate the proximal end 730 of the catheter hub 720. The catheter hub 720 may also have a septum (not visible) positioned within the chamber. The septum may be a "low drag" septum as described previously. Further, the catheter hub 720 may have a kink resistance feature that helps to avoid kinking of the cannula 726 during insertion and/or infusion. The kink resistance feature may take the form of a proximal extension 728 on the distal end 732 of the catheter hub 720. The proximal extension 728 may receive the cannula 726, and may provide some resistance to bending of the cannula 726 at the juncture of the cannula 726 to the proximal end 730 to relieve the bending strain at that location, thereby helping avoid kinking or other undesired bending of the cannula 726.

The securement platform 722 may be attached to the skin of the patient during fluid delivery to keep the cannula 726 in place at the fluid delivery location. The securement platform 722 may have a first wing 740 and a second wing 742, each of which may be generally planar in shape. The first wing 740 and the second wing 742 may each have a generally triangular shape when viewed from perpendicular to the securement platform 722, with a trailing edge 744 that can act as a push surface. The first wing 740 and the second wing 742 may extend in opposite directions, outward from the axis of the catheter hub 720.

The second wing 742 may be integrated with the extension tubing junction 724 such that the extension tubing junction 724 passes through the trailing edge 744 of the second wing 742. The extension tubing junction 724 may provide an enlargement to the width of the second wing 742 proximate the trailing edge 744; this enlargement may enable the extension tubing junction 724 to serve as a push surface. Further, the catheter component 702 may have a push feature in the form of a push surface 746 that extends between the extension tubing junction 724 and the intermediate portion of the catheter hub 720, between the proximal end 730 and the distal end 732. The push surface 746 may have a size selected to enable the clinician to relatively easily push on the push surface 746 with a digit to urge the catheter component 702 forward. The push surface 746 may be oriented substantially perpendicular to the axis of the catheter component 702 and the needle component 704.

The needle component 704 may have a needle hub 750, a grip 752, and a needle (not visible). The needle hub 750 may have a generally cylindrical shape with a proximal end 760 and a distal end 762. The needle hub 750 may also have a boss 764 that protrudes from the distal end 762 to interface with the needle port 736 of the catheter hub 720.

The grip 752 may have a generally planar shape, with a generally irregular shape when viewed from perpendicular to the grip 752. The grip 752 may have a narrow portion 766 that extends from the needle hub 750 to connect to a larger portion 768 that lies in abutting relation to the first wing 740 of the securement platform 722 when the IV catheter system 700 is in the insertion configuration. The grip 752 may have a leading edge 772, which may serve as a pull surface. The grip 752 and/or the first wing 740 may have one or more grip features (not shown), which may help provide a secure interface that facilitates gripping and/or moving the grip 752 by hand.

The first wing 740 and/or the grip 752 may have one or more locking features that help to keep the IV catheter system 700 in the insertion configuration until the clinician applies a threshold disengagement force sufficient to detach the needle component 704 from the catheter component 702. As shown, the locking features may include a locking tab 780 on the first wing 740 and a locking tab 782 on the grip 752. In the insertion configuration, the locking tab 780 of the first wing 740 may overhang the locking tab 782 of the 752. The locking tab 780 and the locking tab 782 may be interlocked in the insertion configuration such that one or both of the locking tab 780 and the locking tab 782 must flex to permit the locking tab 780 and the locking tab 782 to disengage from each other.

To move the IV catheter system 700 from the insertion configuration to the fluid delivery configuration, the clinician may position a digit (for example, a finger) on the leading edge 772 of the grip 752, and a digit (for example, a finger or thumb) on the trailing edge 744 of the first wing 740 and/or the push surface 746. The clinician may then pull the leading edge 772 proximally, and may push the trailing edge 744 and/or the push surface 746 distally. Application of the required threshold disengagement force may disengage the locking tab 782 from the locking tab 780, thereby permitting the needle component 704 to move proximally with respect to the catheter component 702. The catheter component 702 may then remain in place while the needle component 704 is withdrawn proximally from the catheter component 702.

Figure 8:
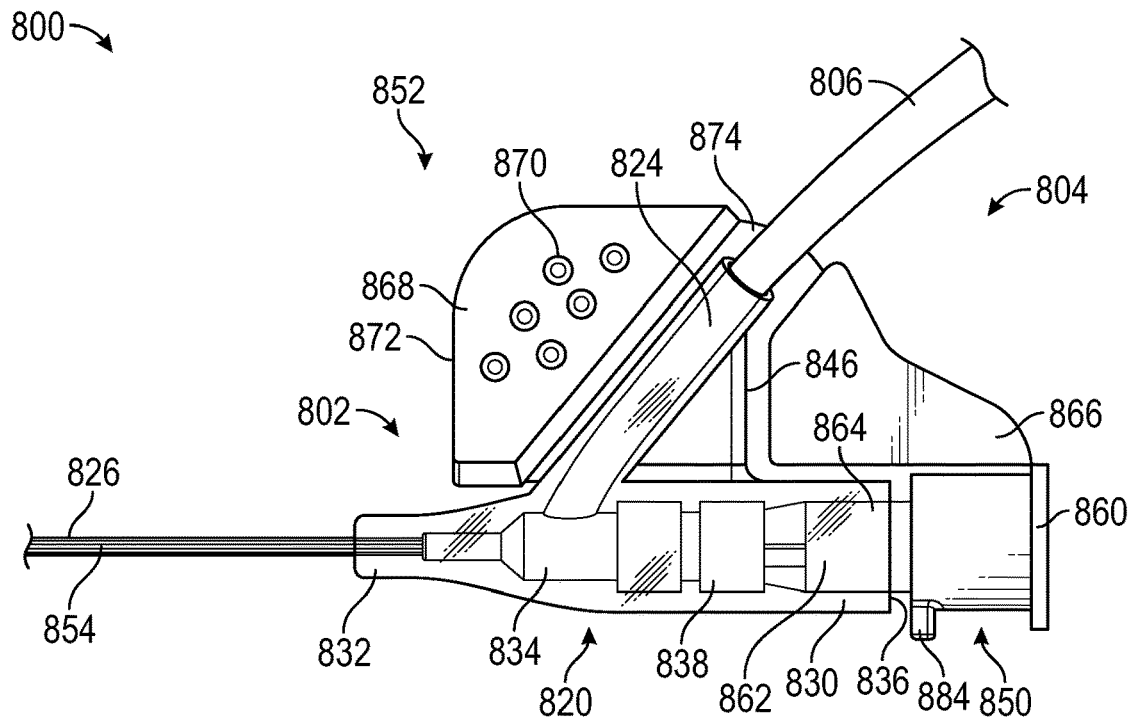
FIG. 8 is a plan view of an IV catheter system according to another alternative embodiment.

FIG. 8 is a plan view of an IV catheter system 800 according to another alternative embodiment. The IV catheter system 800 may have components similar to those of the IV catheter systems of previous embodiments. FIG. 8 illustrates only a catheter component 802, a needle component 804, and the distal end of an extension tube 806 connected to the catheter component 702.

As in previous embodiments, the catheter component 802 may have a catheter hub 820, an extension tubing junction 824, and a cannula 826. However, the catheter component 802 may not have a securement platform. Thus, the presence of a securement platform is optional. If desired, the catheter hub 820 may instead be secured directly to the patient's skin to keep the cannula 826 in place at the fluid delivery location.

The catheter hub 820 may have a generally tubular and/or hollow conical shape, with a proximal end 830 and a distal end 832. The catheter hub 820 may have a generally translucent exterior wall shaped to define a chamber 834 through which fluid flows to reach the fluid delivery location through the cannula 826. The catheter hub 820 may have a needle port 836 that connects to the needle component 804, proximate the proximal end 830 of the catheter hub 820. The catheter hub 820 may also have a septum 838 positioned within the chamber. The septum 838 may be a "low drag" septum as described previously.

The catheter component 802 may have a push feature in the form of a push surface 846 that extends between the extension tubing junction 824 and the intermediate portion of the catheter hub 820, between the proximal end 830 and the distal end 832. The push surface 846 may have a size selected to enable the clinician to relatively easily push on the push surface 846 with a digit to urge the catheter component 802 forward. The push surface 846 may be oriented substantially perpendicular to the axis of the catheter component 802 and the needle component 804.

The needle component 804 may have a needle hub 850, a grip 852, and a needle 854. The needle hub 850 may have a generally cylindrical shape with a proximal end 860 and a distal end 862. The needle hub 850 may also have a boss 864 that protrudes from the distal end 862 to interface with the needle port 836 of the catheter hub 820.

The grip 852 may have a generally planar shape, with a generally irregular shape when viewed from perpendicular to the grip 852. The grip 852 may have a narrow portion 866 that extends from the needle hub 850 to connect to a larger portion 868 that may be coupled to the extension tubing junction 824 when the IV catheter system 800 is in the insertion configuration. The grip 852 may have a leading edge 872, which may serve as a pull surface. The grip 852 may have one or more grip features 870, which may help provide a secure interface that facilitates gripping and/or moving the grip 852 by hand.

Further, the grip 852 may have a recess 874 that receives the extension tubing junction 824 when the IV catheter system 800 is in the insertion configuration. The recess 874 may be shaped to receive the extension tubing junction 824 and the push surface 846 to maintain alignment between the catheter component 802 and the needle component 804 during insertion. Positioning of the extension tubing junction 824 and the push surface 846 within the recess 874 may interfere with relative axial motion between the catheter component 802 and the needle component 804. Thus, when the IV catheter system 800 is to be moved from the insertion configuration to the fluid delivery configuration, the needle component 804 (and thence, the grip 852 with the recess 874) may be rotated relative to the catheter component 802 to withdraw the extension tubing junction 824 and the push surface 846 from within the recess 874. Proximal motion of the needle component 804 relative to the catheter component 802 may then be unimpeded. In some embodiments, however, the needle component 804 does not require rotation relative to the catheter component 802 in order to withdraw the extension tubing junction 824 and the push surface 846 from within the recess 874 (e.g., due to the flexibility of the extension tubing junction 824 and the push surface 846).

In addition to the leading edge 872, the needle component 804 may have a tab 884 that protrudes outward from the needle hub 850 in a direction generally opposite to that in which the grip 852 protrudes. The tab 884 may provide a pull surface that can be used by a clinician, in addition to and/or in the alternative to the leading edge 872 of the grip 852. This may provide additional options for the clinician to insert the IV catheter system 800 with a single hand and/or to move the IV catheter system 800 from the insertion configuration to the fluid delivery configuration with a single hand.

To move the IV catheter system 800 from the insertion configuration to the fluid delivery configuration, the clinician may first rotate the needle component 804 relative to the catheter component 802 to withdraw the extension tubing junction 824 and the push surface 846 from within the recess 874 as described above. Then, the clinician may position a digit (for example, a finger) on the leading edge 872 of the grip 852 and/or on the leading edge of the tab 884, and a digit (for example, a finger or thumb) on the push surface 846. The clinician may then pull the leading edge 872 and/or the tab 884 proximally, and may push the push surface 846 distally. The catheter component 802 may then remain in place while the needle component 804 is withdrawn proximally from the catheter component 802.

Figure 9A:
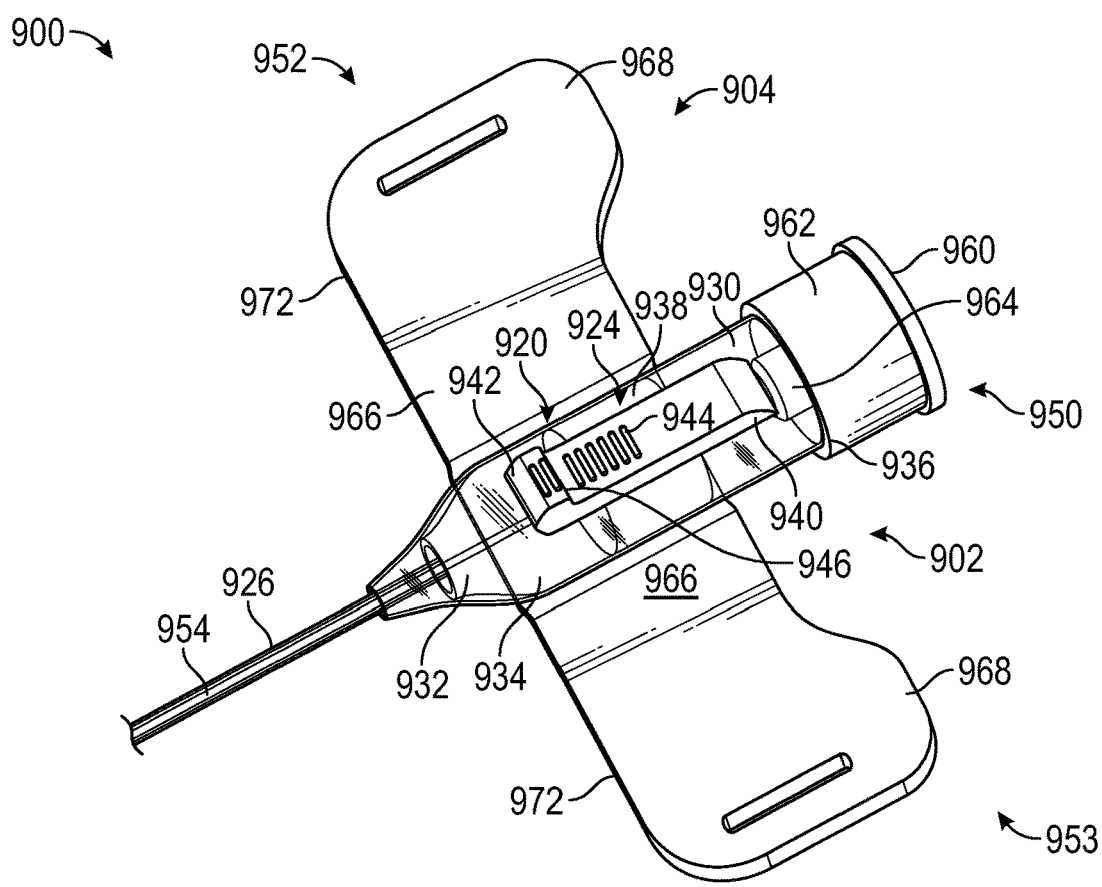
FIGS. 9A and 9B are perspective and side elevation, section views, respectively, of an IV catheter system according to yet another alternative embodiment.
Figure 9B:
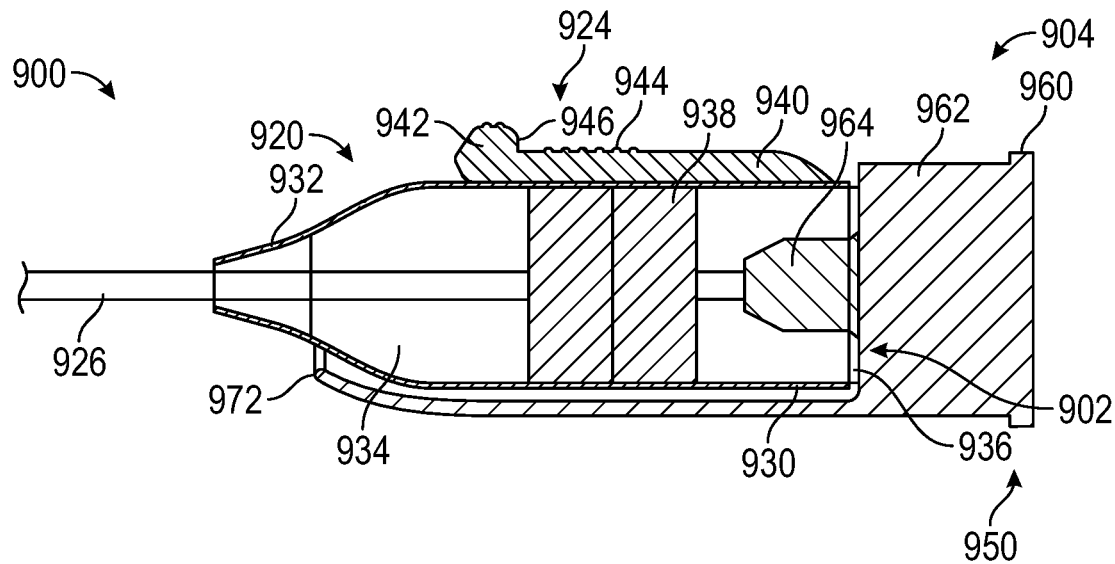

FIGS. 9A and 9B are perspective and side elevation, section views, respectively, of an IV catheter system 900 according to yet another alternative embodiment. The IV catheter system 900 may have components similar to those of the IV catheter systems of previous embodiments. FIGS. 9A and 9B illustrate only a catheter component 902 and a needle component 904. The IV catheter system 900 may be an open system rather than an integrated system; hence, the IV catheter system may not have an integrated extension tube or extension tubing junction.

As in previous embodiments, the catheter component 902 may have a catheter hub 920, a tab 924, and a cannula 926. However, as in the IV catheter system 800, the catheter component 902 may not have a securement platform. If desired, the catheter hub 920 may be secured directly to the patient's skin to keep the cannula 926 in place at the fluid delivery location.

The catheter hub 920 may have a generally tubular and/or hollow conical shape, with a proximal end 930 and a distal end 932. The catheter hub 920 may have a generally translucent exterior wall shaped to define a chamber 934 through which fluid flows to reach the fluid delivery location through the cannula 926. The catheter hub 920 may have a needle port 936 that connects to the needle component 904, proximate the proximal end 930 of the catheter hub 920. The catheter hub 920 may have a septum 938, which may be a "low drag" septum as described previously.

In alternative implementations (not shown), the catheter hub 920 may not have a septum. Rather, fluid may flow through the body of the catheter hub 920, from the proximal end 930 to the distal end 932, to reach the cannula 926. After the cannula 926 has been positioned at the fluid delivery location and the needle component 804 has been withdrawn from the catheter component 802, the fluid supply may be connected to the needle port 936 of the catheter hub 920 to supply the fluid to be infused to the proximal end 930 of the catheter hub 920.

The tab 924 may extend outward from the catheter hub 920, and may provide a ready gripping surface that facilitates user manipulation of the catheter hub 920. The tab 924 may have a main portion 940 and an upraised distal end 942. A plurality of grip features 944 may be positioned on the main portion 940 and the distal end 942. The tab 924 may serve as a push feature that can be readily pushed with a digit of a hand to facilitate insertion of the IV catheter system 900 and/or motion of the IV catheter system 900 from the insertion configuration to the fluid delivery configuration. The user may place a digit on the main portion 940 and/or on the upraised distal end 942 of the tab 924. Further, the shape of the upraised distal end 942 may define a push surface 946 oriented substantially perpendicular to the axis of the cannula 926. The user may place a digit on the main portion 940, abutting the push surface 946, to facilitate exertion of forward (i.e., distal) pressure on the catheter component 902.

The needle component 904 may have a needle hub 950, a first grip 952, a second grip 953, and a needle 954. The needle hub 950 may have a generally cylindrical shape with a proximal end 960 and a distal end 962. The needle hub 950 may also have a boss 964 that protrudes from the distal end 962 to interface with the needle port 936 of the catheter hub 920.

The first grip 952 and the second grip 953 may each have a generally planar shape, with an irregular shape when viewed from perpendicular to the first grip 952 and the second grip 953. Each of the first grip 952 and the second grip 953 may have a narrow portion 966 that extends from the needle hub 950 to connect to a larger portion 968. The first grip 952 and the second grip 953 may each have a leading edge 972, which may serve as a pull surface. The leading edges 972 of the first grip 952 and the second grip 953 may cooperate to define a single continuous surface that extends around the periphery of the distal end 932 of the catheter hub 920 to connect the first grip 952 to the second grip 953. This interconnection between the first grip 952 and the second grip 953, which is more clearly shown in FIG. 9B, may act as a kink-resistant feature and/or provide additional support tending to keep the needle component 904 and the catheter component 902 parallel during insertion and/or transition from the insertion configuration to the fluid delivery configuration.

To move the IV catheter system 900 from the insertion configuration to the fluid delivery configuration, the clinician may position a digit (for example, a finger) on the leading edge 972 of the first grip 952 and/or the leading edge 972 of the second grip 953, and a digit (for example, a finger or thumb) on the tab 924 (for example, on the push surface 946). The clinician may then pull the leading edge 972 proximally, and may push the push surface 946 distally. The catheter component 902 may then remain in place while the needle component 904 is withdrawn proximally from the catheter component 902.

Figure 10A:
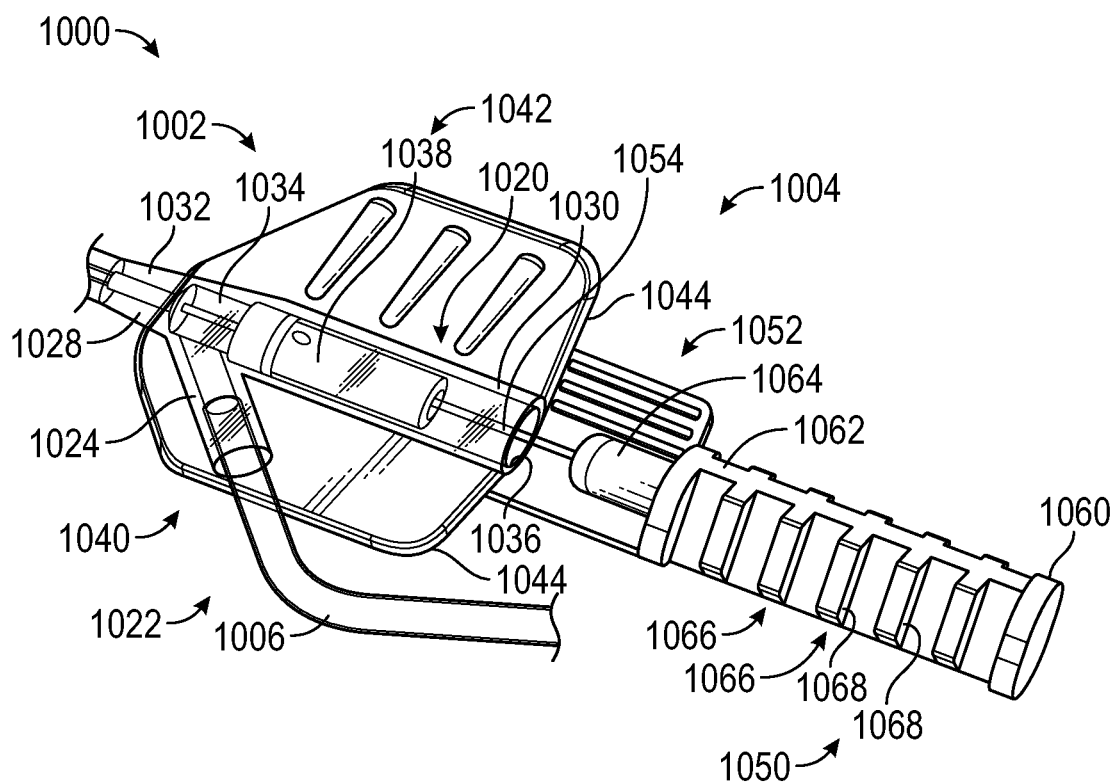
FIGS. 10A, 10B, and 10C are perspective views of an IV catheter system according to still another alternative embodiment, with the catheter component and needle component partially separated, in the insertion configuration, and with the catheter component and needle component partially separated, respectively.
Figure 10B:
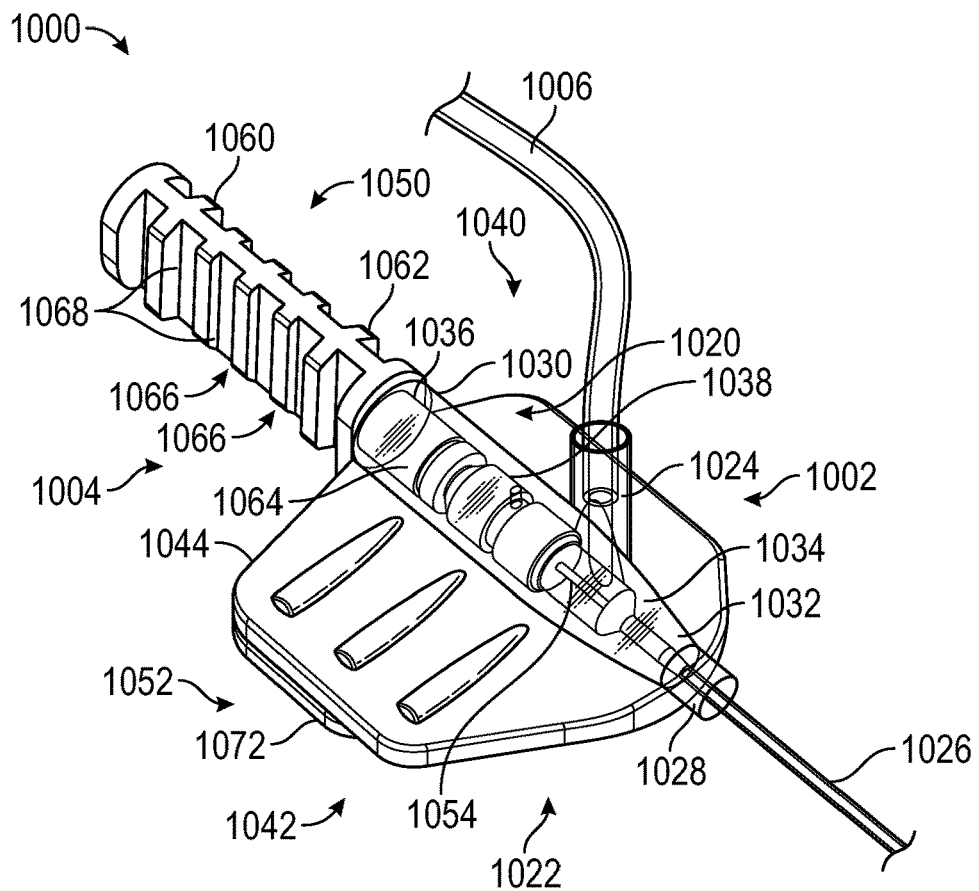
Figure 10C:
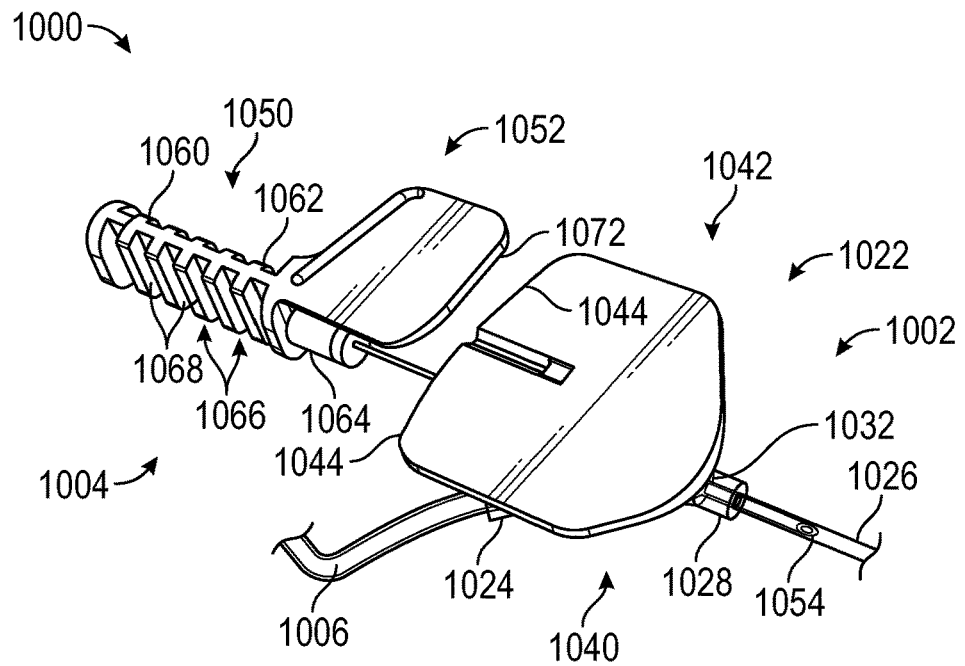

FIGS. 10A, 10B, and 10C are perspective views of an IV catheter system 1000 according to still another alternative embodiment, with the catheter component 1002 and needle component 1004 partially separated, in the insertion configuration, and with the catheter component 1002 and needle component 1004 partially separated, respectively. The IV catheter system 1000 may have components similar to those of the IV catheter systems of previous embodiments. FIG. 6 illustrates only a catheter component 1002, a needle component 1004, and the distal end of an extension tube 1006 connected to the catheter component 1002.

As in previous embodiments, the catheter component 1002 may have a catheter hub 1020, a securement platform 1022, an extension tubing junction 1024, and a cannula 1026. The catheter hub 1020 may have a generally tubular and/or hollow conical shape, with a proximal end 1030 and a distal end 1032. The catheter hub 1020 may have a generally translucent exterior wall shaped to define a chamber 1034 through which fluid flows to reach the fluid delivery location through the cannula 1026. The catheter hub 1020 may have a needle port 1036 that connects to the needle component 1004, proximate the proximal end 1030 of the catheter hub 1020. The catheter hub 1020 may also have a septum 1038 positioned within the chamber 1034. The septum may be a "low drag" septum as described previously.

Further, the catheter hub 1020 may have a kink resistance feature that helps to avoid kinking of the cannula 1026 during insertion and/or infusion. The kink resistance feature may take the form of a proximal extension 1028 on the distal end 1032 of the catheter hub 1020. The proximal extension 1028 may receive the cannula 1026, and may provide some resistance to bending of the cannula 1026 at the juncture of the cannula 1026 to the proximal end 1030 to relieve the bending strain at that location, thereby helping avoid kinking or other undesired bending of the cannula 1026.

The securement platform 1022 may be attached to the skin of the patient during fluid delivery to keep the cannula 1026 in place at the fluid delivery location. The securement platform 1022 may have a first wing 1040 and a second wing 1042, each of which may be generally planar in shape. The first wing 1040 and the second wing 1042 may each have a trailing edge 1044 that can act as a push surface. The first wing 1040 and the second wing 1042 may extend in opposite directions, outward from the axis of the catheter hub 1020. The first wing 1040 may be adjacent to the extension tubing junction 1024.

The needle component 1004 may have a needle hub 1050, a grip 1052, and a needle 1054. The needle hub 1050 may have a generally cylindrical shape with a proximal end 1060 and a distal end 1062. The needle hub 1050 may also have a boss 1064 that protrudes from the distal end 1062 to interface with the needle port 1036 of the catheter hub 1020. Between the proximal end 1060 and the distal end 1062, the needle hub 1050 may have a plurality of ridges 1066 that protrude outwardly. The needle hub 1050 may be elongated so that the user can grip the ridges 1066 at any of various locations along the length of the needle hub 1050. The ridges 1066, or more specifically, the distally-facing surfaces of the ridges 1066, may optionally act as pull surfaces 1068 that facilitate gripping of the needle component 1004 to move the IV catheter system 1000 from the insertion configuration to the fluid delivery configuration.

The grip 1052 may have a generally planar shape, with a generally rectangular shape when viewed from perpendicular to the grip 1052. The grip 1052 may lie in abutting relation to the first wing 1040 of the securement platform 1022 when the IV catheter system 1000 is in the insertion configuration. The grip 1052 may have a leading edge 1072, which may serve as a pull surface. The grip 1052 and/or the first wing 1040 may have one or more grip features (not shown), which may help provide a secure interface that facilitates gripping and/or moving the grip 1052 by hand.

To move the IV catheter system 1000 from the insertion configuration to the fluid delivery configuration, the clinician may position a digit (for example, a finger) on the leading edge 1072 of the grip 1052 and/or the pull surfaces 1068, and a digit (for example, a finger or thumb) on the trailing edge 1044 of the first wing 1040 and/or the trailing edge 1044 of the second wing 1042. The clinician may then pull one or both of the leading edges 1072 proximally, and may push the trailing edge 1044 and/or the pull surfaces 1068 distally. This may cause the catheter component 1002 to remain in place while the needle component 1004 is withdrawn proximally from the catheter component 1002.

Figure 11:
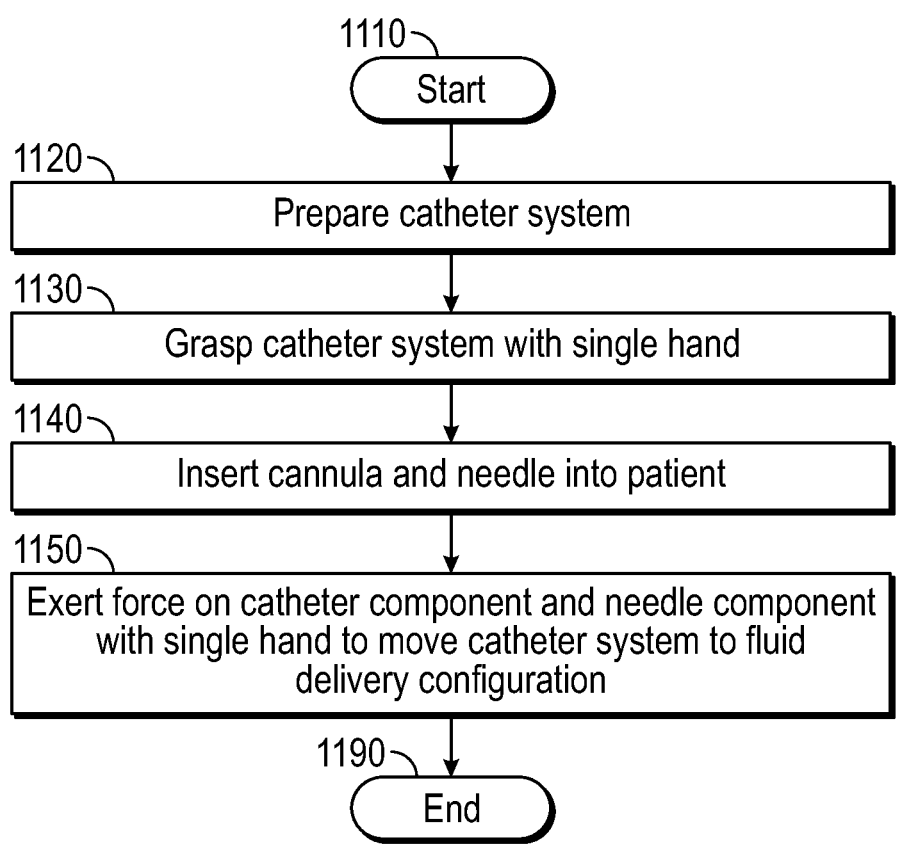
FIG. 11 is a flowchart diagram depicting one method of preparing an IV catheter system to deliver fluid to a patient, according to one embodiment.

FIG. 11 is a flowchart diagram depicting one method of preparing an IV catheter system to deliver fluid to a patient, according to one embodiment. The method of FIG. 11 may be carried out with any of the IV catheter systems disclosed in FIGS. 1 through 10C, or with other IV catheter system embodiments that are not specifically shown or described herein. By way of example, the method will be described in connection with the IV catheter system 100 of FIG. 1.

Further, the method of FIG. 11 is merely exemplary; other methods may be used in conjunction with any of the IV catheter system embodiments included within the scope of the present disclosure.

The method may start 1110 with a step 1120 in which the catheter system is prepared. This preparation may include connecting various components (such as the catheter component 102, the needle component 104, the extension tube 106, the clamp 108, and/or the luer lock adapter 110 of FIG. 1, by way of example) together. Further, this may include preparing any adhesives needed to secure the catheter component 102 to the patient, preparing components of the fluid source to be connected to the IV catheter system 100, and/or the like.

In a step 1130, the IV catheter system 100 may be grasped with a single hand. This may involve placing digits of the hand to contact the pull surface(s) of the needle component 104 and the push surface(s) of the catheter component 102, as described above. Notably, the surfaces that serve as pull surfaces and push surfaces may vary, depending on the specific embodiment utilized. Further, catheter insertion may involve primarily pushing; accordingly, the clinician may elect not to make contact with the pull surfaces at this stage, but to contact them when the IV catheter system 100 is to be moved to the fluid delivery configuration.

In a step 1140, the IV catheter system 100 may be manipulated to insert the cannula 126 into the patient. This may optionally be done with a single hand. Insertion may continue until the tip of the cannula 126 has reached the fluid delivery location. Insertion may be carried out by pushing on the push surfaces and/or other surfaces of the catheter component 102 and/or the needle component 104.

In a step 1150, the IV catheter system 100 may be moved from the insertion configuration to the fluid delivery configuration. If the clinician has not yet contacted the pull surface(s) of the needle component 104, he or she may do this now with one or more digits of a hand. Optionally, the same hand used to insert the IV catheter system 100 may be used, exclusively (i.e., without assistance from the other hand) to move the IV catheter system 100 to the fluid delivery configuration. The clinician may pull the pull surface(s) proximally, while pushing on the push surface(s) to keep the catheter component 102 in place. Thus, the catheter component 102 may be kept in place with the tip of the cannula 126 at the fluid delivery location while the needle component 104 is withdrawn proximally from the catheter component 102 to unblock the fluid delivery path to the fluid delivery location.

This may optionally be accomplished with a single hand. Thus, the other hand may be used to perform other tasks during insertion and/or motion of the IV catheter system 100 to the fluid delivery configuration. For example, the clinician may use the other hand to hold the patient's arm (or other body part in which the fluid delivery location is located), prepare other components for interconnection with the IV catheter system 100, prepare any necessary blood testing materials, and/or the like.

The method may then end 1190. With the IV catheter system 100 in the fluid delivery configuration, the fluid source may then be connected to the catheter component 102 to deliver the fluid to the patient.

An IV catheter system may have a wide variety of alternative configurations within the scope of the present disclosure. Supplemental embodiments will be shown and described in brief, with reference to FIGS. 12A through 15D.

Figure 12A:
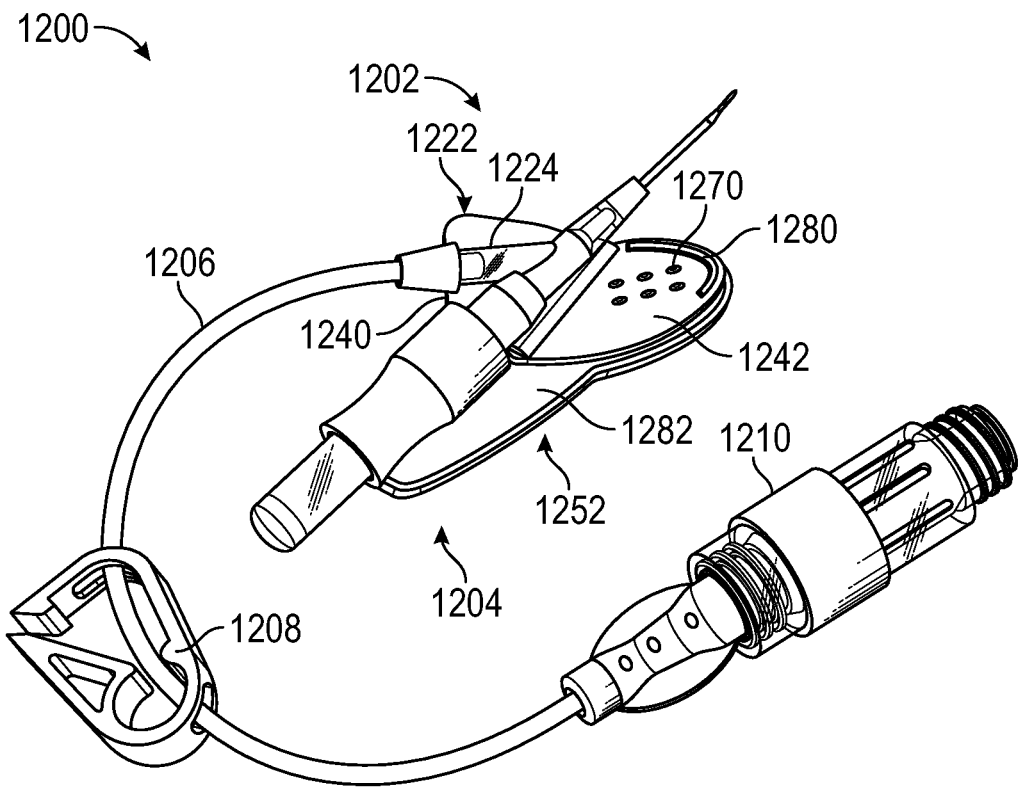
FIGS. 12A and 12B are perspective views of an IV catheter system according to yet another alternative embodiment, in a fully-assembled state and in an exploded state, respectively.
Figure 12B:
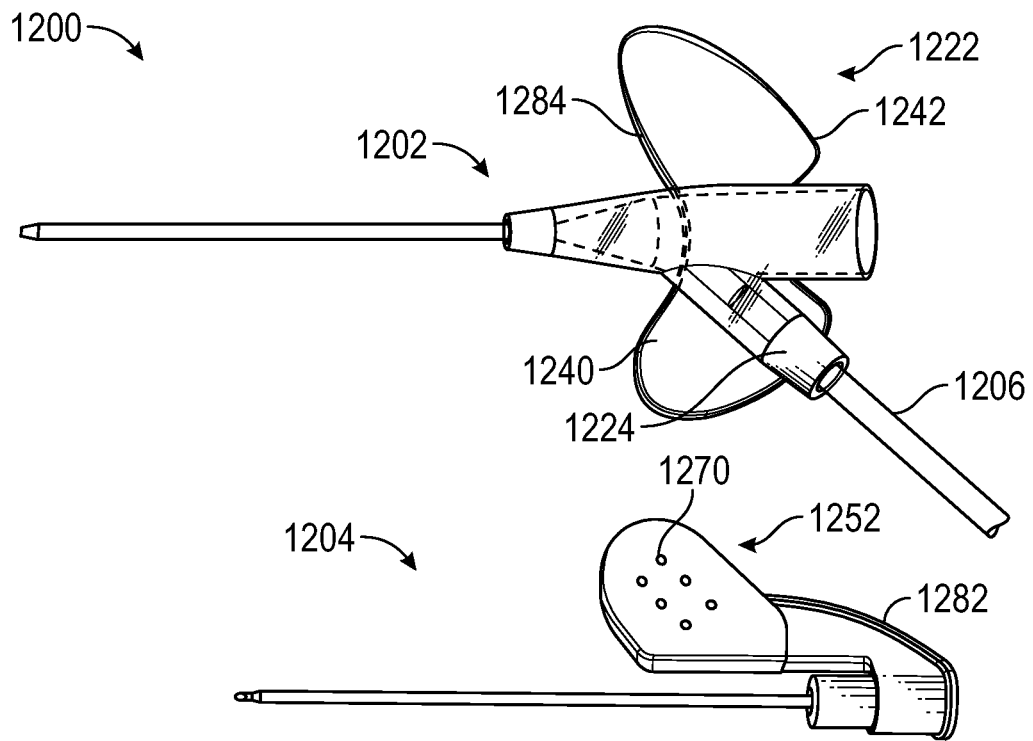

FIGS. 12A and 12B are perspective views of an IV catheter system 1200 according to yet another alternative embodiment, in a fully-assembled state and in an exploded state, respectively. The IV catheter system 1200 may have components similar to those of the IV catheter systems of previous embodiments. FIG. 12A illustrates a catheter component 1202, a needle component 1204, extension tubing 1206, a clamp 1208, and a luer lock adapter 1210. Only the catheter component 1202, the needle component 1204, and the extension tubing 1206 are illustrated in FIG. 12B. The IV catheter system 1200 may be an integrated system, as in some of the previous embodiments; hence, the extension tubing 1206 may be pre-attached to the catheter component 1202. Several components of the IV catheter system 1200 may be similar to those of previous embodiments and thus will not be described explicitly; rather, understanding of the configuration and operation of these components can be obtained by referring to the descriptions of previously described drawings.

As shown, the catheter component 1202 may have a securement platform 1222 with a first wing 1240 and a second wing 1242. The first wing 1240 may be integrated with an extension tubing junction 1224 that connects the extension tubing 1206 to the catheter component 1202. The second wing 1242 may overlie a grip 1252 of the needle component 1204 in the insertion configuration such that the distal ends of the grip 1242 and the second wing 1242 have substantially the same, generally elliptical shape.

The securement platform 1222 may optionally be "soft," i.e., formed of a relatively compliant material that conforms easily to the skin of the patient. In some embodiments, the securement platform 1222 may be formed of a soft plastic, an elastomer such as silicone rubber, and/or the like. The securement platform 1222 and the grip 1252 may have one or more grip features 1270 that facilitate gripping and/or manipulation of the securement platform 1222 and/or the grip 1252 by hand.

Further, the securement platform 1222 and/or the grip 1252 may optionally have features that further facilitate motion of the IV catheter system 1200 from the insertion configuration to the fluid delivery configuration. Specifically, the second wing 1242 may have a distal ridge 1280 that may act as a push feature. The distal ridge 1280 may be positioned so that a digit can easily contact the proximal side of the distal ridge 1280 to apply distal pressure on the second wing 1242. The grip 1252 may have a peripheral ridge 1282 positioned at an exterior edge of the grip 1252. The peripheral ridge 1282 may act as a pull feature. The peripheral ridge 1282 may be positioned such that a digit can easily contact the apex and/or the distal side of the peripheral ridge 1282 to apply proximal pressure on the grip 1252. The peripheral ridge 1282 may optionally be positioned just outward of the outermost edge of the second wing 1242 when the IV catheter system 1200 is in the insertion configuration, so that the peripheral ridge 1282 can be contacted by the digit even when the second wing 1242 is positioned to overlie the grip 1252.

Additionally or alternatively, the securement platform 1222 and/or the grip 1252 may have one or more friction reducing features that facilitate motion from the insertion configuration to the fluid delivery configuration. Such friction reducing features may optionally reduce the level of friction between the grip 1252 and the second wing 1242 so that the grip 1252 and the second wing 1242 can more easily slide past each other. One such friction reducing feature may be a central ridge 1284 on the second wing 1242, which may protrude toward the grip 1252. The central ridge 1284 may abut the grip 1252 in the insertion configuration to reduce the surface area of the second wing 1242 that is in contact with the grip 1252, thereby reducing frictional resistance to sliding motion between the grip 1252 and the second wing 1242. The central ridge 1284 may thus reduce the force required to move the IV catheter system 1200 from the insertion configuration to the fluid delivery configuration, thereby making this transition easier to accomplish with only a single hand.

Figure 13A:
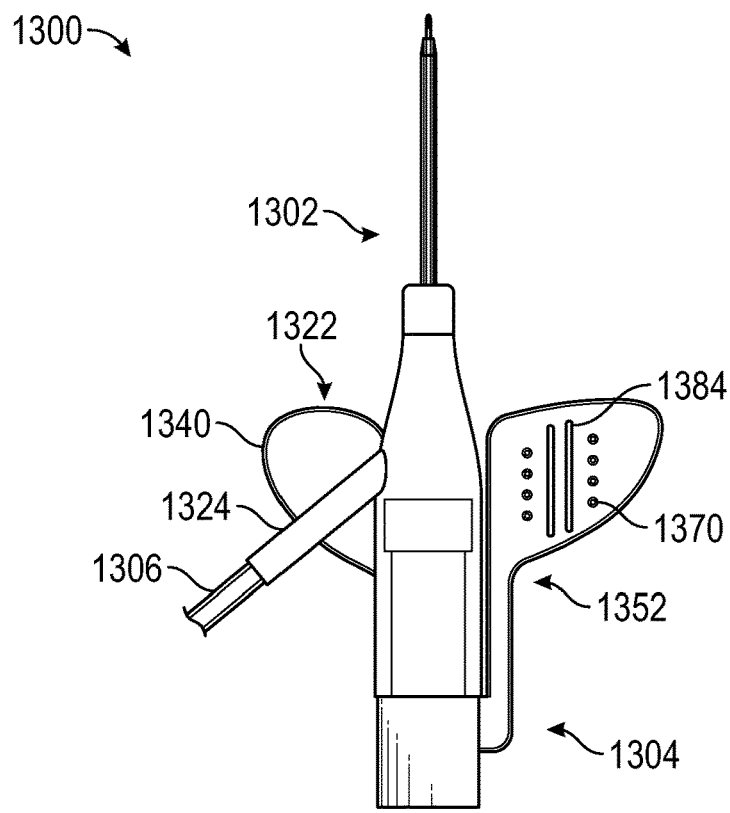
FIGS. 13A and 13B are perspective views of an IV catheter system according to yet another alternative embodiment, in an open state and a compacted state, respectively.
Figure 13B:
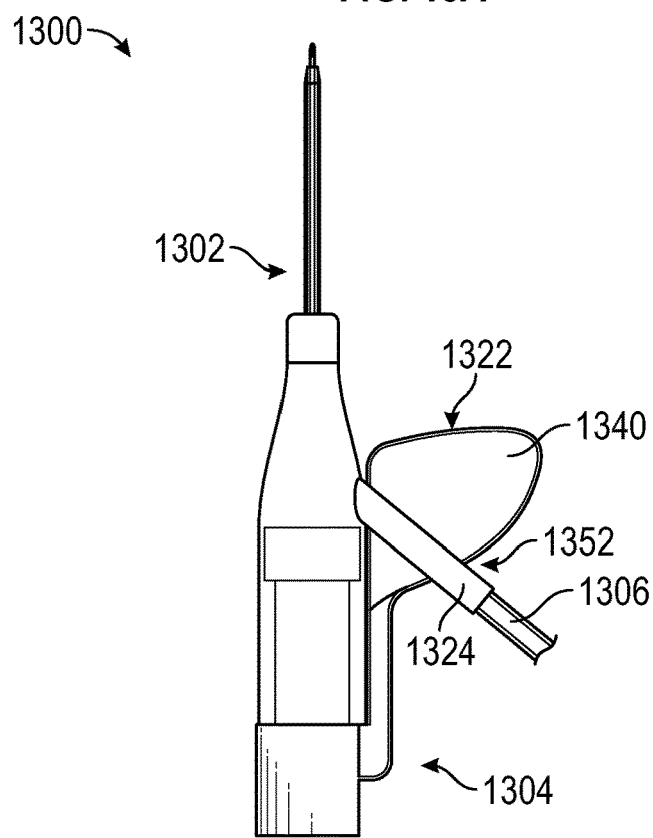

FIGS. 13A and 13B are perspective views of an IV catheter system 1300 according to yet another alternative embodiment, in an open state and a compacted state, respectively. The clinician may have the flexibility to insert and/or move the IV catheter system to the fluid delivery configuration in the open state or in the compacted state. One or both states may facilitate manipulation of the IV catheter system 1300 with the digits of a single hand. The IV catheter system 1300 may have components similar to those of the IV catheter systems of previous embodiments. FIGS. 13A and 13B illustrate a catheter component 1302, a needle component 1304, and extension tubing 1306. The IV catheter system 1300 may be an integrated system, as in some of the previous embodiments; hence, the extension tubing 1306 may be pre-attached to the catheter component 1302. Several components of the IV catheter system 1300 may be similar to those of previous embodiments and thus will not be described explicitly; rather, understanding of the configuration and operation of these components can be obtained by referring to the descriptions of previously described drawings.

As shown, the catheter component 1302 may have a securement platform 1322 with a first wing 1340 and no second wing. The first wing 1340 may be integrated with an extension tubing junction 1324 that connects the extension tubing 1306 to the catheter component 1302. In the compacted state shown in FIG. 13B, the first wing 1340 may overlie a grip 1352 of the needle component 1304 such that the distal ends of the grip 1352 and the first wing 1340 have substantially the same, generally elliptical shape. In the open state of FIG. 13A, the first wing 1340 and the grip 1352 may extend in generally opposite directions, providing a generally symmetrical profile.

The securement platform 1322 may optionally be "soft," i.e., formed of a relatively compliant material that conforms easily to the skin of the patient. In some embodiments, the securement platform 1322 may be formed of a soft plastic, an elastomer such as silicone rubber, and/or the like. The securement platform 1322 and the grip 1352 may have one or more grip features 1370 that facilitate gripping and/or manipulation of the securement platform 1322 and/or the grip 1352 by hand.

Further, the securement platform 1322 and/or the grip 1352 may have one or more friction reducing features that facilitate motion from the insertion configuration to the fluid delivery configuration. Such friction reducing features may optionally reduce the level of friction between the grip 1352 and the first wing 1340 so that the grip 1252 and the first wing 1340 can more easily slide past each other in the compacted state. One such friction reducing feature may be a central ridge 1384 on the grip 1352, which may protrude toward the first wing 1340 in the compacted state. The central ridge 1384 may abut the first wing 1340 in the insertion configuration, in the compacted state to reduce the surface area of the grip 1352 that is in contact with the first wing 1340, thereby reducing frictional resistance to sliding motion between the grip 1352 and the first wing 1340. The central ridge 1384 may thus reduce the force required to move the IV catheter system 1300 from the insertion configuration to the fluid delivery configuration, thereby making this transition easier to accomplish with only a single hand when in the closed configuration.

Figure 14A:
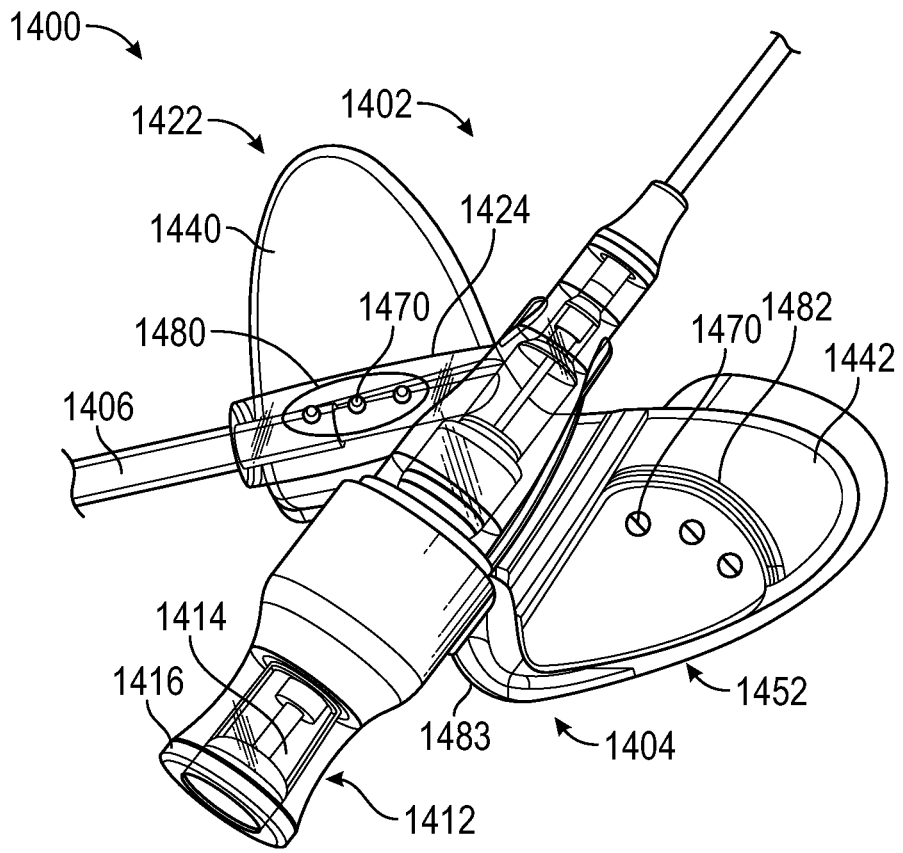
FIGS. 14A, 14B, 14C, and 14D are perspective views of an IV catheter system according to yet another alternative embodiment, in the insertion configuration in a compacted state, with the catheter component in isolation, in the insertion configuration in an open state, and with the flash component in an exploded state, respectively.
Figure 14B:
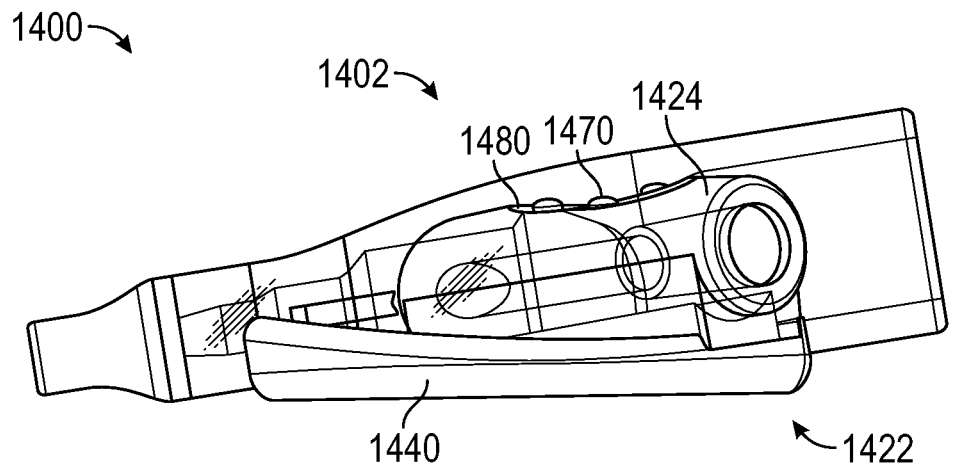

FIGS. 14A, 14B, 14C, and 14D are perspective views of an IV catheter system 1400 according to yet another alternative embodiment, in the insertion configuration in a compacted state, with the catheter component 1402 in isolation, in the insertion configuration in an open state, and with the flash component 1412 in an exploded state, respectively. The IV catheter system 1400 may have components similar to those of the IV catheter systems of previous embodiments. FIG. 14A illustrates a catheter component 1402, a needle component 1404, extension tubing 1406, and a flash component 1412. The IV catheter system 1400 may be an integrated system, as in some of the previous embodiments; hence, the extension tubing 1406 may be pre-attached to the catheter component 1402. Several components of the IV catheter system 1400 may be similar to those of previous embodiments and thus will not be described explicitly; rather, understanding of the configuration and operation of these components can be obtained by referring to the descriptions of previously described drawings.

As shown, the catheter component 1402 may have a securement platform 1422 with a first wing 1440 and a second wing 1442. The first wing 1440 may be integrated with an extension tubing junction 1424 that connects the extension tubing 1406 to the catheter component 1402. The second wing 1442 may overlie a grip 1452 of the needle component 1404 in the insertion configuration such that the distal ends of the grip 1442 and the second wing 1442 have substantially the same, generally elliptical shape, except that the grip 1452 may be slightly larger than the second wing 1442. Thus, the grip 1452 may extend beyond the profile of the second wing 1442.

The securement platform 1422 may optionally be "soft," i.e., formed of a relatively compliant material that conforms easily to the skin of the patient. In some embodiments, the securement platform 1422 may be formed of a soft plastic, an elastomer such as silicone rubber, and/or the like. The securement platform 1422 and the grip 1452 may have one or more grip features 1470 that facilitate gripping and/or manipulation of the securement platform 1422 and/or the grip 1452 by hand.

Further, the securement platform 1422 and/or the grip 1452 may optionally have features that further facilitate motion of the IV catheter system 1400 from the insertion configuration to the fluid delivery configuration. Specifically, the extension tubing junction 1424 may have a depression 1480 that may act as a push feature. The depression 1480 may be positioned so that a digit can easily contact the extension tubing junction 1424, and thence the first wing 1440, to apply distal pressure on the first wing 1440. The second wing 1442 may have stepdown 1482 at which the second wing 1442 moves from a greater thickness toward the distal end of the second wing 1442 to a lesser thickness toward the proximal end of the second 1442. The stepdown 1482 may thus provide a proximally-oriented surface that can also act as a push feature. The clinician may place a digit on the proximally-oriented surface of the second wing 1442 to facilitate exertion of distal pressure on the second wing 1442.

The grip 1452 may have a proximal ridge 1483 positioned at a proximal edge of the grip 1452. The proximal ridge 1483 may act as a pull feature. The proximal ridge 1483 may be positioned such that a digit can easily contact the apex and/or the distal side of the proximal ridge 1483 to apply proximal pressure on the grip 1452. The proximal ridge 1483 may optionally be positioned just proximally of the proximal edge of the second wing 1442 when the IV catheter system 1400 is in the insertion configuration, so that the proximal ridge 1483 can be contacted by the digit even when the second wing 1442 is positioned to overlie the grip 1452.

Additionally or alternatively, the securement platform 1422 and/or the grip 1452 may have one or more friction reducing features that facilitate motion from the insertion configuration to the fluid delivery configuration. Such friction reducing features may optionally reduce the level of friction between the grip 1452 and the second wing 1442 so that the grip 1452 and the second wing 1442 can more easily slide past each other. One such friction reducing feature may be a series of central bumps 1484 on the grip 1452, which may protrude toward the second wing 1442. The central bumps 1484 may abut the second wing 1442 in the insertion configuration to reduce the surface area of the second wing 1442 that is in contact with the grip 1452, thereby reducing frictional resistance to sliding motion between the grip 1452 and the second wing 1442. The central bumps 1484 may thus reduce the force required to move the IV catheter system 1400 from the insertion configuration to the fluid delivery configuration, thereby making this transition easier to accomplish with only a single hand.

Figure 14C:
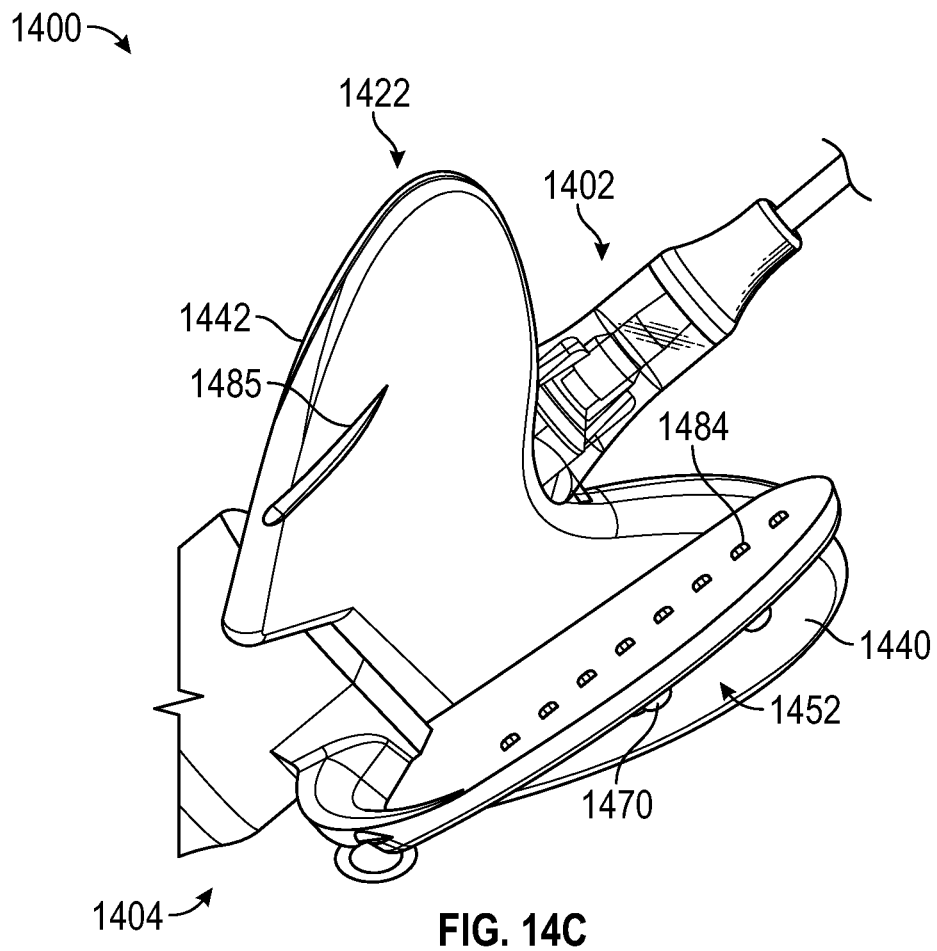
Figure 14D:
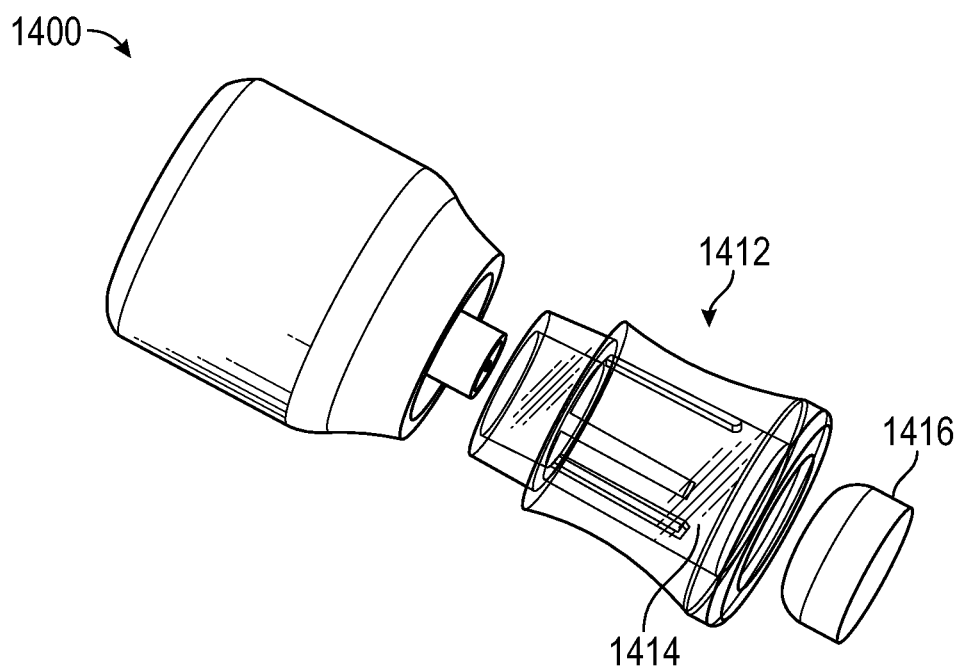

As shown in FIG. 14C, the central bumps 1484 may optionally be aligned with a central trough 1485 formed in the surface of the second wing 1442 that faces the grip 1452. The central trough 1485 may receive the central bumps 1484. Thus, the central bumps 1484 and the central trough 1485 may act as alignment features to maintain alignment between the second wing 1442 and the grip 1452, thereby reducing the likelihood of binding or other resistance to motion to the fluid delivery configuration that could otherwise be caused by misalignment between the catheter component 1402 and the needle component 1404.

FIG. 14C illustrates an open state in which the needle component 1404 is rotated relative to the catheter component 1402 in a manner that positions the grip 1452 substantially perpendicular to the securement platform 1422. In this state, the IV catheter system 1400 may provide alternative ergonomics for inserting the cannula into the fluid delivery location and/or moving the IV catheter system 1400 to the fluid delivery configuration. In this state, the central bumps 1484 may not be positioned within the central trough 1485. However, when the needle component 1404 and catheter component 1402 are again rotated relative to each other to position the IV catheter system 1400 in the compacted state, the central bumps 1484 may enter the central trough 1485 to ensure proper alignment between the needle component 1404 is rotated relative to the catheter component 1402.

The flash component 1412 may indicate proper placement of the cannula of the catheter component 1402. When the cannula penetrates a blood vessel, the resulting blood flow may pass into the catheter component 1402 and through the needle component 1404 to reach the flash component 1412, which may be secured to the proximal end of the needle component 1404. The blood may enter a flash chamber 1414 of the flash component 1412, which may be visible to the user through transparent walls of the flash component 1412. The flash component 1412 may also have a vent 1416 that permits egress of any air in the IV catheter system 1400 as the blood enters, to ensure that the blood is able to fill the flash component 1412.

Figure 15A:
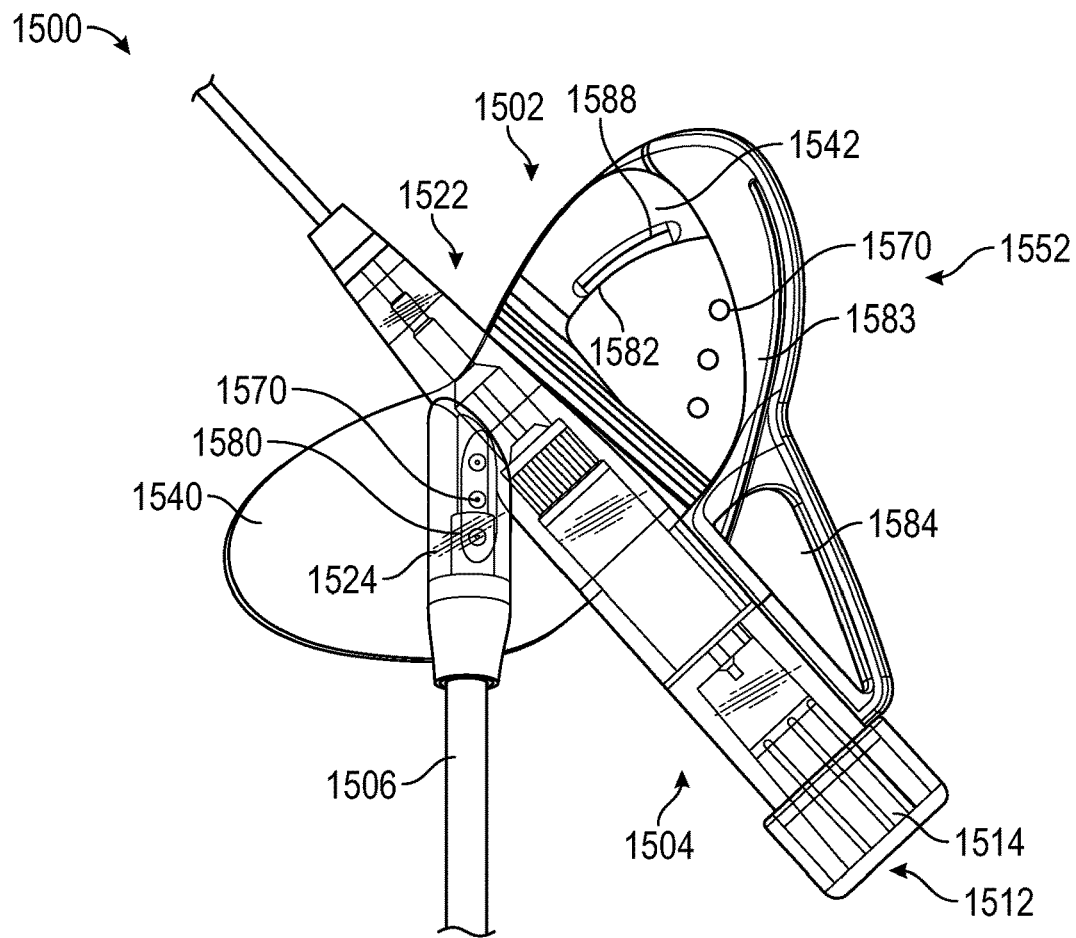
FIGS. 15A, 15B, 15C, and 15D are perspective views of an IV catheter system according to yet another alternative embodiment, in the insertion configuration in a compacted state, with the catheter component and needle component in isolation, in the insertion configuration in an open state, and with the flash component in an exploded state, respectively.
Figure 15B:
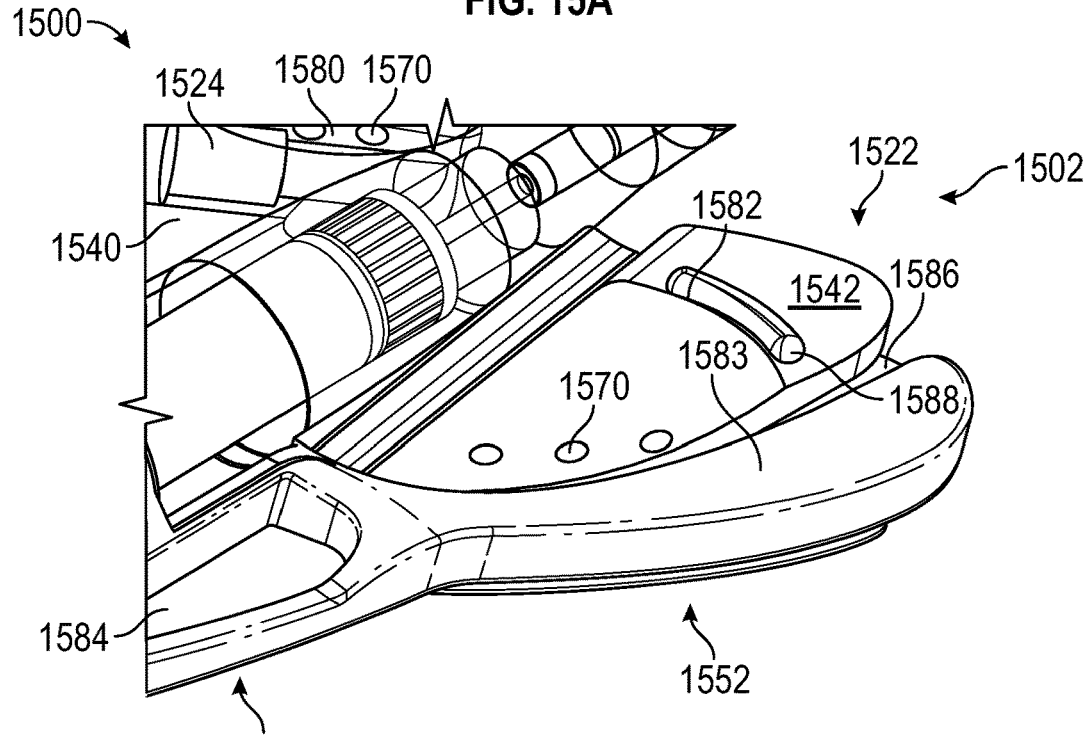

FIGS. 15A, 15B, 15C, and 15D are perspective views of an IV catheter system 1500 according to yet another alternative embodiment, in the insertion configuration in a compacted state, with the catheter component 1502 and needle component 1504 in isolation, in the insertion configuration in an open state, and with the flash component 1512 in an exploded state, respectively. The IV catheter system 1500 may have components similar to those of the IV catheter systems of previous embodiments. FIG. 15A illustrates a catheter component 1502, a needle component 1504, extension tubing 1506, and a flash component 1512. The IV catheter system 1500 may be an integrated system, as in some of the previous embodiments; hence, the extension tubing 1506 may be pre-attached to the catheter component 1502. Several components of the IV catheter system 1500 may be similar to those of previous embodiments and thus will not be described explicitly; rather, understanding of the configuration and operation of these components can be obtained by referring to the descriptions of previously described drawings.

As shown, the catheter component 1502 may have a securement platform 1522 with a first wing 1540 and a second wing 1542. The first wing 1540 may be integrated with an extension tubing junction 1524 that connects the extension tubing 1506 to the catheter component 1502. The second wing 1542 may overlie a grip 1552 of the needle component 1504 in the insertion configuration such that the distal ends of the grip 1542 and the second wing 1542 have substantially the same, generally elliptical shape, except that the grip 1552 may be slightly larger than the second wing 1542. Thus, the grip 1552 may extend beyond the profile of the second wing 1542.

The securement platform 1522 may optionally be "soft," i.e., formed of a relatively compliant material that conforms easily to the skin of the patient. In some embodiments, the securement platform 1522 may be formed of a soft plastic, an elastomer such as silicone rubber, and/or the like. The securement platform 1522 and the grip 1552 may have one or more grip features 1570 that facilitate gripping and/or manipulation of the securement platform 1522 and/or the grip 1552 by hand.

Further, the securement platform 1522 and/or the grip 1552 may optionally have features that further facilitate motion of the IV catheter system 1500 from the insertion configuration to the fluid delivery configuration. Specifically, the extension tubing junction 1524 may have a depression 1580 that may act as a push feature. The depression 1580 may be positioned so that a digit can easily contact the extension tubing junction 1524, and thence the first wing 1540, to apply distal pressure on the first wing 1540. The second wing 1542 may have stepdown 1582 at which the second wing 1542 moves from a greater thickness toward the distal end of the second wing 1542 to a lesser thickness toward the proximal end of the second 1542. The stepdown 1582 may thus provide a proximally-oriented surface that can also act as a push feature. The clinician may place a digit on the proximally-oriented surface of the second wing 1542 to facilitate exertion of distal pressure on the second wing 1542. A stepdown ridge 1588 may be positioned proximate the stepdown 1582 to broaden the size of the proximally-facing surface provided by the stepdown 1582, thereby facilitating use of the stepdown 1582 as a push feature.

The grip 1552 may have a peripheral ridge 1583 positioned at an outer edge of the grip 1552. The peripheral ridge 1583 may act as a pull feature. The peripheral ridge 1583 may be positioned such that a digit can easily contact the apex and/or the distal side of the peripheral ridge 1583 to apply proximal pressure on the grip 1552. The peripheral ridge 1583 may optionally be positioned outward of the outer edge of the second wing 1542 when the IV catheter system 1500 is in the insertion configuration, so that the peripheral ridge 1583 can be contacted by the digit even when the second wing 1542 is positioned to overlie the grip 1552. The peripheral ridge 1583 may define the boundary of a distal recess 1586 of the grip 1552 within which the second wing 1542 can reside in the insertion configuration.

Further, the grip 1552 may have a proximal recess 1584. The upraised edges of the grip 1552 that surround and define the proximal recess 1584 may also act as pull features. The clinician may place the digit of a hand on any of these edges to exert proximal pressure on the grip 1552.

Additionally or alternatively, the securement platform 1522 and/or the grip 1552 may have one or more friction reducing features that facilitate motion from the insertion configuration to the fluid delivery configuration. Such friction reducing features may optionally reduce the level of friction between the grip 1552 and the second wing 1542 so that the grip 1552 and the second wing 1542 can more easily slide past each other. One such friction reducing feature may be a central ridge 1592 on the second wing 1542, which may protrude toward the grip 1552. The central ridge 1592 may abut the grip 1552 in the insertion configuration to reduce the surface area of the second wing 1542 that is in contact with the grip 1552, thereby reducing frictional resistance to sliding motion between the grip 1552 and the second wing 1542. The central ridge 1592 may thus reduce the force required to move the IV catheter system 1500 from the insertion configuration to the fluid delivery configuration, thereby making this transition easier to accomplish with only a single hand.

Figure 15C:
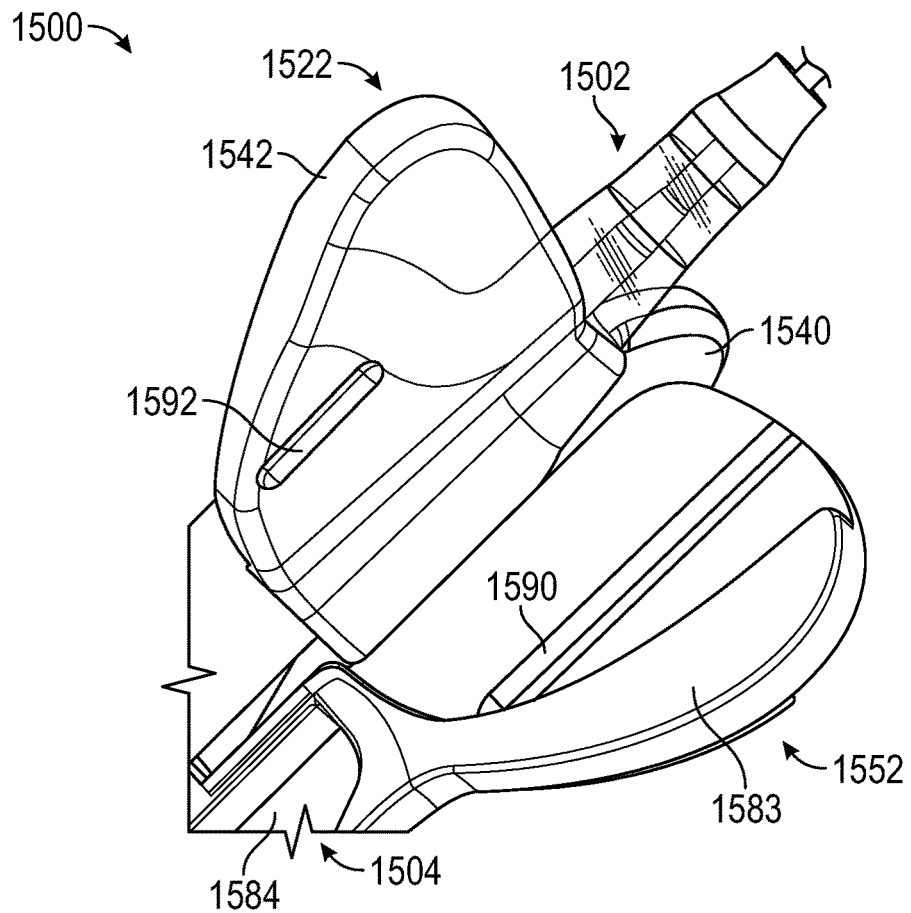
Figure 15D:
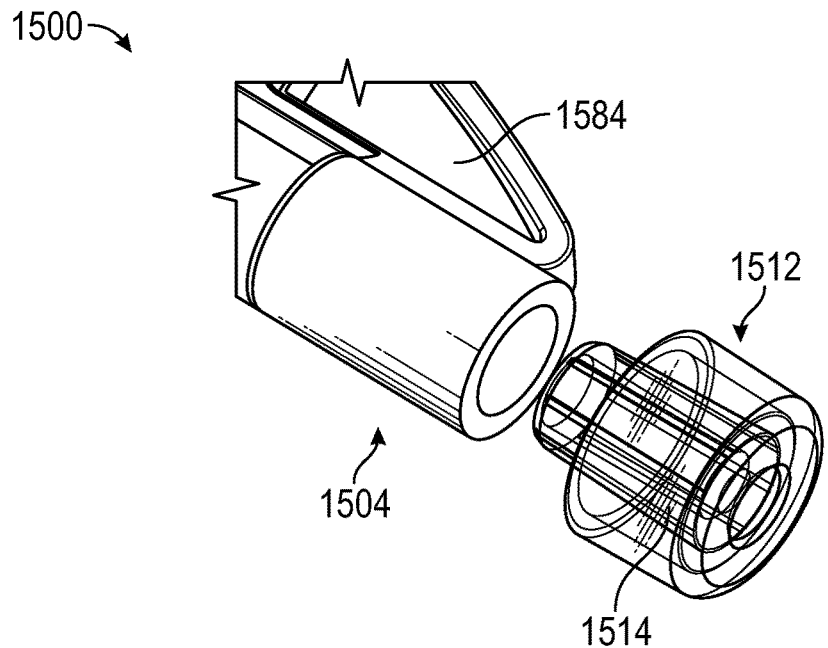

As shown in FIG. 15C, the central ridge 1590 may optionally be aligned with a central trough 1592 formed in the surface of the grip 1552 that faces the second wing 1542. The central trough 1592 may receive the central ridge 1590. Thus, the central ridge 1590 and the central trough 1592 may act as alignment features to maintain alignment between the second wing 1542 and the grip 1552, thereby reducing the likelihood of binding or other resistance to motion to the fluid delivery configuration that could otherwise be caused by misalignment between the catheter component 1502 and the needle component 1504.

FIG. 15C illustrates an open state in which the needle component 1504 is rotated relative to the catheter component 1502 in a manner that positions the grip 1552 substantially perpendicular to the securement platform 1522. In this state, the IV catheter system 1500 may provide alternative ergonomics for inserting the cannula into the fluid delivery location and/or moving the IV catheter system 1500 to the fluid delivery configuration. In this state, the central ridge 1590 may not be positioned within the central trough 1592. However, when the needle component 1504 and catheter component 1502 are again rotated relative to each other to position the IV catheter system 1500 in the compacted state, the central ridge 1590 may enter the central trough 1592 to ensure proper alignment between the needle component 1504 is rotated relative to the catheter component 1502.

The flash component 1512 may indicate proper placement of the cannula of the catheter component 1502. When the cannula penetrates a blood vessel, the resulting blood flow may pass into the catheter component 1502 and through the needle component 1504 to reach the flash component 1512, which may be secured to the proximal end of the needle component 1504. The blood may enter a flash chamber 1514 of the flash component 1512, which may be visible to the user through transparent walls of the flash component 1512.

Various embodiments of the present invention (not shown) further comprise a safety mechanism configured to secure the sharpened, distal tip of the introducer needle following removal and separation of the needle component from the catheter component. A safety mechanism may include any compatible device known in the art. In some instances, the safety mechanism is configured to interact with a needle feature, such as a ferrule, notch, crimp or bump on the needle. The crimp or bump formed in the needle cause a slight out of round configuration that can be used to activate a safety mechanism. In some instance, the safety mechanism comprises an arm or lever that is actuated to capture the needle tip within the mechanism and prevent the tip from emerging prior to safe disposal.

The safety mechanism is attached to the body of the needle and is capable of sliding along the length thereof. In some instances, an initial or assembled position of the safety mechanism is located in proximity to the base or proximal end of the needle component prior to catheterization. For some configurations, the assembled position of the safety mechanism is between the proximal end of the needle hub and the proximal end of the catheter hub or securement platform, wherein the safety mechanism does not overlap the catheter hub or securement platform. In some instances, a portion of the safety mechanism is positioned within the catheter hub, with the balance of the safety mechanism being positioned external to the catheter hub, such as within the needle hub. In some embodiments, a portion of the catheter hub or securement platform is extended proximally to provide a housing in which at least a portion of the safety mechanism is housed. In some instances, the entire safety mechanism is housed within the housing of the catheter hub or securement platform prior to catheterization.

In some embodiments, the assembled position of the safety mechanism positions the proximal end of the catheter hub between the distal end of the safety mechanism and a distal end of a grip of the needle component. In some instances, the assembled position of the safety mechanism positions the proximal end of the catheter hub between the distal end of the safety mechanism and a proximal end of a grip of the needle component. In some instances, a portion of the safety mechanism overlaps a portion of a grip of the needle component. In some embodiments, at least some portion of at least one of the catheter hub and the grip overlaps at least some portion of the safety mechanism. In some embodiments, no portion of the catheter hub or grip overlaps any portion of the safety mechanism.

In some embodiments, a defeatable mechanical connection is provided between the safety mechanism and at least one other component of the IV catheter system. In some embodiments, a distal end of the safety mechanism is selectively coupled to a proximal end of the catheter hub. In one embodiment, the safety mechanism interlocks internally to the proximal end of the catheter hub. In one embodiment, the safety mechanism interlocks externally to the proximal end of the catheter hub. In some embodiments, a distal end of the safety mechanism is selectively coupled to a proximal end of the securement platform. In some embodiments, a surface of the safety mechanism is selectively coupled to at least one surface of at least one of the catheter hub, a blood control valve, an extension tube, and the securement platform. In some instances, the mechanical connection is defeated upon securement of the needle tip within the safety mechanism.

FIGS. 16, 17, 18A, 18B, 19A, and 19B depict various modifications that can be made to many of the IV catheter systems described above. For illustrative purposes, these modifications will be described with reference to IV catheter system 1400 shown in FIGS. 14A and 14B. However, these modifications could equally be made to other IV catheter systems described herein.

Figure 16:
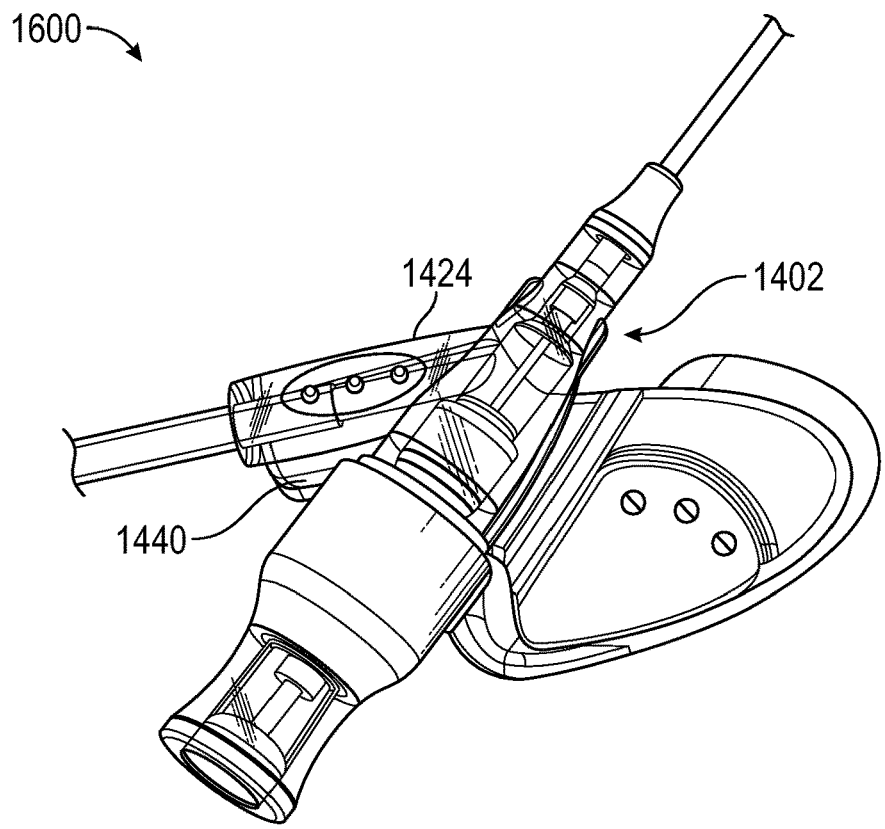
FIG. 16 is a perspective view of an IV catheter system according to various embodiments in which the securement platform includes a wing that extends only between the catheter component and the extension tubing junction.

FIG. 16 illustrates an IV catheter system 1600 that is configured in the same manner as IV catheter system 1400 except that first wing 1440 only extends between catheter component 1402 and extension tubing junction 1424. In other words, in FIG. 16, first wing 1440 does not extend outwardly beyond extension tubing junction 1424. In such embodiments, first wing 1440 may extend between catheter component 1402 and extension tubing junction 1424 to provide reinforcement to extension tubing junction 1424 thereby facilitating the use of extension tubing junction 1424 as a gripping surface during insertion. As indicated above, in many of the other embodiments described, the portion of the first wing that extends beyond the extension tubing junction could also be removed.

Figure 17:
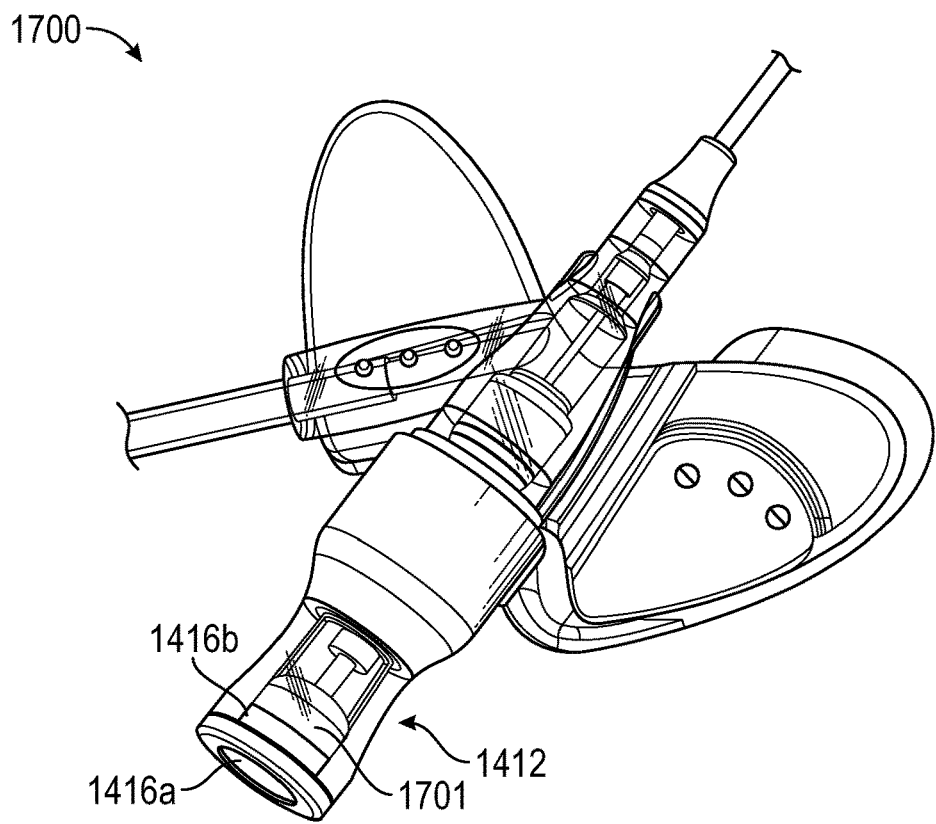
FIG. 17 is a perspective view of an IV catheter system according to yet another alternative embodiment in which a flash component that is incorporated into a needle component includes side vents.

FIG. 17 illustrates an IV catheter system 1700 that is configured in the same manner as IV catheter system 1400 except that flash component 1412 includes a side vent. In particular, as shown in FIG. 17, flash component 1412 can include a proximal vent 1416a as is described above (and labeled 1416 in FIG. 14). Additionally, flash component 1412 can include one or more side vents 1416b that are formed through the sidewall of flash component 1412. These side vents can be positioned proximal to a vent membrane 1701 and provide an alternative or additional venting pathway for air as it exits flash chamber 1412.

When some clinicians insert an IV, they may place their thumb overtop proximal vent 1416a thereby blocking airflow through the vent and minimizing the flow of blood into flash component 1412. Therefore, IV catheter system 1700 can include side vents 1416b which will provide an alternative pathway for airflow in instances where proximal vent 1416a may be blocked. Side vents 1416b can be shaped in any suitable manner. In some embodiments, flash component 1412 could be elongated to accommodate appropriately-sized side vents. Any of the other above-described IV catheter systems that also employ a flash component may also be configured with side vents. In some embodiments, a portion of proximal vent 1416a extends onto the sidewall of flash component 1412 to form side vent 1416b. Thus, the user's thumb may block the portion of proximal vent 1416a located on the proximal end of flash component 1412 without contacting or blocking the portion of the proximal vent located on, and thereby forming side vent 1416b.

Figure 18A:
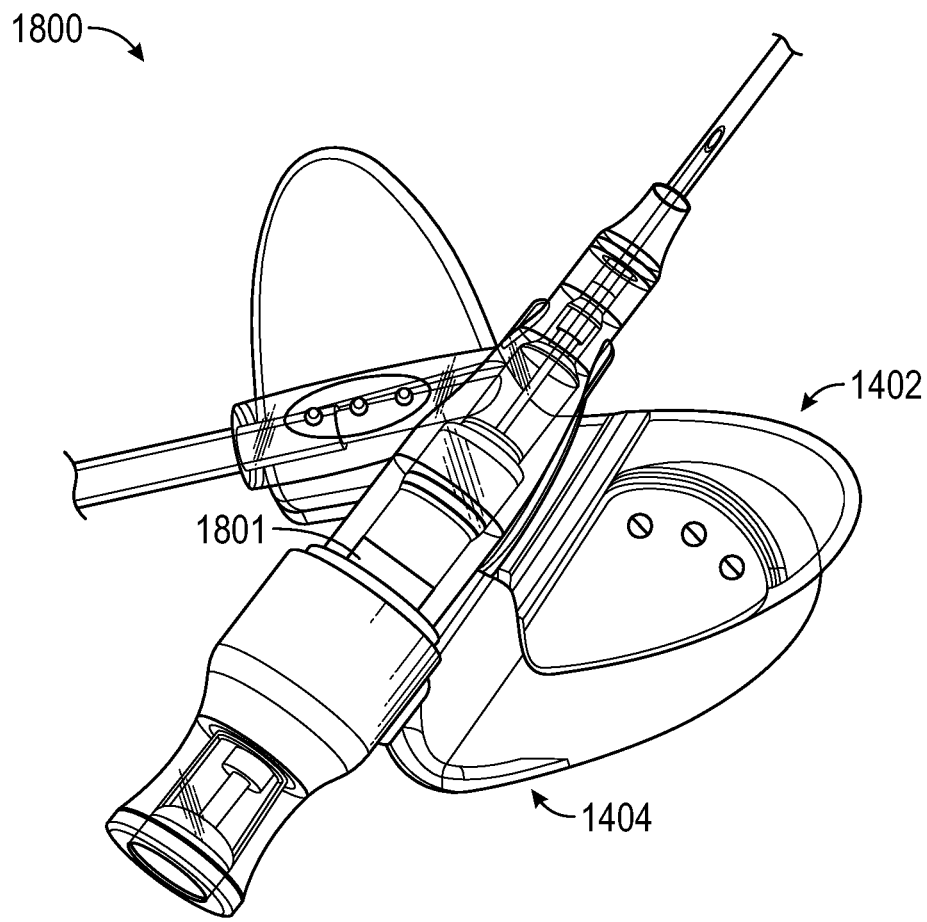
FIGS. 18A and 18B are perspective and side views respectively of an IV catheter system according to various embodiments in which the catheter component includes a visual indicator to provide an indication of when the needle reaches the hooded position.
Figure 18B:
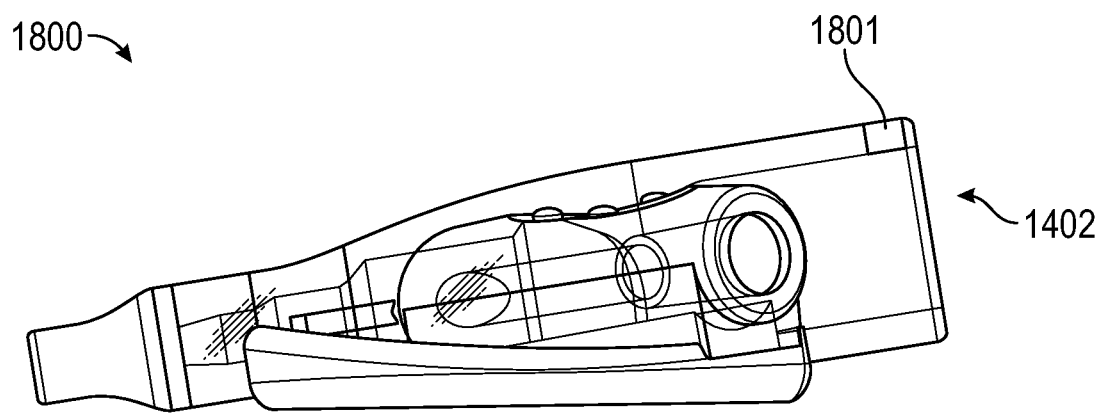

FIGS. 18A and 18B illustrate perspective and side views respectively of an IV catheter system 1800 that is configured in the same manner as IV catheter system 1400 except that catheter component 1402 includes a visual indicator 1801 at a proximal end. Visual indicator 1801 is positioned on catheter component 1402 so that it will be covered by needle component 1404 prior to insertion of the catheter. During the insertion process, needle component 1404 can be slightly withdrawn with respect to catheter component 1402 which would result in the tip of the needle being withdrawn into, or "hooded" within the catheter. The relative positions of catheter component 1402 and needle component 1404 when the needle is in this hooded position are depicted in FIG. 18A.

Once a clinician has inserted the needle into a patient's vein, the clinician will oftentimes withdraw the needle tip into the hooded position before further inserting the catheter. Catheter component 1402 can include visual indicator 1801 as a means of informing the clinician when the needle tip is in the hooded position. In other words, during the initial insertion process, needle component 1404 will be positioned overtop visual indicator 1801 (e.g., similar to what is shown in FIG. 14A). Then, as the clinician slides needle component 1404 backwards away from catheter component 1402, visual indicator 1801 will be revealed as shown in FIG. 18A thereby informing the clinician when the needle tip has reached the hooded position.

In some instances, visual indicator 1801 is located on catheter component 1402 at a position selected to reveal visual indicator 1801 when catheter component 1402 has been removed or withdrawn from the needle adapter a desired distance. For example, in some embodiments the needle tip is hooded within the catheter when catheter component 1402 is removed from the needle adapter a distance of 2 mm. Accordingly, in some embodiments visual indicator 1801 is positioned within the needle adapter at a distance of approximately 2 mm when catheter component 1402 is fully seated within the distal end or opening of the needle adapter.

FIG. 18B provides a side view of catheter component 1402 of IV catheter system 1800 in isolation. As shown, visual indicator 1801 is positioned near a proximal end of catheter component 1402. As indicated above, the exact position of visual indicator 1801 will be dependent on how needle component 1404 and catheter component 1402 overlap. In particular, visual indicator 1801 can be positioned so that it becomes exposed once the needle tip reaches the hooded position but prior to needle component 1404 decoupling from catheter component 1402. In some instances, the exposure occurs after a translational movement of approximately 2 mm. In this way, the clinician can easily separate needle component 1404 from catheter component 1402 to reach the hooded position while still maintaining sufficient coupling between the two components to facilitate further insertion of the catheter.

A visual indicator similar to visual indicator 1801 could be added to any of the above-described IV catheter systems to provide the indication of when the needle has reached the hooded position. Also, in some embodiments, a tactile indicator in place of or in addition to a visual indicator could be employed. For example, needle component 1404 and/or catheter component 1402 may include one or more features (e.g., ridges or grooves) that provide a tactile indication of when the needle has reached the hooded position.

Figure 19A:
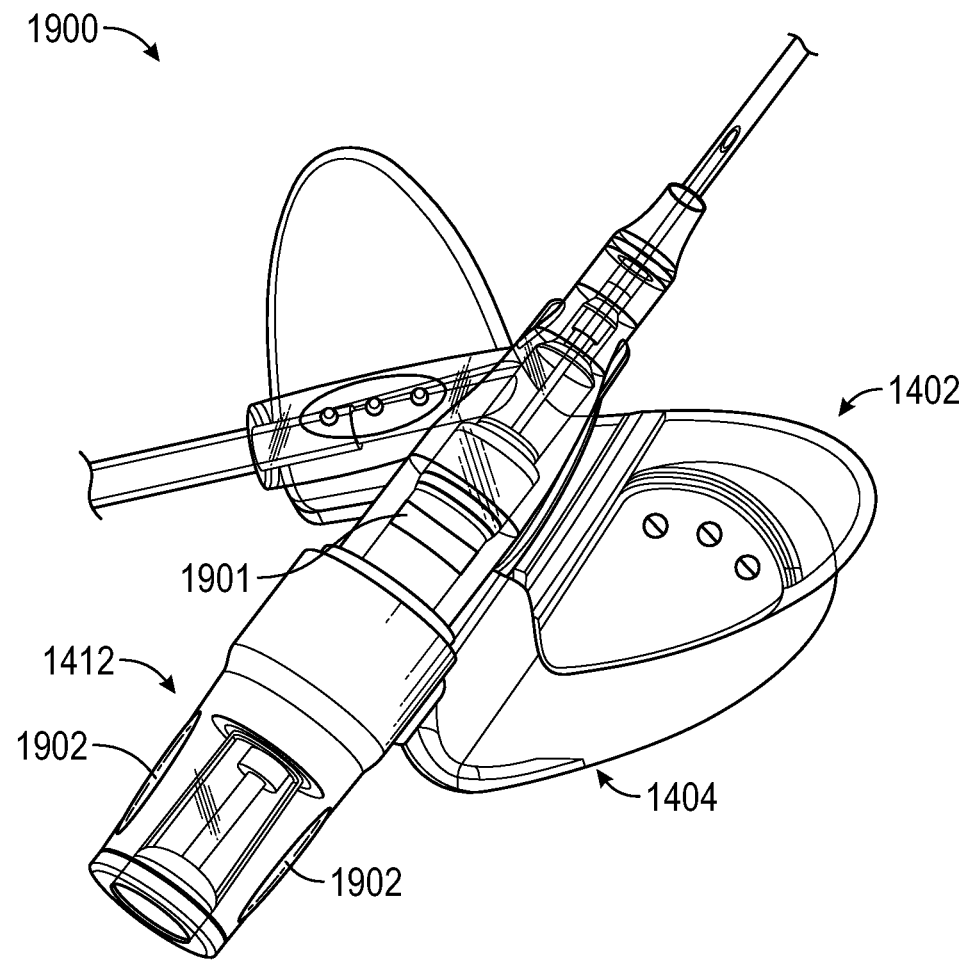
FIGS. 19A and 19B are perspective and side views respectively of an IV catheter system according to various embodiments in which an elongated flash component includes side grips and the catheter component includes a push tab.
Figure 19B:
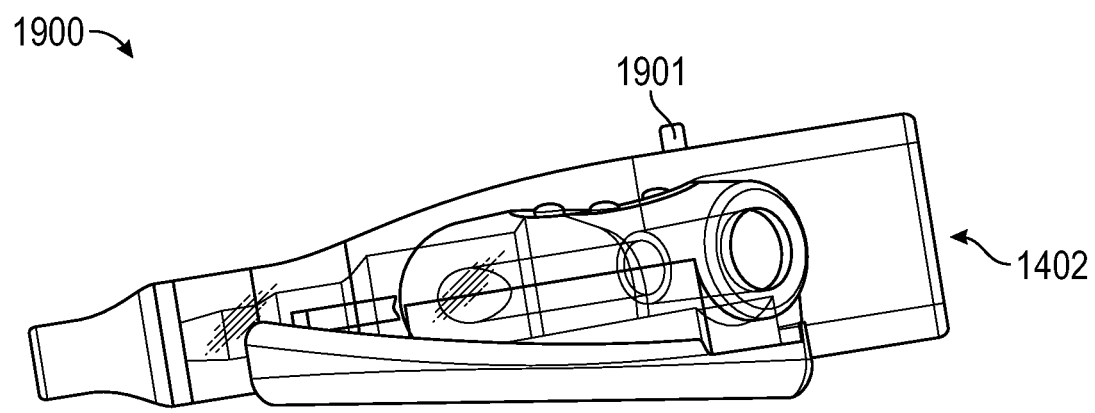

FIGS. 19A and 19B illustrate perspective and side views respectively of an IV catheter system 1900 that is configured in a similar manner as IV catheter system 1400 except that catheter component 1402 and needle component 1404 are configured to facilitate various types of insertion grip techniques. As shown in FIG. 19A, flash component 1412 is elongated in comparison to the flash component depicted in FIG. 14A. Additionally, flash component 1412 includes side grips 1902 which constitute features formed on opposing sides of flash component 1412 which facilitate gripping flash component 1412 between the thumb and middle finger. For example, side grips 1902 can comprise flattened surfaces and/or other types of gripping features such as ridges.

As best seen in FIG. 19B, catheter component 1402 may include a push tab 1901 which extends upwardly from a top surface of catheter component 1402. Push tab 1901 can serve as a surface against which the clinician's index finger may push while gripping side grips 1902 between the thumb and middle finger. The length of flash component 1412 can be configured so that push tab 1901 is spaced from side grips 1902 at a distance corresponding to the average length of a clinician's index finger. The additional length of flash component 1412 can also allow flash to be visualized for a longer period of time. Other IV catheter systems described herein that incorporate a flash component into the needle component may also be configured to include side grips and a push tab in a similar manner as shown in FIGS. 19A and 19B.

Figure 20:
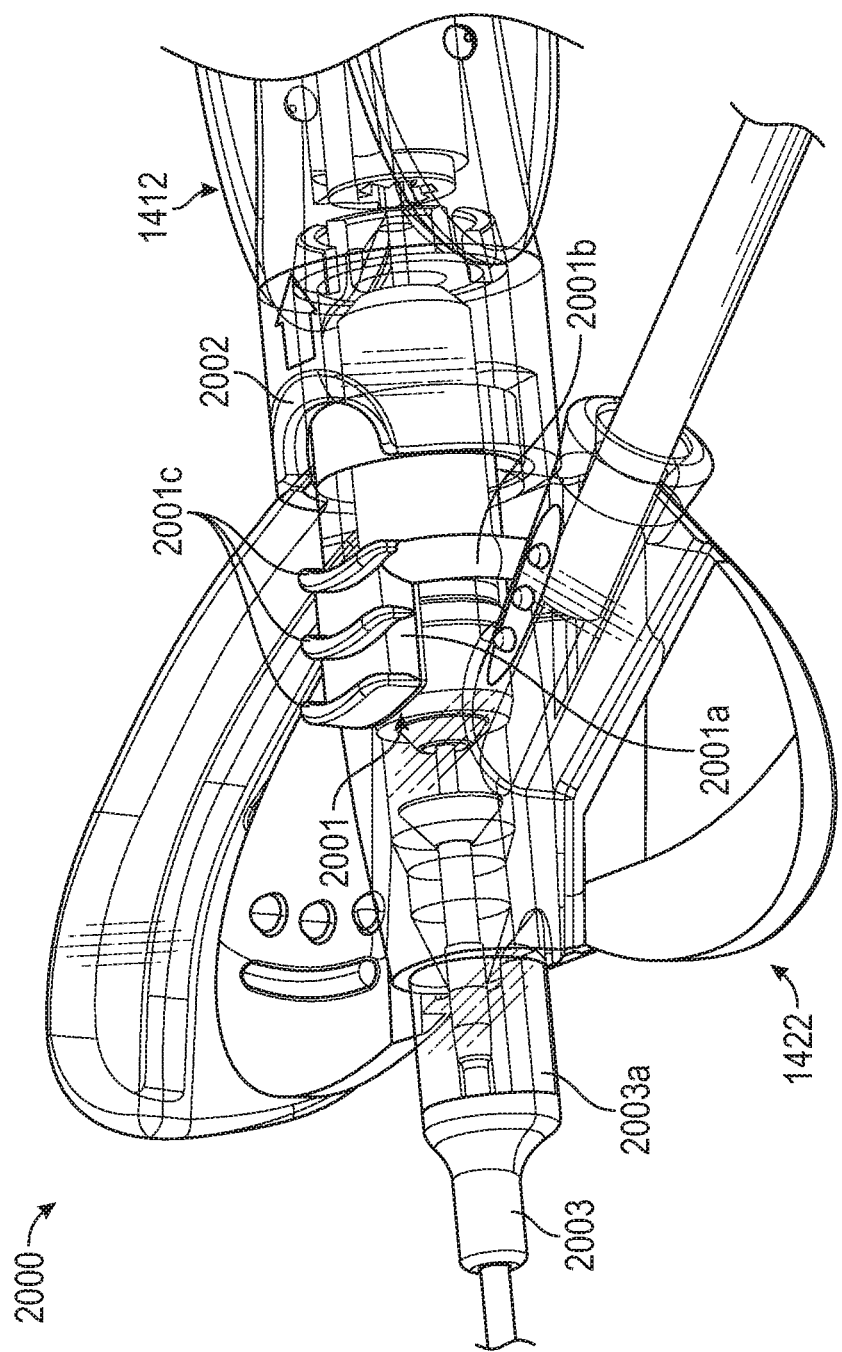
FIG. 20 is a perspective view of an IV catheter system according to various embodiments that provide a number of additional features.

FIG. 20 illustrates an IV catheter system 2000 that is configured in a similar manner as IV catheter system 1400 but with a number of additional features. As with IV catheter system 1400, IV catheter system 2000 includes a catheter component having a securement platform 1422, extension tubing, and a needle component incorporating a flash component 1412. As shown in FIG. 20, IV catheter system 2000 also includes a soft integral push tab 2001, a push tab cut-out 2002, and an integrated strain relief 2003.

Push tab 2001 can be integrally molded from the same material as securement platform 1422. For example, push tab 2001 can include a base 2001a that is positioned on top of and towards the proximal end of the catheter adapter. Base 2001a may be connected to securement platform 1422 by connecting channels 2001b which extend downwardly from base 2001a on both sides of the catheter adapter. Connecting channels 2001b can reinforce base 2001a and can facilitate the molding process. A number of ridges 2001c may extend upwardly from base 2001a and can function as a surface against which a clinician may push while inserting the needle and/or when separating the needle component from the catheter component, such as when hooding the needle during catheterization. In some embodiments, textures and/or indents may be employed in place of or in conjunction with ridges 2001c.

Cut-out 2002 can be formed in a top surface of the distal end of the needle component such that cut-out 2002 will substantially align with base 2001a. Cut-out 2002 therefore creates a region in which the clinician can place his or her finger or thumb to more easily apply a distal force against push tab 2001.

Strain relief 2003 can also be integrally molded from the same material as securement platform 1422. To facilitate molding strain relief 2003, a connecting channel 2003a can be formed between securement platform 1422 and strain relief 2003.

Although push tab 2001 and strain relief 2003 are shown as including connecting channels, each of these features could equally be molded separately from securement platform 1422 (i.e., molded without connecting channels) in some embodiments. Also, each of push tab 2001, cut-out 2002, and strain relief 2003 could be included on any of the other IV catheter systems described herein.

Figure 21:
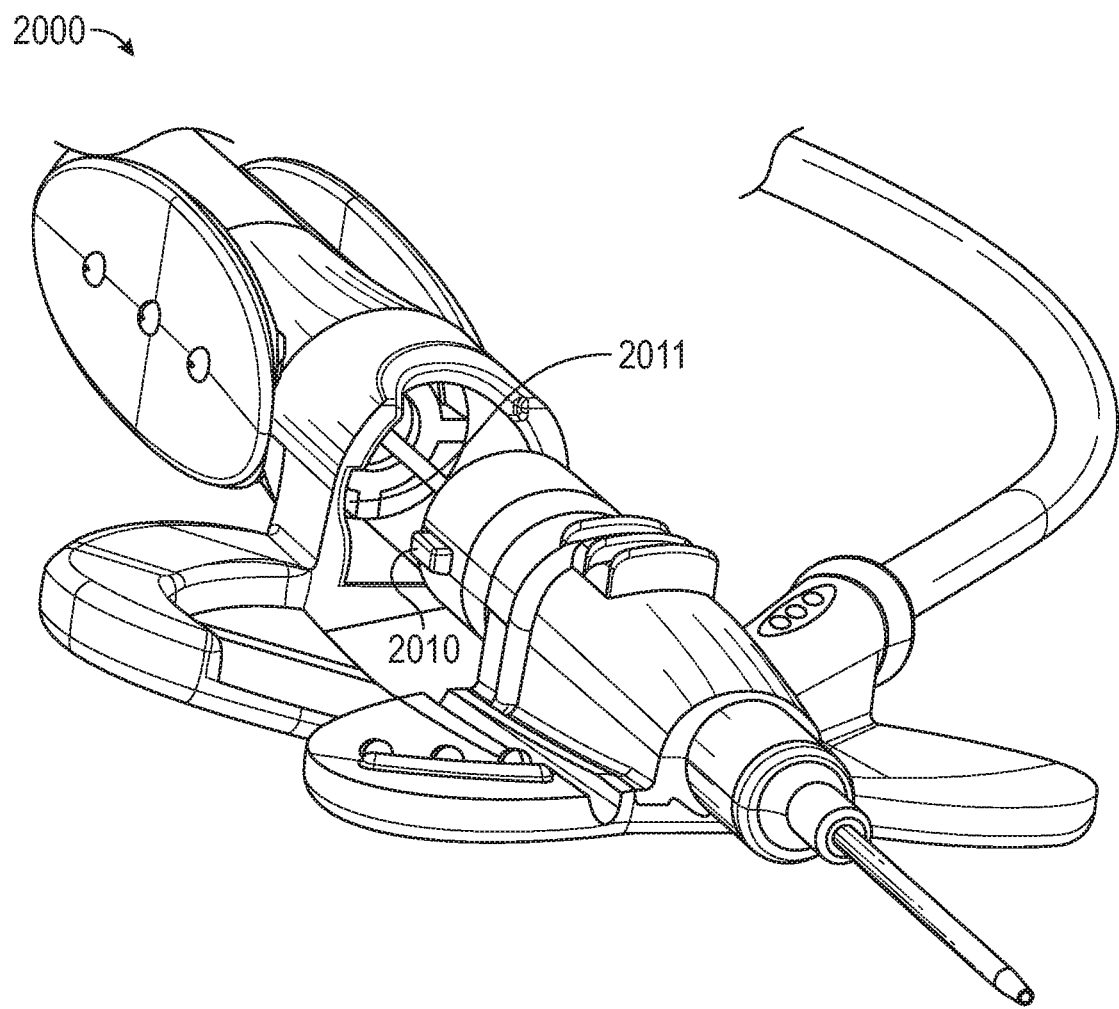
FIG. 21 illustrates an example of an anti-rotation feature that can be employed with one or more embodiments of an IV catheter system.

In some embodiments, IV catheter system 2000 may include an anti-rotation feature. For example, as shown in FIG. 21, this anti-rotation feature can be comprised of a protrusion 2010 formed at a proximal end of the catheter component and a corresponding protrusion 2011 formed within the portion of needle component into which the catheter component inserts. Protrusions 2010 and 2011 can be positioned relative to one another to prevent the wing from being rotated downwardly away from the securement platform.

For example, with reference to the orientation shown in FIG. 21, protrusion 2011 may be configured to contact protrusion 2010 when the wing is oriented directly below the securement platform so that the wing cannot be further rotated in a counterclockwise direction relative to the catheter component. In this way, the wing can be prevented from sagging downward. At the same time, however, the wing will still be able to rotate in a clockwise direction to easily accommodate different grip techniques. This anti-rotation feature could also be included in any of the other embodiments of IV catheter systems described herein.

Figure 22A:
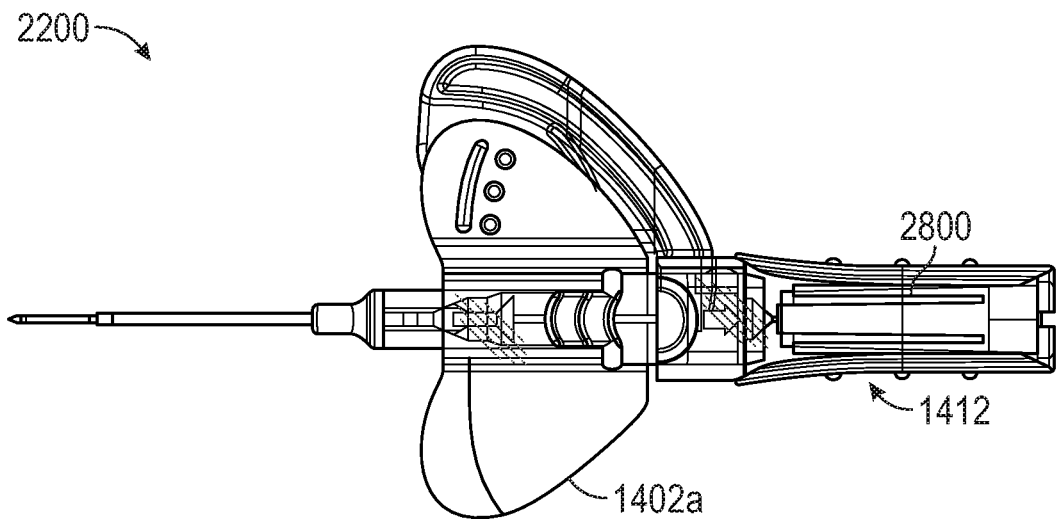
FIGS. 22A and 22B illustrate how many of the disclosed features can be provided on an open IV catheter system.
Figure 22B:
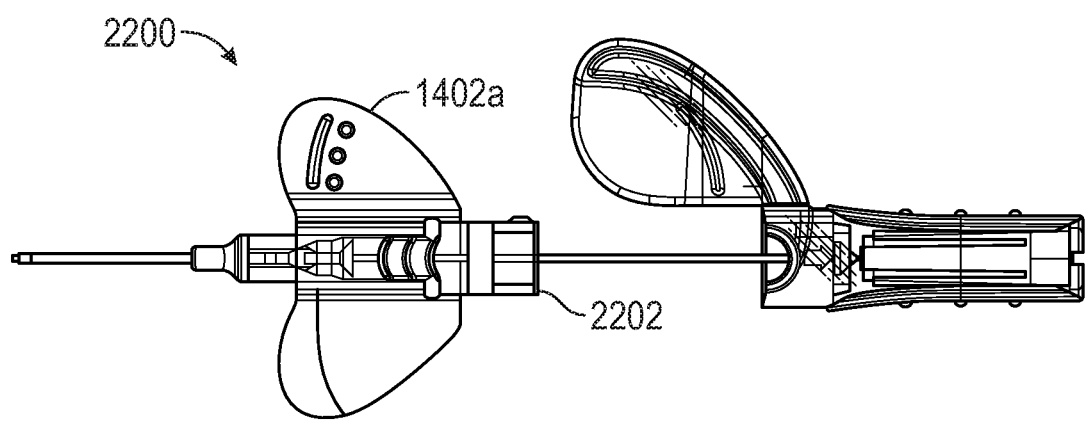

To this point, each of the described IV catheter systems has been a closed system (i.e., a system that includes extension tubing). It is noted, however, that many of the above described features can equally be implemented on an open IV catheter system (i.e., a system that does not include extension tubing). FIGS. 22A and 22B illustrate an example of an open IV catheter system 2200 that is otherwise substantially the same as IV catheter system 2000. As shown, IV catheter system 2200 includes a catheter component 1402a that does not incorporate extension tubing. Because it is an open system, catheter component 1402a can be configured to provide intravascular access once the needle component has been removed. For example, catheter component 1402a can include an internal, blood control feature, whether single use or multi-use (not shown), and a threaded luer connection 2202 to thereby allow other devices to be coupled to the catheter component. Alternatively, catheter component 1402a may not include a blood control feature.

IV catheter system 2200 is shown as including a flash chamber 1412 that includes a path-defining structure 2800. Any of the above described IV catheter systems, whether open or closed, can employ a path-defining structure 2800 within the flash chamber to enhance the visualization of proper catheter placement. More particularly, a path-defining structure can cause blood to flow through the flash chamber at a more controlled rate that facilitates identifying when the catheter is properly positioned within the vasculature.

Figure 23:
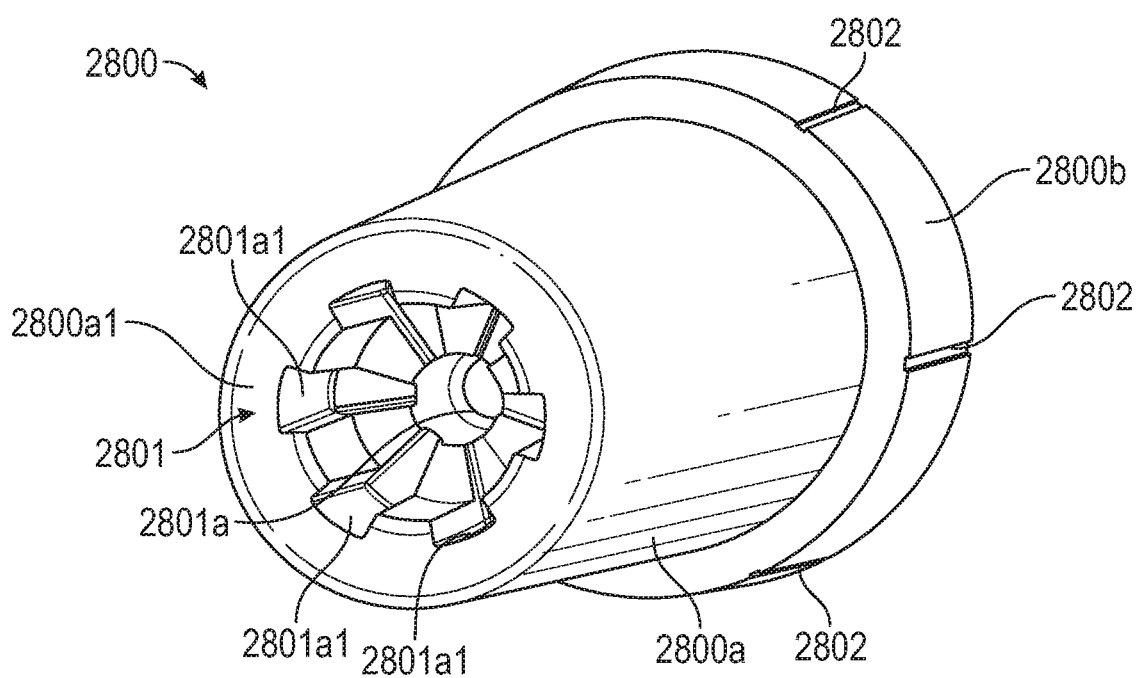
FIG. 23 illustrates a path-defining structure that can be employed within a flash chamber in embodiments of an IV catheter system.

FIG. 23 illustrates path-defining structure 2800 in isolation. Path-defining structure 2800 includes a distal portion 2800a and a proximal portion 2800b. In some embodiments, proximal portion 2800b can have an outer dimension that substantially matches an inner dimension of a proximal end of flash component 1412 such that a fluid-tight seal is formed between the two components. Proximal portion 2800b can include venting grooves 2802 which are sized to allow air, but not fluid, to escape from within flash component 1412. In other words, proximal portion 2800b can function as a vent plug.

Figure 24A:
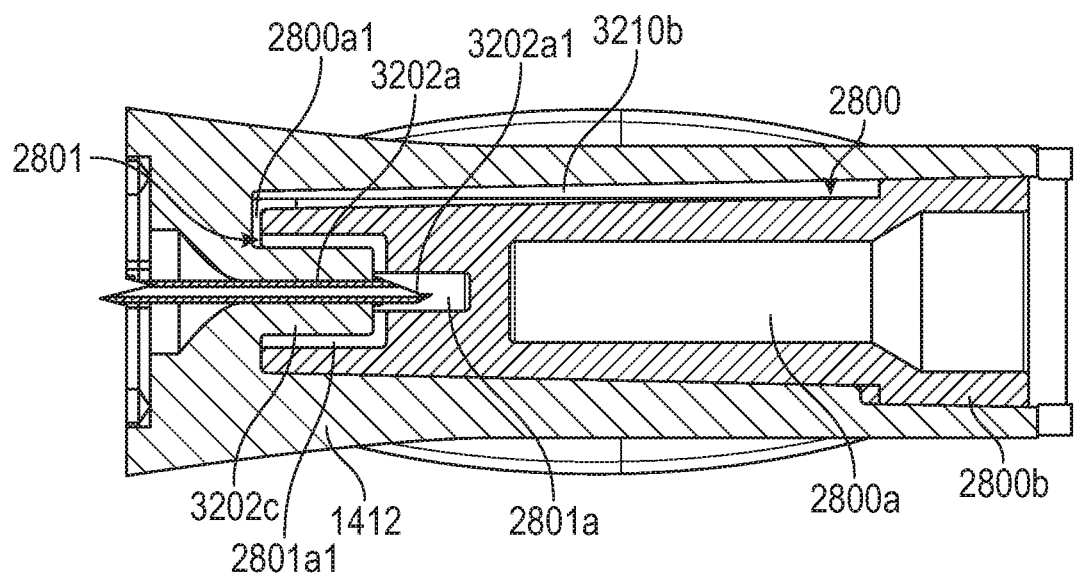
FIGS. 24A-24E each illustrate a cross-sectional view of a flash chamber that includes the path-defining structure of FIG. 23.

Distal portion 2800a can have a reduced outer dimension compared to the outer dimension of proximal portion 2800b. The inner dimension of a chamber 3210b of flash component 1412 (see FIG. 24A) with respect to the outer dimension of distal portion 2800a can also be configured such that a spacing or channel will exist between distal portion 2800a and the inner wall of chamber 3210b only along the top of flash component 1412. For example, as shown in FIG. 24A, with path-defining structure 2800 inserted into chamber 3210b, a channel will exist above path-defining structure 2800. However, around the remaining portions of path-defining structure 2800, the outer surface of distal portion 2800a can contact the inner wall of chamber 3210b. In this way, blood/fluid will only be allowed to flow along the outer surface of distal portion 2800a within the channel. Since this channel is formed along the top of flash component 1412, which will be oriented towards the clinician during insertion, the clinician will be able to visualize the rate of blood flow.

To allow blood to flow from the proximal end of needle 3202a into this channel, an opening 2801 can be formed in a distal end 2800a1 of distal portion 2800a as is best shown in FIG. 24A. Opening 2801 can include a central portion 2801a that extends further into distal portion 2800a then the remainder of opening 2801. The proximal end (or at least a proximal opening) of needle 3202a can be positioned within this central portion 2801a. A number of leaking channels 2801a1 can be symmetrically spaced around an inner surface of opening 2801 and can extend from distal end 2800a1 to central portion 2801a. Any of leaking channels 2801a1 can serve as a fluid pathway by which blood escaping the proximal end of needle 3202a can flow from central portion 2801a towards the channel formed above path-defining structure 2800.

Figure 24B:
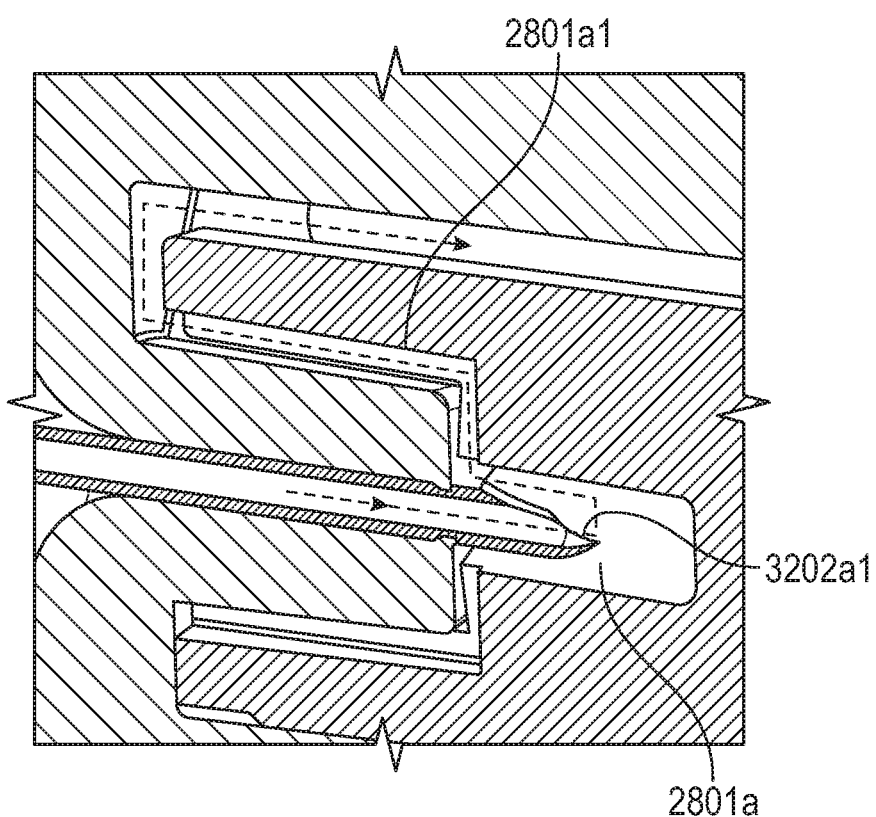

Leaking channels 2801a1 can be symmetrically spaced around opening 2801 to thereby allow path-defining structure 2800 to be inserted into chamber 3210b in any orientation. In other words, regardless of the orientation of path-defining structure 2800, at least one leaking channel 2801a1 will be positioned in an upward orientation and will intersect with the channel to thereby provide a pathway to the channel. As shown in FIG. 24A, the inner surface of chamber 3210b can be shaped such that the channel will wrap around distal end 2800a1 at the top of chamber 3210b (i.e., a gap will exist between a top portion of distal end 2800a1 and the inner surface of chamber 3210b). Accordingly, as represented by the arrow in FIG. 24B, blood can flow out of needle 3202a via opening 3202a1 and into central portion 2801a. Then, although the blood may flow into each of leaking channels 2801a1, a fluid pathway will only be provided between the leaking channel that is oriented upward due to distal end 2800a1 contacting the inner wall of chamber 3210b where the other leaking channels are positioned. Therefore, as the blood fills central portion 2801a and leaking channels 2801a1, it will ultimately flow around the top portion of distal end 2800a1 and then proximally within the channel.

Figure 24C:
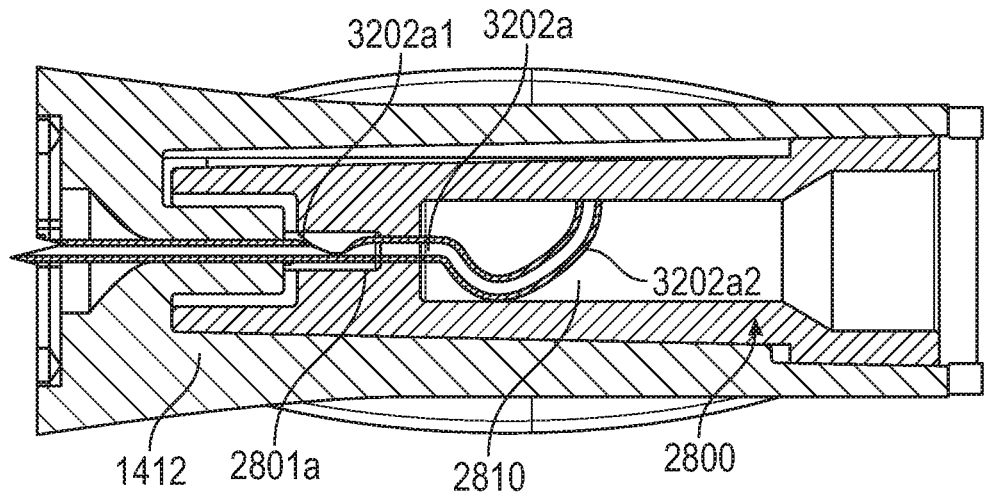

To secure needle 3202a and to ensure that opening 3202a1 remains positioned within central portion 2801a, various techniques can be employed. For example, in FIG. 24C, needle 3202a is shown as having a proximal portion 3202a2 that extends proximally beyond opening 3202a1 and through a proximal wall of central portion 2801a. In this embodiment, path-defining structure 2800 includes a proximal chamber 2810 opposite central portion 2801a within which proximal portion 3202a2 of needle 3202a is positioned. Proximal portion 3202a2 can be curled or otherwise altered to prevent it from being pulled distally through the passageway between central portion 2801a and proximal chamber 2810. Also, in some embodiments, adhesive potting may be deposited within proximal chamber 2810 around proximal portion 3202a2 to further secure proximal portion 3202a2. In such embodiments, the adhesive potting may additionally seal the passageway to prevent blood from flowing into proximal chamber 2810. Alternatively, the passageway may be sized such that proximal portion 3202a2 alone blocks fluid flow into proximal chamber 2810.

Figure 24D:
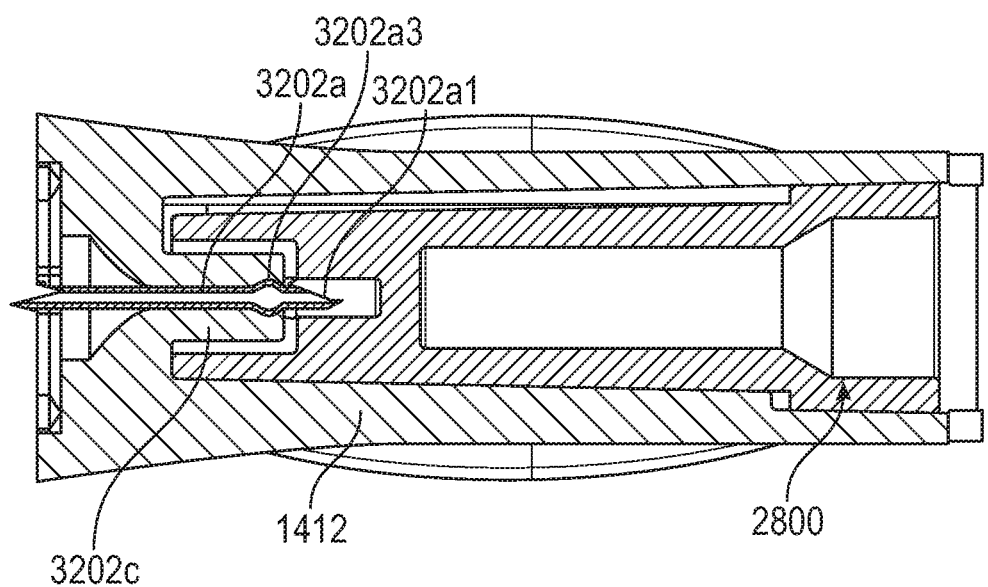

FIG. 24D illustrates an alternate embodiment for securing needle 3202a in position. As shown, needle 3202a may include a bumped area 3202a3 that has an outer dimension sufficient to prevent needle 3202a from being pulled through needle retaining portion 3202c. Bumped area 3202a3 can be positioned relative to opening 3202a1 so that opening 3202a1 remains positioned within central portion 2801a. In some embodiments, needle retaining portion 3202c may include a recessed section into which bumped area 3202a3 can be positioned to further prevent area 3202a from moving in a proximal or distal direction.

Figure 24E:
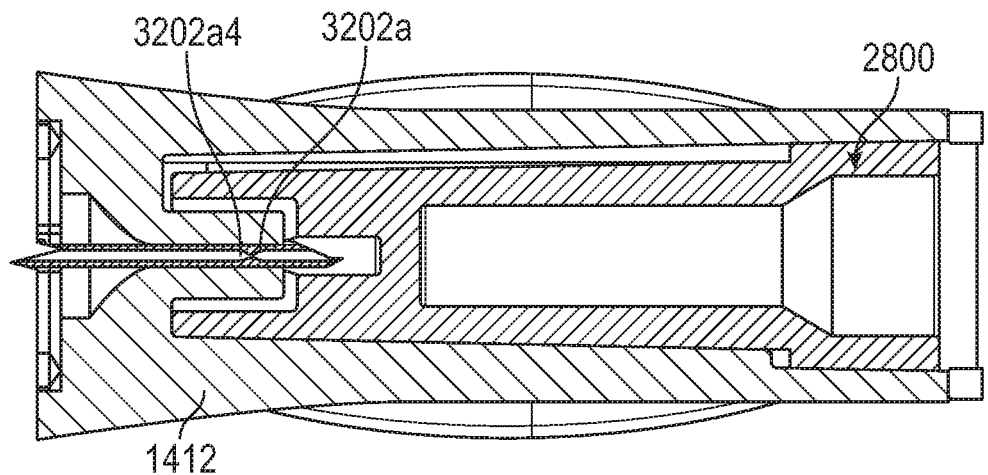

In some embodiments, needle 3202a may be modified to reduce the rate at which blood will flow through the needle. For example, in FIG. 24E, needle 3202a is shown as having a crimp 3202a4 towards its proximal end. Crimp 3202a4 reduces the inside dimension of needle 3202a thereby slowing the rate at which blood will flow into central portion 2801a. Reducing the rate of blood flow into central portion 2801a will likewise reduce the rate of blood flow along the channel formed above path-defining structure 2800 thereby facilitating identifying when needle 3202a has been properly positioned within the patient.

Figure 25A:
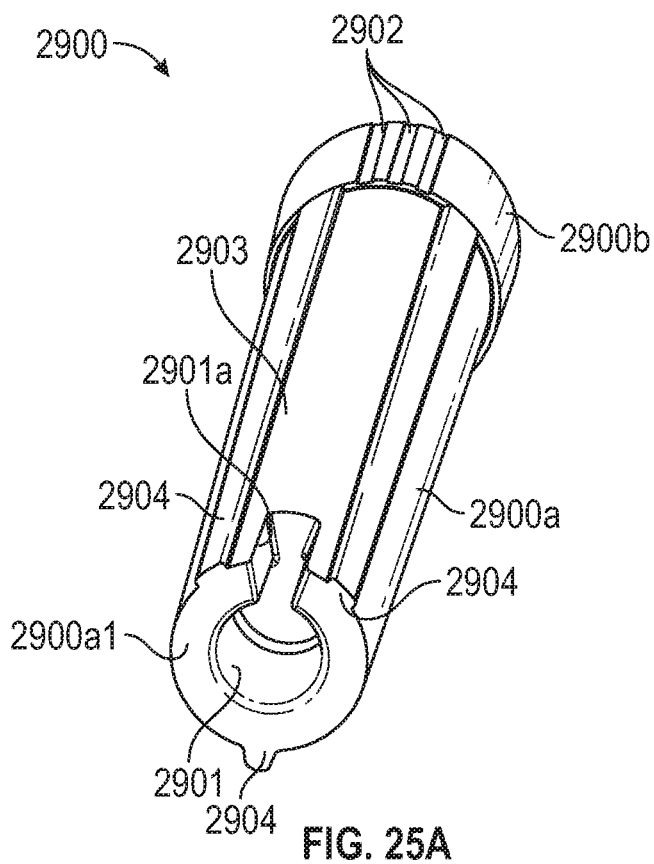
FIGS. 25A and 25B illustrate another path-defining structure that can be employed within a flash chamber in embodiments of an IV catheter system.
Figure 25B:
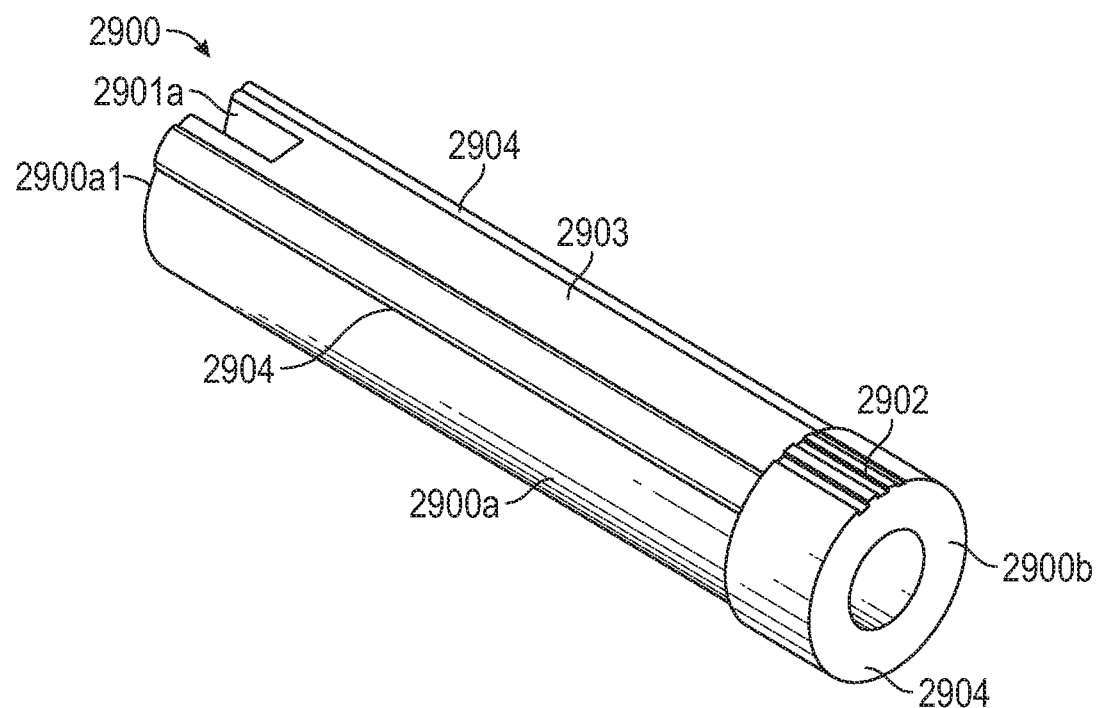

FIGS. 25A and 25B illustrate another embodiment of a path-defining structure 2900 that can function in a similar manner as path-defining structure 2800. In particular, path-defining structure 2900 can be configured to cause blood to flow along a visualization channel formed at the top of flash component 1412.

Path-defining structure 2900 can include a distal portion 2900a and a proximal portion 2900b. Proximal portion 2900b can include venting grooves 2902 that function to vent air but not blood from a proximal end of flash component 1412. Unlike distal portion 2800a of path-defining structure 2800, distal portion 2900a of path-defining structure 2900 is not configured to be oriented at any position within flash component 1412. Instead, distal portion 2900a can include a visualization channel 2903 and various alignment ribs 2904 that are configured for a particular orientation. The inner surface of chamber 3210b can be configured to accommodate alignment ribs 2904 in such a manner that path-defining structure 2900 will be oriented with visualization channel 2903 facing upwards. For example, chamber 3210b could include lengthwise grooves or tabs which interface with alignment ribs 2904 to require insertion of path-defining structure 2900 in the correct orientation and to prevent rotation.

Figure 25C:
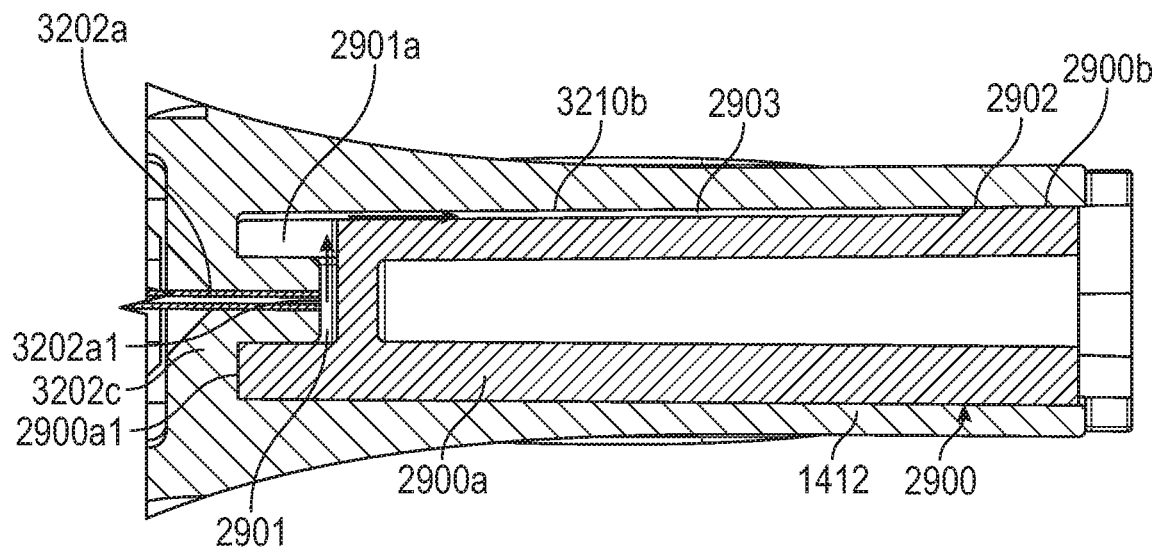
FIG. 25C illustrates a cross-sectional view of a flash chamber that includes the path-defining structure of FIGS. 25A and 25B.

Distal portion 2900a of path-defining structure 2900 can include a distal end 2900a1 having an opening 2901. A leaking channel 2901a can extend between opening 2901 and visualization channel 2903. In a similar manner as described above, blood can flow out of opening 3202a1 into opening 2901 through leaking channel 2901a and into visualization channel 2903 as represented by the arrows in FIG. 25C. Although not depicted in this embodiment, the various configurations of needle 3202a shown in FIGS. 24C-24E can also be employed in conjunction with path-defining structure 2900.

Figure 26:
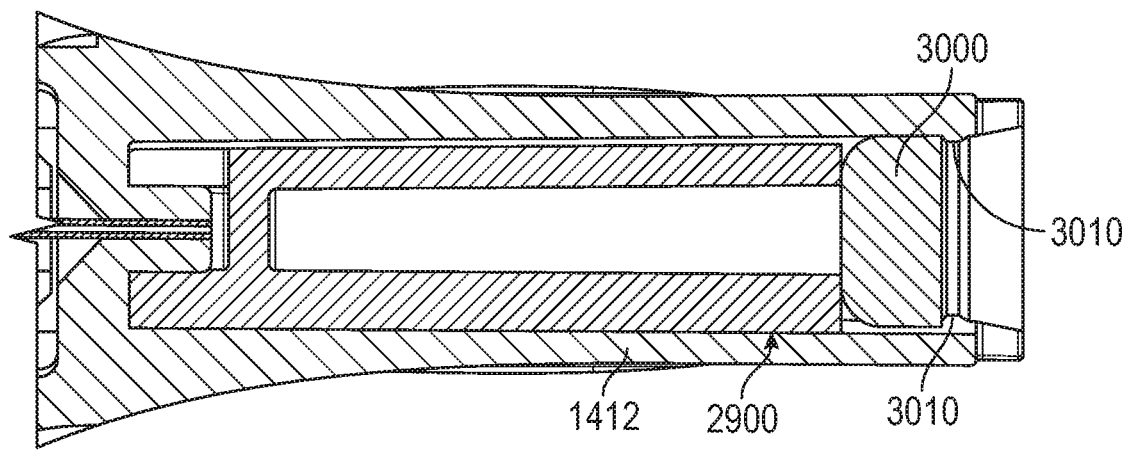
FIG. 26 illustrates how a vent plug can be employed in conjunction with a path-defining structure.

FIG. 26 illustrates an embodiment of a flash component 1412 in which a vent plug 3000 is employed in place of proximal portion 2900b. Also, although not shown, vent plug 3000 could equally be employed in place of proximal portion 2800b. As depicted in FIG. 26, vent plug 3000 is separate from and positioned proximally to path-defining structure 2900. Vent plug 3000 can primarily function to vent air but block fluid. However, in some embodiments, vent plug 3000 may also be configured to secure path-defining structure 2800/2900 in place. For example, flash component 1412 can include protrusions 3010 that are positioned proximally to vent plug 3000 when vent plug 3000 is inserted into chamber 3210b. Protrusions 3010 can prevent vent plug 3000, and therefore path-defining structure 2800/2900, from moving proximally within chamber 3210b.

Figure 27A:
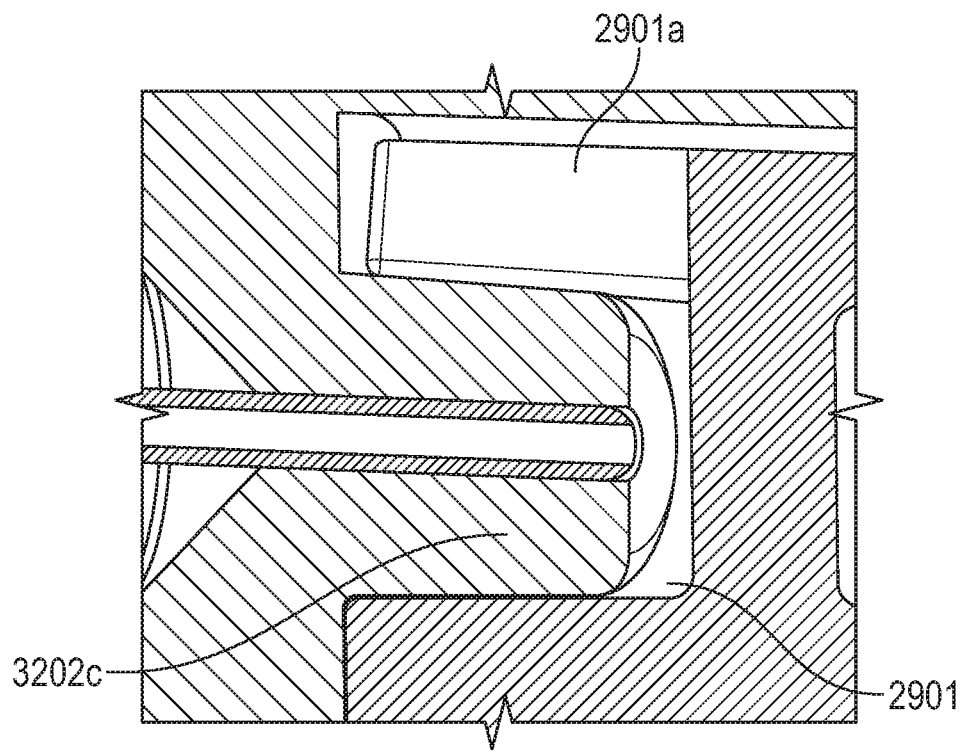
FIGS. 27A-27C each illustrate different ways in which a path-defining structure can be secured within a flash chamber.
Figure 27B:
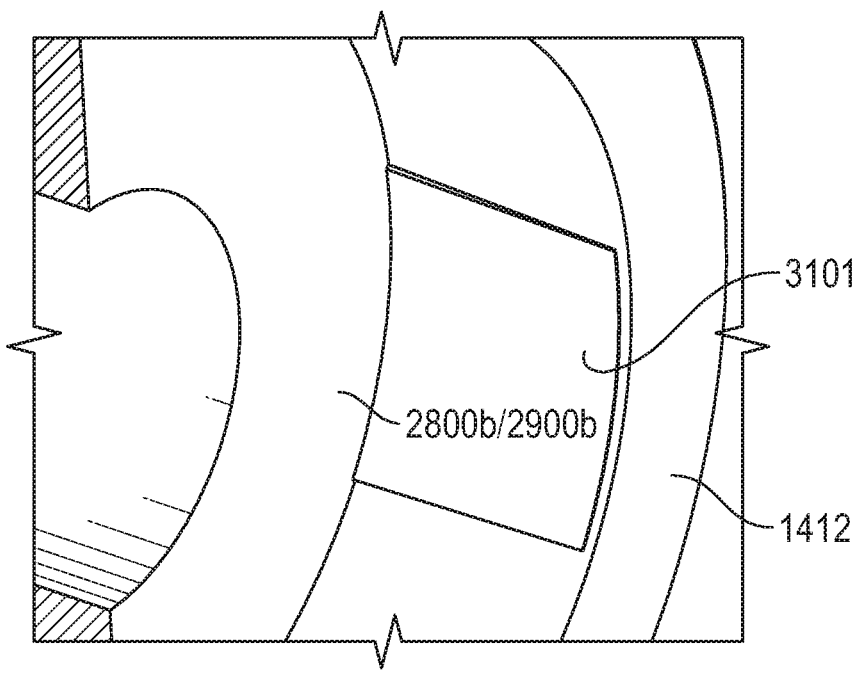
Figure 27C:
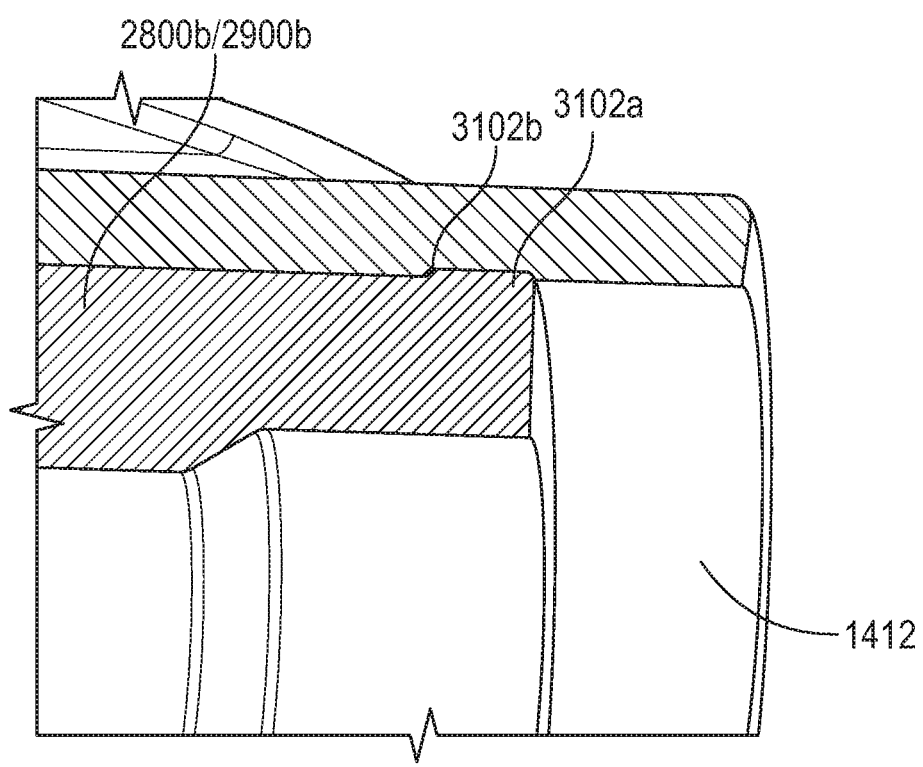

FIGS. 27A-27C each represent a different way in which path-defining structure 2800 or 2900 could be secured within chamber 3210b. In FIG. 27A, opening 2901 is shown as having an inner dimension that corresponds closely with the outer dimension of needle retaining portion 3202c such that a press-fit interface is formed. Opening 2801 could equally be configured in this manner. Alternatively, opening 2801/2901 could be molded overtop needle retaining portion 3202c.

In FIGS. 27B and 27C, path-defining structure 2800/2900 can be retained within chamber 3210b using an interface between proximal portion 2800b/2900b and an inner surface of chamber 3210b. In FIG. 27B, chamber 3210b can include a sloped retention bump 3101. The slope of bump 3101 can cause a distal facing ledge to be formed against which a proximal end of proximal portion 2800b or 2900b contacts. This sloping facilitates inserting path-defining structure 2800 or 2900 but prevents it from being later withdrawn.

FIG. 27C illustrates an example where proximal portion 2800b or 2900b includes a retention rib 3102a which inserts into a retention trench 3102b formed on an inner surface of chamber 3210b. During assembly, path-defining structure 2800 or 2900 can be inserted into chamber 3210b until retention rib 3102a inserts into retention trench 3102b. At this point, retention rib 3102a will prevent the path-defining structure from being proximally withdrawn.

Figure 28A:
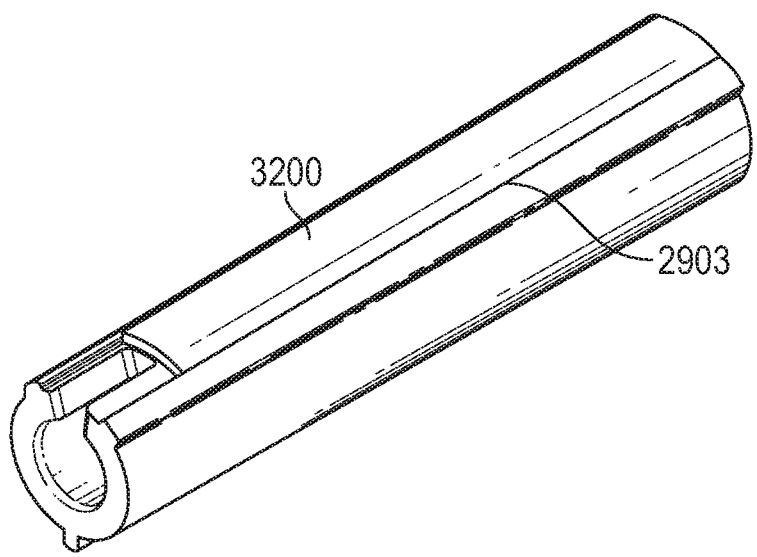
FIGS. 28A and 28B illustrate how a path-defining structure can include a porous material.
Figure 28B:
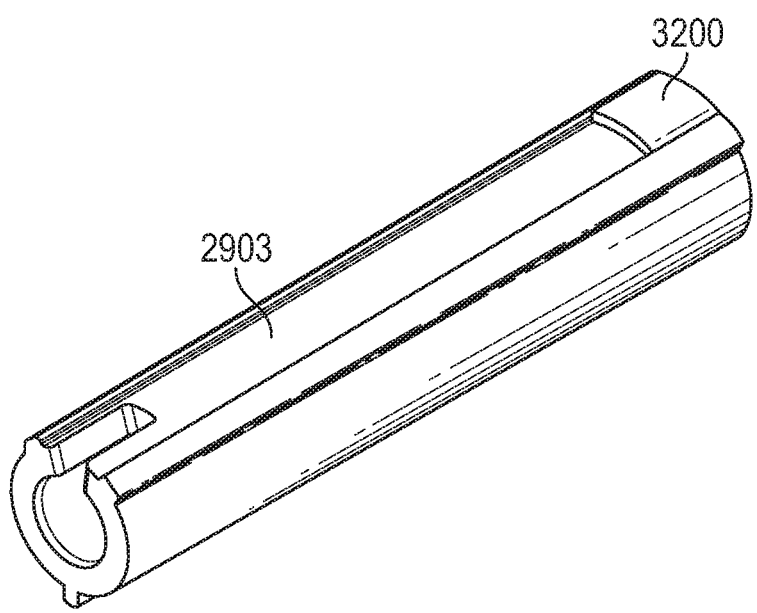

In some embodiments, a porous material could be employed within the channel created by the path-defining structure. For example, in FIG. 28A, a porous material 3200 can be fabricated into visualization channel 2903 and extend through the portion of proximal portion 2900b that includes venting grooves 2902. Porous material 3200 can function to vent air while also wicking the blood at a rate that will be easily visualized. Alternatively, porous material 3200 may only be positioned within the portion of proximal portion 2900b as shown in FIG. 28B.

Figure 29:
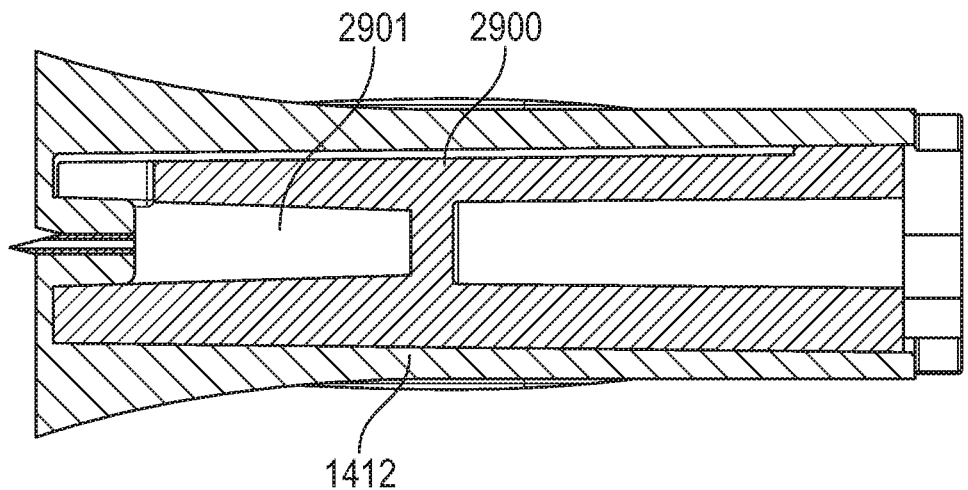
FIG. 29 illustrates how a path-defining structure can be altered to delay when visual confirmation of proper catheter placement is provided.
Figure 30:
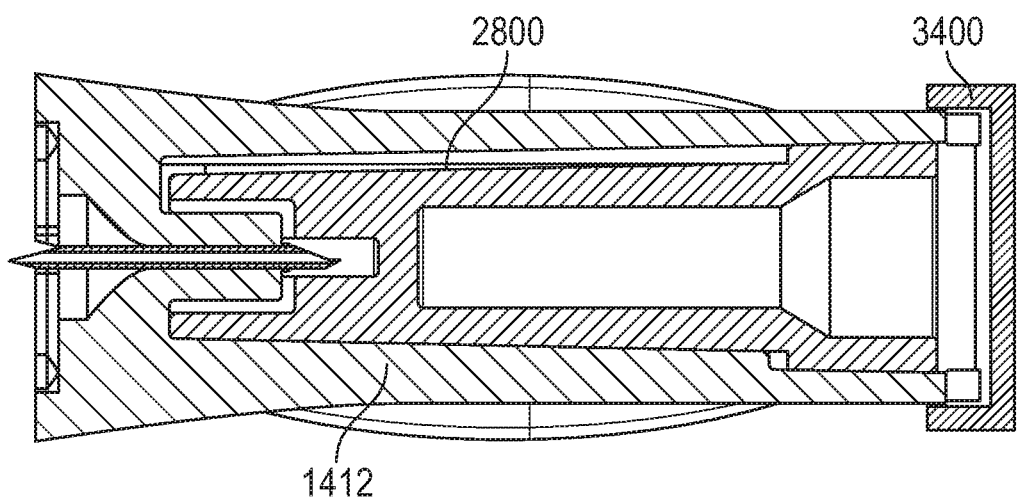
FIG. 30 illustrates how a sealing cap can be employed on a flash chamber to prevent saline from flowing into the flash chamber when an IV catheter system is pre-primed.

FIGS. 29 and 30 each depict additional variations that can be made to embodiments that employ either path-defining structure 2800 or 2900. In FIG. 29, opening 2901 is shown having a larger depth. With this larger depth, more fluid volume will be required before blood will flow through the channel. Accordingly, the depth of opening 2801 or 2901 can be selected to generally control when visual feedback of proper vein confirmation will be provided. In FIG. 30, a sealing cap 3400 is positioned overtop the proximal opening of flash component 1412. Sealing cap 3400 can block the flow of air until removed. Therefore, sealing cap 3400 can be employed in situations where an extension tube is pre-primed with saline to prevent the saline from flowing proximally into flash component 1412. More specifically, with sealing cap 3400 in place, the saline will only be allowed to flow distally within needle 3202a. After insertion of the needle, sealing cap 3400 can be removed to allow flash component 1412 to be employed in the manner described above.

Various embodiments of the present invention further comprise a safety mechanism configured to secure the sharpened, distal tip of the introducer needle following removal and separation of the needle hub from the catheter adapter. A safety mechanism may include any compatible device known in the art. In some instances, the safety mechanism is configured to interact with a needle feature, such as a ferrule, notch, crimp or bump on the cannula. The crimp or bump formed in the cannula causes a slight out of round configuration that can be used to activate a safety mechanism. In some instance, the safety mechanism comprises an arm or lever that is actuated to capture the needle tip within the mechanism and prevent the tip from emerging prior to safe disposal.

The safety mechanism is attached to the body of the needle and is capable of sliding along the length thereof. In some instances, an initial or assembled position of the safety mechanism is located in proximity to the base or proximal end of the catheter adapter prior to catheterization. For some configurations, the assembled position of the safety mechanism is between the proximal end of the needle hub and the proximal end of the catheter adapter or stabilization platform, wherein the safety mechanism does not overlap the catheter adapter or stabilization platform. In some instances, a portion of the safety mechanism is positioned within the catheter adapter, with the balance of the safety mechanism being positioned external to the catheter adapter, such as within the needle hub. In some embodiments, a portion of the catheter adapter or stabilization platform is extended proximally to provide a housing in which at least a portion of the safety mechanism is housed. In some instances, the entire safety mechanism is housed within the housing of the catheter adapter or stabilization platform prior to catheterization.

In some embodiments, the assembled position of the safety mechanism positions the proximal end of the catheter adapter between the distal end of the safety mechanism and a distal end of a paddle grip of the needle hub. In some instances, the assembled position of the safety mechanism positions the proximal end of the catheter adapter between the distal end of the safety mechanism and a proximal end of a paddle grip of the needle hub. In some instances, a portion of the safety mechanism overlaps a portion of a paddle grip of the needle hub. In some embodiments, at least some portion of at least one of the catheter adapter and the paddle grip overlaps at least some portion of the safety mechanism. In some embodiments, no portion of the catheter adapter or paddle grip overlaps any portion of the safety mechanism.

In some embodiments, a defeatable mechanical connection is provided between the safety mechanism and at least one other component of the access device. In some embodiments, a distal end of the safety mechanism is selectively coupled to a proximal end of the catheter adapter. In one embodiment, the safety mechanism interlocks internally to the proximal end of the catheter adapter. In one embodiment, the safety mechanism interlocks externally to the proximal end of the catheter adapter. In some embodiments, a distal end of the safety mechanism is selectively coupled to a proximal end of the stabilization platform. In some embodiments, a surface of the safety mechanism is selectively coupled to at least one surface of at least one of the catheter adapter, a blood control valve, an extension tube, and the stabilization platform. In some instances, the mechanical connection is defeated upon securement of the needle tip within the safety mechanism.

In some embodiments, a particular catheter device, such as, for example, the catheter device of any of the FIGS. 1-30, may include a needle safety mechanism. The safety mechanism may include any safety mechanism configured to secure a sharpened, distal tip of an introducer needle when the needle is withdrawn from a catheter of the particular catheter device, preventing accidental needle sticks.

The safety mechanism may be coupled with the particular catheter device in any number of ways. In some embodiments, the safety mechanism may include an internal interlock in which the safety mechanism is coupled with an internal surface of a catheter adapter. Coupling may include threading, fitting, snapping, connecting, attaching, fastening, clipping, hooking, or any other suitable means of coupling. Non-limiting examples of safety mechanisms that include an internal interlock are provided in: U.S. Pat. No. 8,496,623, titled BI-DIRECTIONAL CANNULA FEATURE CAPTURE MECHANISM, filed Mar. 2, 2009; U.S. Pat. No. 9,399,120, titled BI-DIRECTIONAL CANNULA FEATURE CAPTURE MECHANISM, filed Jul. 11, 2013; U.S. Patent Application No. 62/314,262, titled CANNULA CAPTURE MECHANISM, filed Mar. 28, 2016, each of which is herein incorporated by reference in its entirety. In some embodiments, the safety mechanism may include a clip disposed within the catheter adapter, a non-limiting example of which is provided in U.S. Pat. No. 6,117,108, titled SPRING CLIP SAFETY IV CATHETER, filed Jun. 12, 1998, which is herein incorporated by reference in its entirety.

In some embodiments, the safety mechanism may include an external interlock in which the safety mechanism is coupled with an external surface of the catheter adapter. In some embodiments, the safety mechanism may be coupled with an external surface of the catheter adapter and an internal and/or external surface of a needle hub. Coupling may include threading, fitting, snapping, connecting, attaching, fastening, clipping, hooking, or any other suitable means of coupling. Non-limiting examples of safety mechanisms that include an external interlock are provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. In some embodiments, the safety mechanism may include a V-clip or a similar clip. A non-limiting example of a V-clip is provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. The V-clip may selectively retain a portion of the catheter adapter.

In some embodiments, a defeatable mechanical connection is provided between the safety mechanism and at least one other component of the IV catheter system. In some instances, the mechanical connection is defeated upon securement of the distal tip of the needle within the safety mechanism. In some embodiments, a surface of the safety mechanism is selectively coupled to one or more of the following: the catheter adapter, a blood control valve, an extension tube, and one or more paddle grips.

In some embodiments, the safety mechanism may include a safety barrel, which may be spring-loaded. For example, the safety barrel may be spring loaded as in the BD™ Insyte® Autoguard™ BC shielded protective IV catheter. In some embodiments, the safety mechanism may be passively and/or actively activated. In some embodiments, the safety mechanism may be configured to interact with a needle feature, such as a ferrule, notch, crimp or bump on the needle. In some embodiments, the safety mechanism may include an arm or lever that may be actuated to capture the distal tip within the safety mechanism and prevent the tip from emerging prior to safe disposal. In some embodiments, the safety mechanism may be attached to a body of the needle and may be capable of sliding along the length thereof.

In some embodiments, in an assembled position prior to catheterization, the safety mechanism may be disposed between the catheter adapter and the needle hub. In some embodiments, the catheter adapter and the needle hub may be spaced apart by at least a portion of the safety mechanism in the assembled position prior to catheterization. In some embodiments, in the assembled position prior to catheterization, a proximal end of the catheter adapter may be disposed between a distal end of the safety mechanism and a distal end of a grip of the needle hub, such as, for example, a paddle grip. In some embodiments, in the assembled position prior to catheterization, the proximal end of the catheter adapter body may be disposed between the distal end of the safety mechanism and a proximal end of the grip of the needle hub. In some embodiments, a portion of the safety mechanism may overlap with a portion of the grip of the needle hub. In some embodiments, at least a portion of at least one of the catheter adapter and the grip overlaps at least some portion of the safety mechanism. In some embodiments, no portion of the catheter adapter body or the grip overlaps any portion of the safety mechanism.

In any of the above described embodiments of IV catheter systems that include a catheter component with one or more wings, a wing may be formed in such a manner that it may pivot about an axis defined along the longitudinal length of the catheter component. For example, with reference to FIG. 14A, second wing 1442 may be formed of a flexible material and/or may be configured with a hinge (e.g., by forming the wing with a thinned portion along the length of the catheter hub) which allows the wing to pivot upwardly and downwardly about the longitudinal axis. One benefit of this type of pivoting is that it allows second wing 1442 to be angled upwardly away from the patient's skin during insertion. This upward angling would accommodate the clinician's finger or thumb underneath second wing 1442 thereby facilitating a shallower angle of insertion. The flexible and/or pivotable wing could then be moved downward into a flat position for securement to the patient's skin. U.S. Provisional Patent Application No. 62/247,621, which was filed on Oct. 28, 2015 and is incorporated herein by reference, discloses a number of techniques for allowing a wing to be pivoted at an angle which would be suitable for use with many of the above-described embodiments of IV catheter systems.

In any of the above described embodiments, the components of the securement platform may be formed of the same material by injection molding or other processes. This material may be an elastomeric or other low-durometer material that is relatively gentle against the patient's skin and/or dressings used to keep the catheter component in place during fluid delivery. For example, some embodiments of the present invention comprise a low-durometer material having a durometer hardness of from approximately 30 Shore A to approximately 90 Shore D. In some embodiments, a low-durometer material comprises a durometer hardness of from approximately 50 Shore A to approximately 90 Shore D. In some embodiments, the components of the securement platform may be formed of a thermoplastic elastomer (TPE) or the like.

Also, in any of the above described embodiments, the grip and/or other elements of the needle component may be formed of a clear or white material while some or all of the components of the securement platform may be formed with a color (e.g., green, pink, blue, yellow, purple, etc.) that is specific to the gauge of the catheter. The color contrast may facilitate identification by the clinician of parts of the catheter system that separate from one another during insertion of the catheter system into the vein of the patient, including, for example, hooding of the catheter.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

We claim:

1. An IV catheter system, comprising:
a catheter component comprising:
a catheter hub comprising a top, a bottom, a side disposed between the top and the bottom, a catheter hub distal end, and a catheter hub proximal end, wherein the catheter hub is shaped to define a chamber extending between the catheter hub distal end and the catheter hub proximal end, and a needle port at the catheter hub proximal end that provides access to the chamber;

a cannula extending distally from the catheter hub distal end;

a wing fixedly secured to the catheter hub and extending outwardly from the side of the catheter hub or the bottom of the catheter hub; and a needle component inserted into the needle port, the needle component comprising:

a needle hub, comprising a top, a bottom, a needle hub distal end, and a needle hub proximal end;

a needle extending distally from the needle hub distal end along an axis, wherein the needle extends distally beyond the cannula, wherein the needle comprises a bevel oriented towards the top of the needle hub; and a grip extending from the needle hub generally parallel to the axis and the wing such that the wing and the grip overlap, wherein a proximal portion of the grip is attached to the needle hub, wherein a distal portion of the grip is not attached to the needle hub and extends along a side of the needle hub between the top and the bottom of the needle hub.

2. The IV catheter system of claim 1, wherein the wing is a first wing, wherein the catheter component further comprises a second wing;

wherein the catheter hub comprises a catheter hub intermediate portion between the catheter hub proximal end and the catheter hub distal end;

wherein the catheter component further comprises an extension tubing junction extending outwardly from the catheter hub intermediate portion to connect the catheter hub to extension tubing; and wherein the second wing is disposed proximal to the extension tubing junction and extends between the catheter hub and the extension tubing junction but does not extend outwardly beyond the extension tubing junction.

3. The IV catheter system of claim 1, wherein the needle hub includes opposing side grips and the catheter component includes a push tab, wherein each of the side grips comprises a protrusion.

4. The IV catheter system of claim 3, wherein the needle component includes a flash chamber, the opposing side grips being formed on opposing sides of the flash chamber.

5. The IV catheter system of claim 1, wherein the catheter component further comprises:

an extension tubing junction extending outwardly from the catheter hub intermediate portion to connect the catheter hub to extension tubing;

wherein the extension tubing junction extends in an opposite direction of the wing.

6. The IV catheter system of claim 5, wherein the wing is a first wing, wherein the catheter component further comprises a second wing that extends in the opposite direction of the first wing, the second wing incorporating but not extending beyond the extension tubing junction.

7. The IV catheter system of claim 6, wherein the first wing is more flexible than the second wing.

8. An IV catheter system comprising:

a catheter component comprising:

a catheter hub comprising a catheter hub distal end and a catheter hub proximal end, wherein the catheter hub is shaped to define a chamber extending between the catheter hub distal end and the catheter hub proximal end, and a needle port at the catheter hub proximal end that provides access to the chamber; and a cannula extending distally from the catheter hub distal end; and a push tab positioned on a top of the catheter hub proximal end; and a needle component comprising:

a needle hub comprising a needle hub distal-most edge and a needle hub proximal end, a top of the needle hub distal-most edge including a cut-out proximate the catheter hub and aligned with the push tab, wherein an outer surface of the catheter hub extends from a proximal end of the push tab to the cut-out to form a region configured for placement of a digit of a user; and a needle extending distally from the needle hub distal end along an axis.

9. The IV catheter system of claim 8, wherein the catheter component includes a securement platform.

10. The IV catheter system of claim 9, wherein the push tab and the securement platform are connected via a connecting channel constructed of a same material as the push tab and the securement platform, wherein the connecting channel protrudes from an outer surface of the catheter hub.

11. The IV catheter system of claim 10, wherein the catheter component includes a strain relief positioned at the catheter hub distal end around the cannula, the strain relief being coupled to the securement platform by another connecting channel constructed of the same material, wherein the strain relief and the securement platform are integrally molded.

12. The IV catheter system of claim 9, wherein the catheter component comprises a first protrusion protruding from an outer surface of the catheter hub and the needle component comprises a second protrusion protruding from an inner surface of the needle hub, wherein the first protrusion and the second protrusion interface to limit rotation of the needle component relative to the catheter component and are also configured to rotate away from each other.

13. The IV catheter system of claim 8, further comprising, a flash component that includes a path-defining structure for controlling flow of blood within the flash component.

14. The IV catheter system of claim 1, wherein the grip comprises an alignment ridge that protrudes towards the wing, wherein the alignment ridge extends parallel to the axis.

15. The IV catheter system of claim 1, wherein the wing comprises a plurality of slots parallel to the axis, wherein the grip comprises a plurality of alignment ridges disposed within the plurality of slots, wherein the plurality of slots extend through a proximal end of the wing such that the alignment ridges are configured to move proximally through the slots, wherein each of the plurality of slots comprises a proximal end, wherein each of the plurality of alignment ridges comprises a distal end that contacts the proximal end of the plurality of slots to prevent the needle component from moving proximal to the catheter component when the plurality of alignment ridges are disposed within the plurality of slots.

16. The IV catheter system of claim 15, wherein each of the plurality of alignment ridges comprises a proximal end, wherein the proximal ends of each of the plurality of alignment ridges are disposed distal to the proximal end of the wing.

17. The IV catheter system of claim 2, wherein the second wing comprises a protrusion oriented substantially perpendicular to the axis and fixed between the extension tubing junction and the catheter hub.

18. The IV catheter system of claim 8, wherein the cut-out comprises an arc shape.

* * * * *